US012383143B2

(12) United States Patent
Bhawalkar et al.

(10) Patent No.: US 12,383,143 B2
(45) Date of Patent: Aug. 12, 2025

(54) FEEDBACK DETECTION FOR A TREATMENT DEVICE

(71) Applicant: Avava, Inc., Waltham, MA (US)

(72) Inventors: Jayant Bhawalkar, Auburndale, MA (US); Charles Holland Dresser, Wayland, MA (US); Rajender Katkam, Boston, MA (US)

(73) Assignee: Avava, Inc., Waltham, MA (US)

( * ) Notice: Subject to any disclaimer, the term of this patent is extended or adjusted under 35 U.S.C. 154(b) by 0 days.

(21) Appl. No.: 17/886,086

(22) Filed: Aug. 11, 2022

(65) Prior Publication Data
US 2023/0107384 A1   Apr. 6, 2023

Related U.S. Application Data

(63) Continuation of application No. 16/447,941, filed on Jun. 20, 2019.
(Continued)

(51) Int. Cl.
*A61B 5/00* (2006.01)
*A61B 18/20* (2006.01)
(Continued)

(52) U.S. Cl.
CPC .......... *A61B 5/0068* (2013.01); *A61B 5/0064* (2013.01); *A61B 5/4836* (2013.01);
(Continued)

(58) Field of Classification Search
CPC .. A61B 5/442–445; A61B 2018/00636; A61B 2018/00452; A61B 18/201–203; A61N 5/0616; A61N 2007/0034
See application file for complete search history.

(56) References Cited

U.S. PATENT DOCUMENTS 5,446,538 A     8/1995  Noll
5,995,867 A *  11/1999  Zavislan ............ G02B 21/0028
                                                        250/461.2
(Continued)

FOREIGN PATENT DOCUMENTS

CN       101677835 A    3/2010
CN       203971205 U   12/2014
(Continued)

OTHER PUBLICATIONS

Extended European Search Report Corresponding to European Patent Application No. EP19822533.6, mailed on Mar. 31, 2022, 7 pages.
(Continued)

*Primary Examiner* — Keith M Raymond
*Assistant Examiner* — Milton Truong
(74) *Attorney, Agent, or Firm* — Mintz Levin Cohn Ferris Glovsky and Popeo, P.C.

(57) ABSTRACT

A system includes a focus optic configured to converge an electromagnetic radiation (EMR) beam to a focal region located along an optical axis. The system also includes a detector configured to detect a signal radiation emanating from a predetermined location along the optical axis. The system additionally includes a controller configured to adjust a parameter of the EMR beam based in part on the signal radiation detected by the detector. The system also includes a window located a predetermined depth away from the focal region, between the focal region and the focus optic along the optical axis, wherein the window is configured to make contact with a surface of a tissue.

12 Claims, 36 Drawing Sheets

Related U.S. Application Data

(60) Provisional application No. 62/688,913, filed on Jun. 22, 2018, provisional application No. 62/688,940, filed on Jun. 22, 2018, provisional application No. 62/688,855, filed on Jun. 22, 2018.

(51) Int. Cl.
*A61B 90/20* (2016.01)
*A61N 1/44* (2006.01)
*A61N 5/06* (2006.01)
*A61B 17/00* (2006.01)
*A61B 18/00* (2006.01)
*H05H 1/46* (2006.01)

(52) U.S. Cl.
CPC ............ *A61B 5/742* (2013.01); *A61B 18/201* (2013.01); *A61B 18/203* (2013.01); *A61B 90/20* (2016.02); *A61N 1/44* (2013.01); *A61N 5/0616* (2013.01); *A61B 5/443* (2013.01); *A61B 2017/00057* (2013.01); *A61B 2017/0019* (2013.01); *A61B 2018/00458* (2013.01); *A61B 2018/00642* (2013.01); *A61B 2018/00904* (2013.01); *A61B 2018/202* (2013.01); *A61B 2018/20355* (2017.05); *A61B 2018/20361* (2017.05); *A61N 2005/0644* (2013.01); *H05H 1/46* (2013.01)

(56) References Cited

U.S. PATENT DOCUMENTS

| | | | |
|---|---|---|---|
| 6,044,288 | A | 3/2000 | Wake et al. |
| 6,074,382 | A | 6/2000 | Asah et al. |
| 6,165,170 | A | 12/2000 | Wynne et al. |
| 7,282,060 | B2 | 10/2007 | Debenedictis et al. |
| 8,523,926 | B2 | 9/2013 | Neev |
| 9,414,888 | B2 | 8/2016 | Liu et al. |
| 9,486,284 | B2 | 11/2016 | Depfenhart et al. |
| 11,457,816 | B2 | 10/2022 | Bhawalkar et al. |
| 2005/0154380 | A1 | 7/2005 | Debenedictis et al. |
| 2006/0084957 | A1 | 4/2006 | Delfyett et al. |
| 2006/0106371 | A1 | 5/2006 | Muhlhoff et al. |
| 2006/0217691 | A1 | 9/2006 | Schuele et al. |
| 2007/0173791 | A1 | 7/2007 | Raksi |
| 2008/0033406 | A1 | 2/2008 | Angeley et al. |
| 2008/0306471 | A1 | 12/2008 | Altshuler et al. |
| 2009/0248004 | A1 | 10/2009 | Altshuler et al. |
| 2010/0130969 | A1 | 5/2010 | Batterson et al. |
| 2011/0022039 | A1 | 1/2011 | Spikker et al. |
| 2011/0100967 | A1 | 5/2011 | Yoo et al. |
| 2014/0005756 | A1 | 1/2014 | Liu et al. |
| 2014/0094711 | A1 | 4/2014 | Sondermann et al. |
| 2014/0128853 | A1* | 5/2014 | Angeley ............ A61F 9/00827 606/4 |
| 2014/0288621 | A1 | 9/2014 | Efremkin |
| 2014/0364744 | A1* | 12/2014 | Wellhoefer ......... A61F 9/00802 600/407 |
| 2016/0074116 | A1 | 3/2016 | Varghese et al. |
| 2016/0199132 | A1 | 7/2016 | Anderson et al. |
| 2016/0249982 | A1 | 9/2016 | Varghese et al. |
| 2016/0256324 | A1 | 9/2016 | Suzuki |
| 2016/0278981 | A1* | 9/2016 | Kempe ............... A61F 9/00802 |
| 2016/0317226 | A1* | 11/2016 | Jagdeo .................. A61B 90/06 |
| 2017/0151330 | A1 | 6/2017 | Harris et al. |
| 2017/0247797 | A1 | 8/2017 | Zhou et al. |
| 2017/0281077 | A1* | 10/2017 | Pyun ...................... A61B 5/441 |
| 2017/0281405 | A1 | 10/2017 | Ha |
| 2018/0049689 | A1* | 2/2018 | Chung ................. A61B 5/0059 |
| 2018/0085004 | A1* | 3/2018 | Pyun ..................... A61B 5/1032 |
| 2018/0177550 | A1 | 6/2018 | Anderson ............ A61B 18/203 |
| 2018/0325593 | A1* | 11/2018 | McMillan ........... A61N 5/0616 |
| 2020/0038678 | A1* | 2/2020 | Holmes ................ A61B 5/0066 |
| 2021/0052212 | A1* | 2/2021 | Yaroslavsky ........ A61B 5/0066 |
| 2021/0212568 | A1 | 7/2021 | Bhawalkar et al. |

FOREIGN PATENT DOCUMENTS

| | | |
|---|---|---|
| CN | 107267964 A | 10/2017 |
| JP | 2007531558 A | 11/2007 |
| JP | 2007532225 A | 11/2007 |
| JP | 2008100057 A | 5/2008 |
| JP | 2008284382 A | 11/2008 |
| JP | 2010535556 A | 11/2010 |
| JP | 2015134228 A | 7/2015 |
| JP | 2016190090 A | 11/2016 |
| JP | 2016539665 A | 12/2016 |
| JP | 2017131303 A | 8/2017 |
| JP | 2020503108 A | 1/2020 |
| JP | 2020503119 A | 1/2020 |
| WO | 2014146029 A1 | 9/2014 |
| WO | 2015021462 A1 | 2/2015 |
| WO | 2018029196 A1 | 2/2018 |
| WO | 2018115415 A1 | 6/2018 |

OTHER PUBLICATIONS

International Search Report and Written Opinion for corresponding International Application No. PCT/US2019/038348, mailed on Oct. 3, 2019, 8 pages.

Chung et al. (2009) "Surgical Applications of Femtosecond Lasers", Journal of biophotonics, 2(10):557-572.

Han et al. (2015) "Differentiation of Cutaneous Melanoma from Surrounding Skin Using Laser-Induced Breakdown Spectroscopy", Biomed Opt Express, 7(1):57-66.

Kim et al. (2020) "Laser-Induced Optical Breakdown Effects Of Micro-Lens Arrays And Diffractive Optical Elements On Ex Vivo Porcine Skin After 1064 Nm Picosecond Laser Irradiation", Biomed Opt Express, 11(12):7286-7296.

Roberts, Joan E. (2016) "Photobiology of the Human Lens", https://web.archive.org/web/20160106212227/, 15 pages.

Vogel et al. (1994) "Intraocular Photodisruption With Picosecond and Nanosecond Laser Pulses: Tissue Effects in Cornea, Lens, and Retina", Investigative Ophthalmology & Visual science, 35(7):3032-3044.

Xie et al. (Dec. 10, 2009) "Measurement of Optical Properties of Biological Tissue Based on Scanning Photoacoustic Technology", Lasers and Optoelectronics, 103-107.

\* cited by examiner

2710

2720

FEEDBACK DETECTION FOR A TREATMENT DEVICE

CROSS-REFERENCE TO RELATED APPLICATIONS

This application is a continuation of U.S. application Ser. No. 16/447,937, entitled "Feedback Detection for a Treatment Device," filed Jun. 20, 2019, which claims the benefit of U.S. Provisional Application No. 62/688,940, entitled "Pigment Detection for a Therapeutic Device," filed Jun. 22, 2018, U.S. Provisional Application No. 62/688,913, entitled "Diffractive Optics for EMR-Based Tissue Treatment," filed Jun. 22, 2018, and U.S. Provisional Application No. 62/688,855, entitled "Selective Plasma Generation for Tissue Treatment," filed Jun. 22, 2018. The entirety of each of these applications is incorporated by reference.

BACKGROUND

Melasma or chloasma faciei (the mask of pregnancy) is a common skin condition characterized by tan to dark gray-brown, irregular, well-demarcated macules and patches on the face. The macules are believed to be due to overproduction of melanin, which is taken up by the keratinocytes (epidermal melanosis) or deposited in the dermis (dermal melanosis, melanophages). The pigmented appearance of melasma can be aggravated by certain conditions such as pregnancy, sun exposure, certain medications (e.g., oral contraceptives), hormonal levels, and genetics. The condition can be classified as epidermal, dermal, or mixed depending on the location of excess melanin. Exemplary symptoms of melasma primarily include the dark, irregularly-shaped patches or macules, which are commonly found on the upper cheek, nose, upper lip, and forehead. These patches often develop gradually over time.

Melasma can cause considerable embarrassment and distress. It is especially problematic for darker skin tones and women, impacting up to 30% of Southeastern Asian women, as well as many Latin American women. Only 1-in-4 to 1-in-20 affected individuals are male, depending on the population study. Approximately 6 million women in the US cope with melasma, according to the American Academy of Dermatology. Worldwide, numbers of those with melasma are estimated at 157 million people in Asia/Pacific, 58 million in Latin America, and 3 million in Europe. Melasma generally appears between ages 20-40. As no cure exists for melasma, US patients undergoing treatment for melasma currently try many different types of treatment. 79% of US patient's topical medications; while, 37% use oral treatment; and, 25% use a laser.

Unlike other pigmented structures that are typically present in the epidermal region of skin (i.e., at or near the tissue surface), dermal (or deep) melasma is often characterized by widespread presence of melanin and melanophages in portions of the underlying dermis. Accordingly, treatment of dermal melasma (e.g., lightening of the appearance of darkened pigmented regions) can be particularly challenging because of the greater difficulty in accessing and affecting such pigmented cells and structures located deeper within the skin. Accordingly, conventional skin rejuvenation treatments such as facial peels (laser or chemical), dermabrasion, topical agents, and the like, which primarily affect the overlying epidermis (and are often the first course of treatment for melasma), may not be effective in treating dermal melasma.

Additionally, up to 50% of melasma patients also experience other hyperpigmentation problems. Among all pigmentary disorders, melasma is the one for which the largest proportion of patients are likely to visit a dermatologist. The management of this disorder remains challenging given the incomplete understanding of the pathogenesis, its chronicity, and recurrence rates. After treatment, the melasma may recur, often worse than prior to treatment. And, topical treatments which may work in treating epidermal melasma fail to effectively treat dermal or mixed melasma.

SUMMARY

It has been observed that application of light or optical energy of certain wavelengths can be strongly absorbed by pigmented cells, thereby damaging them. However, an effective treatment of dermal melasma using optical energy introduces several obstacles. For example, pigmented cells in the dermis must be targeted with sufficient optical energy of appropriate wavelength(s) to disrupt or damage them, which may release or destroy some of the pigmentation and reduce the pigmented appearance. However, such energy can be absorbed by pigment (e.g., melanin) in the overlying skin tissue, such as the epidermis and upper dermis. This near-surface absorption can lead to excessive damage of the outer portion of the skin, and insufficient delivery of energy to the deeper dermis to affect the pigmented cells therein. Moreover, moderate thermal injury to melanin containing melanocytes located in the basal layer of the epidermis can trigger an increase in the production of melanin (e.g., hyperpigmentation) and severe thermal damage to the melanocytes can trigger a decrease in the production of melanin (e.g., hypopigmentation).

The Pigmentary Disorders Academy (PDA) evaluated the clinical efficacy of different types of melasma treatment in an attempt to gain a consensus opinion on treatment. Their efforts were published in a paper titled "Treatment of Melasma" by M. Rendon et al. published in The Journal of the American Academy of Dermatology in May 2006. Rendon et al. reviewed literature related to melasma treatment for the 20 years prior and made determinations based upon their review. Rendon et al. determined that "The consensus of the group was that first line therapy for melasma should consist of effective topical therapies, mainly fixed triple combinations." And, that "[l]asers should rarely be used in the treatment of melasma and, if applied, skin type should be taken into account."

A criticism of Rendon et al.'s comprehensive report on melasma treatment could be that it is dated, having been published in 2006. A more recent article by M. Sadeghpour et al. published in 2018 in Advances in Cosmetic Surgery entitled "Advances in the Treatment of Melasma" attempts to review current melasma treatment modalities. Sadeghpour et al. likewise conclude that "Topical therapy remains the gold standard for first-line therapy for melasma using broad-spectrum sunscreens and either hydroquinone 4% cream, tretinoin, or triple-combination creams." Sadeghpour et al. note that dermal melasma is more difficult to treat "because destruction of these melanosomes is often accompanied by significant inflammation that in turn stimulates further melanogenesis."

Therefore there is a large unmet need for a more efficacious and safe treatment for melasma and other hard to treat pigmentary disorders.

Approaches have been developed that involve application of optical energy to small, discrete treatment locations in the skin that are separated by healthy tissue to facilitate healing.

Accurately targeting the treatment locations (e.g., located in dermal layer) with desirable specificity while avoiding damage to healthy tissue around the treatment location (e.g., in the epidermal layer) can be challenging. This requires, for example, an optical system with high numerical aperture (NA) for focusing a laser beam to a treatment location. The high NA optical system delivers a sufficiently high in-focus fluence (i.e., energy density) to the dermis, while maintaining a sufficiently low out-of-focus fluence in the epidermis. U.S. Patent Application Publication No. 2016/0199132, entitled "Method and Apparatus for Treating Dermal Melasma" has shown this technique to be advantageous for treatment of dermal pigmentation including Melasma in research settings.

However, this technique requires that a focal region formed by the high NA optical system be located precisely (e.g., within a tolerance of about +/−25 µm) at a depth within a target tissue. For example, melanocytes are typically located within a basal layer of the epidermis at a depth of about 100 µm. Dermal melanophages responsible for deep melasma can be present in the upper dermis just beneath the basal layer of the epidermis (e.g., 50 µm below). Therefore, a difference in focal region depth of a few-tens of micrometers can become the difference between effectively treating dermal pigmentation and inadvertently damaging melanocytes and potentially causing debilitating cosmetic results (e.g., hypopigmentation). In part for this reason, an EMR-based system that effectively treats dermal pigmentation has yet to be made commercially available.

Therefore, it is desirable to develop an EMR-based treatment system that reliably locates a focal region to a prescribed depth within a tolerance of tens of micrometers (e.g., about ±100 µm, about ±10 µm, about ±1 µm, etc.) Further, it can be desirable that the EMR-based treatment system achieve this performance in part through calibration, for example by periodically placing the focal region at a reference having a known depth. Furthermore, it can be desirable that the reference used during calibration be used during treatment. For example, the reference can include an interface that establishes a robust contact with the treatment region and stabilizes the treatment region.

Some developed approaches for dermal pigment treatment, like those outlined by Anderson et al., can employ selective thermionic plasma generation as a means of treatment. In these cases, laser fluence at a focal region within the dermis is above a thermionic plasma threshold (e.g., $10^9$ W/cm$^2$), but below an optical breakdown threshold (e.g., $10^{12}$ W/cm$^2$). This causes plasma formation selectively when the focal region is located at a pigmented tissue (e.g., melanin) within the dermis without generating a plasma in unpigmented tissue in the dermis or pigmented epidermal tissue above the focal region. The selectively formed thermionic plasma disrupts or damages the pigment and surrounding tissue. This disruption ultimately leads to clearing of the dermal pigment. Therefore, presence of plasma during treatment within a tissue being treated can be indicative of efficacious treatment in some embodiments. As parameter selection for laser-based skin treatments often depends on skin type and is therefore dependent upon each individual patient, the presence of plasma may be used as an indication that correct treatment parameters have been achieved. This feedback is therefore desirable for successful treatment of a condition, such as melasma, in populations that are generally underserved by laser-based treatment (e.g., those with darker skin types).

Alternatively, in some cases, properties of a detected plasma may indicate that the treatment is having an adverse effect. For example, in some embodiments a transmissive window is placed onto a skin being treated to reference the skin and keep it from moving during treatment. It is possible for treatment to fail when the laser beam etches the window. Etching of the window prevents further efficient transmission of the laser to the tissue and often coincides with very bright plasma formation in the window itself. If treatment continues with an etched window it is likely that heat accumulation within the window will cause damage to the epidermis of the skin (e.g., burning and blistering). It is therefore advantageous to employ feedback to detect plasma formation within the window and stop treatment when it occurs.

From the foregoing, it can be understood that plasma formation during treatment can be both advantageous and deleterious to treatment. Thus, systems and methods that provide plasma detection can detect properties of the plasma and distinguish between plasma beneficial to tissue treatment and plasma detrimental to tissue treatment continuously in real-time.

It can be desirable in some embodiments to image the tissue being treated from the perspective of the treatment device and project this view onto a screen for viewing by the practitioner. In one aspect, placement of a treatment device typically occludes a practitioner's view of the tissue being treated. Thus, tissue imaging can facilitate accurate placement of the treatment device for targeting affected tissue. Additionally, as the goal of treatment of many pigmentary conditions is aesthetic (e.g., improve the appearance of the skin) it images of the skin can be consistently acquired under repeatable imaging conditions (e.g., lighting and distance) during imaging so that results of treatment may be ascertained.

It has long been the hope of those suffering with pigmentary conditions, such as melasma, that an EMR-based treatment for their condition be made widely available. Accordingly, as discussed in greater detail below, an EMR-based treatment system is provided that provides repeatable depth positioning of the focal region within a target tissue. The disclosed systems and methods can also detect and record plasma events in order to document and track treatment safety and effectiveness and image the treated tissue to accurately deliver EMR to the treatment region. These capabilities address a number of technical problems currently preventing widespread successful treatment of dermal pigmentation and other hard to treat skin conditions with EMR-based systems.

In one embodiment, a system is provided. The system can include a focus optic, a detector, a controller, and a window. The focus optic can be configured to converge an electromagnetic radiation (EMR) beam to a focal region located along an optical axis. The detector can be configured to detect a signal radiation emanating from a predetermined location along the optical axis. The controller can be configured to adjust a parameter of the EMR beam based in part on the signal radiation detected by the detector. The window can be located a predetermined depth away from the focal region, between the focal region and the focus optic along the optical axis. The window can be configured to make contact with a surface of a tissue.

In another embodiment, the EMR beam can be configured to generate a plasma at the predetermined location along the optical axis. The signal radiation can emanate from the plasma.

In another embodiment, the signal radiation can emanate from an interaction between the EMR beam and the window.

In another embodiment, the focus optic can be further configured to image the signal radiation detected by the detector.

In another embodiment, the system can further include a scanner configured to scan the focal region from a first region within the tissue to a second region within the tissue.

In another embodiment, the EMR beam can be further configured to generate a thermionic plasma at the focal region.

In another embodiment, the window can be further configured to transmit the EMR beam.

In another embodiment, the focus optic can be further configured to converge the EMR beam at a numerical aperture (NA) of at least 0.3.

In another embodiment, the parameter of the EMR beam can include at least one of: a pulse energy, a repetition rate, a pulse duration, a focal region location, a focal region size, a wavelength, or a power.

In another embodiment, the signal radiation can include at least one of: a visible light, an infrared light, an acoustic signal, an ultrasonic signal, a radio signal, or a temperature.

In an embodiment, a method is provided. The method can include contacting, using a window, a surface of a tissue. The method can also include converging, using a focus optic, an electromagnetic radiation (EMR) beam to a focal region located along an optical axis. The method can further include detecting, using a detector, a signal radiation emanating from a location along the optical axis. The method can additionally include adjusting, using a controller, a parameter of the EMR beam based in part on the detected signal radiation. The method can also include positioning the focal region within the tissue at a predetermined distance from the surface of the tissue.

In another embodiment, the method can further include generating, using the EMR beam, a plasma at the location along the optical axis. The signal radiation can emanate from the plasma.

In another embodiment, the method can further include directing the converging EMR beam incident upon the window. The signal radiation can emanate from an interaction between the EMR beam and the window.

In another embodiment, the method further includes imaging, using the focus optic, the signal radiation incident the detector.

In another embodiment, the method further includes scanning, using a scanner, the focal region from a first region within the tissue to a second region within the tissue.

In another embodiment, the method further includes generating, using the EMR beam, a thermionic plasma at the focal region.

In another embodiment, the method further includes transmitting the EMR beam through the window.

In another embodiment, the focus optic is further configured to converge the EMR beam at a numerical aperture (NA) of at least 0.3.

In another embodiment, the parameter of the EMR beam can include at least one of: a pulse energy, a repetition rate, a pulse duration, a focal region location, a focal region size, a wavelength, or a power.

In another embodiment, the signal radiation includes at least one of: a visible light, an infrared light, an acoustic signal, an ultrasonic signal, a radio signal, or a temperature.

In one embodiment, a system is provided. The system can include a focus optic, a window, an optical detector, a controller, and a stage. The focus optic can be configured to focus an electromagnetic radiation (EMR) beam to a focal region located along an optical axis. The window can intersect the optical axis and it can be configured to contact a surface of a tissue. The optical detector can be configured to detect a signal radiation emanating from an interaction of the EMR beam with the window. The controller can be configured to determine a reference position where a portion of the focal region is substantially coincident with a surface of the window. The stage can be configured to translate the focal region to a treatment position that is located at a predetermined distance from the reference position.

In another embodiment, the focus optic and the stage can be configured to position the treatment position within a tissue.

In another embodiment, the treatment position can be located within a dermal tissue.

In another embodiment, the EMR beam can be configured to generate a thermionic plasma at the focal region.

In another embodiment, the EMR beam can include a pulse having a pulse duration of at least 1 picosecond.

In another embodiment, the focus optic can be further configured to image the signal radiation incident the detector.

In another embodiment, the controller can be further configured to determine the reference position by determining a transverse width of the EMR beam incident the surface of the window, based upon the signal radiation, and translating the focal region until the transverse width has a minimum value.

In another embodiment, the detector can be further configured to detect an intensity of the signal radiation, and the controller can be further configured to determine the reference position by translating the focal region until the intensity of the signal radiation has a maximum value.

In another embodiment, the focus optic can be further configured to converge a second EMR beam to a second focal region. The second EMR beam can have at least one of: a wavelength that is identical to a wavelength of the EMR beam or a wavelength that is different to the wavelength of the EMR beam. The second EMR beam can be configured to effect a desired change in the tissue.

In another embodiment, the stage can be configured to translate the focal region by translating at least one of: the focus optic, one or more optical elements, and the window.

In an embodiment a method is provided that includes converging, using a focus optic, an electromagnetic radiation (EMR) beam to a focal region located along an optical axis. The method can also include detecting, using a detector, a signal radiation emanating from an interaction of the EMR beam and a window intersecting the optical axis. The method can further include determining, using a controller, a reference position along the optical axis based upon the detected signal radiation. At the reference position, a portion of the focal region can be substantially coincident with a surface of the window. The method can further include translating the focal region to a treatment position located a predetermined distance from the reference position.

In another embodiment, the method can further include contacting, using the window, a surface of a tissue, such that the treatment position can be located within the tissue.

In another embodiment, the predetermined distance can be configured to locate the treatment position within a dermal tissue.

In another embodiment, the EMR beam can be configured to generate a thermionic plasma in the focal region.

In another embodiment, the EMR beam can include a pulse having a pulse duration of at least 1 picosecond.

In another embodiment, detecting the signal radiation can further include imaging, using the focus optic, the signal radiation incident the detector.

In another embodiment, determining the reference position can further include determining, using the controller, a transverse width of the EMR beam incident the surface of the window, based upon the signal radiation, and translating the focal region along the optical axis until the transverse width has a minimum value.

In another embodiment, determining the reference position can further include detecting, using the detector, an intensity of the signal radiation, and translating the focal region until the intensity of the signal radiation has a maximum value.

In another embodiment, the method can further include converging, using the focus optic, a second EMR beam to a second focal region. The second EMR beam can have at least one of: a wavelength that is identical to a wavelength of the EMR beam or a wavelength that is different to the wavelength of the EMR beam. The second EMR beam can be configured to effect a desired change in the tissue.

In another embodiment, translating the focal region can further include translating at least one of the focus optic, one or more optical elements, and the window.

In one embodiment, a system is provided and can include a radiation source, a window, a focus optic, a scanner, a detector, and a controller. The radiation source can be configured to generate a treatment radiation configured to effect a desired change in a tissue. The window can be configured to contact a surface of the tissue. The focus optic can be configured to focus the treatment radiation to a focal region configured to generate a plasma at the focal region. The scanner can be configured to scan the focal region. The detector can be configured to detect a signal radiation emanating from the plasma. The controller can be configured to determine if the plasma is at least partially located within the window, based on the detected signal radiation, and to control one or more parameters of the treatment radiation based on the determination.

In another embodiment, the controller can be further configured to determine one or more properties of the plasma.

In another embodiment, the one or more properties of the plasma can include at least one of a presence of a plasma, an intensity of a plasma, a spectral content of a plasma, and a position of a plasma.

In another embodiment, the controller can be further configured to terminate the treatment radiation based on the determination.

In another embodiment, the one or more parameters of the treatment radiation can include at least one of an energy per pulse, a repetition rate, a position of a focal region, and a size of a focal region.

In another embodiment, the desired change in the tissue can include generation of selective thermionic plasma in presence of a chromophore.

In another embodiment, the controller can be further configured to record a property of the signal radiation.

In another embodiment, the controller can be further configured to record a first property of a first signal radiation emanating from a first plasma at a first location, map the first property to a coordinate for the first location, record a second property of a second signal radiation emanating from a second plasma at a second location, and map the second property to a coordinate for the second location.

In another embodiment, the controller can be further configured to determine if the plasma is at least partially located within the window based on an intensity of the signal radiation.

In another embodiment, the controller can be further configured to determine if the plasma is at least partially located within the window based on a spectral component of the signal radiation.

In an embodiment, a method is provided. The method can include generating, with a radiation source, a treatment radiation configured to effect a desired change in a tissue. The method can also include contacting, using a window, a surface of the tissue. The method can further include focusing, with a focus optic, the treatment radiation to a focal region. The method can additionally include scanning, with a scanner, the focal region. The method can additionally include generating, with the treatment radiation, a plasma at the focal region. The method can also include detecting, with a detector, a signal radiation emanating from the plasma. The method can additionally include determining, using a controller, if the plasma is at least partially located within the window, based on the detected signal radiation. The method can further include controlling, using the controller, one or more parameters of the treatment radiation based on the determination.

In another embodiment, the method can further include determining, with the controller, one or more properties of the plasma.

In another embodiment, the one or more properties of the plasma can include at least one of a presence of a plasma, an intensity of a plasma, a spectral content of a plasma, and a position of a plasma.

In another embodiment, the method can further include terminating, using the controller, the treatment radiation based on the determination.

In another embodiment, the one or more parameters of the treatment radiation can include at least one of an energy per pulse, a repetition rate, a position of a focal region, and a size of a focal region.

In another embodiment, the desired change in the tissue can be a generation of a selective thermionic plasma in presence of a chromophore.

In another embodiment, the method can include recording, using the controller, a property of the signal radiation.

In another embodiment, the method can further include recording, using the controller, a first property of a first signal radiation emanating from a first plasma at a first location, mapping the first property to a coordinate for the first location, recording, using a data acquisition device, a second property of a second signal radiation emanating from a second plasma at a second location, and, mapping the second property to a coordinate for the second location.

In another embodiment, determining if the plasma is at least partially located within the window can be based on an intensity of the signal radiation.

In another embodiment, determining if the plasma is at least partially located within the window can be based on a spectral component of the signal radiation.

In an embodiment, a system is provided and can include a radiation source, a focus optic, a detector, and a treatment radiation. The radiation source can be configured to illuminate a tissue with an imaging radiation. The focus optic can be configured to image a view of the tissue. The detector can be configured to detect an image of the view of the tissue. The treatment radiation can be configured to be focused, using the focus optic, to a focal region within a target treatment region designated based in part on the image.

The system can further include a scanner configured to scan the view to a second region of the tissue. The focus optic can be further configured to image a second image of the view from the second region of the tissue. The detector can be further configured to detect the second image.

In another embodiment, the scanner can be further configured to scan the focal region within the target treatment region.

In another embodiment, the system can further include a controller configured to stitch the image and the second image into a map. The map can be configured to be used in the determination of at least one of: a diagnosis, a treatment plan, and a treatment parameter for the treatment radiation.

In another embodiment, the system can further include a window configured to contact a surface of the tissue, such that the focal region is located a predetermined depth from the surface of the tissue.

In another embodiment, the system can further include a controller configured to record the image.

In another embodiment, the system can further include a controller configured to control a parameter of the treatment radiation based in part on the image.

In another embodiment, the treatment radiation can be configured to selectively generate a plasma at a chromophore proximal the focal region.

In another embodiment, the focus optic can be further configured to image the first image using at least one of: microscopic imaging, wide field of view imaging, and reflectance confocal imaging.

In another embodiment, the system can further include a display configured to display the image.

In an embodiment, a method is provided. The method can include illuminating, using a radiation source, a tissue with an imaging radiation. The method can also include imaging, using a focus optic, an image of a view of the tissue. The method can additionally include detecting, using a detector, the image. The method can also include designating a target treatment region of the tissue based in part on the image. The method can further include converging, using the focus optic, a treatment radiation to a focal region within the target treatment region.

In another embodiment, the method can further include scanning, using a scanner, the view to a second region of the tissue, imaging, using the focus optic, a second image of the view from the second region of the tissue, and detecting, using the detector, the second image.

In another embodiment, the method can further include scanning, using the scanner, the focal region within the target treatment region.

In another embodiment, the method can further include stitching the image and the second image together into a map.

In another embodiment, the method can further include determining from the map at least one of: a diagnosis, a treatment plan, and a treatment parameter for the treatment radiation.

In another embodiment, the method can further include contacting, using a window, a surface of a tissue, such that the focal region is located a predetermined depth from the surface of the tissue.

In another embodiment, the method can further include recording, using a controller, the image.

In another embodiment, the method can further include controlling, using the controller, a parameter of the treatment radiation based in part on the image.

In another embodiment, the treatment radiation can be configured to selectively generate a plasma at a chromophore proximal the focal region.

In another embodiment, imaging the first image can include at least one of: microscopic imaging, wide field of view imaging, or reflectance confocal imaging.

In another embodiment, the method can further include displaying, using a display, the image.

BRIEF DESCRIPTION OF THE DRAWINGS

Embodiments of the disclosure will be more fully understood from the following detailed description taken in conjunction with the accompanying drawings, in which.

Figure 1:
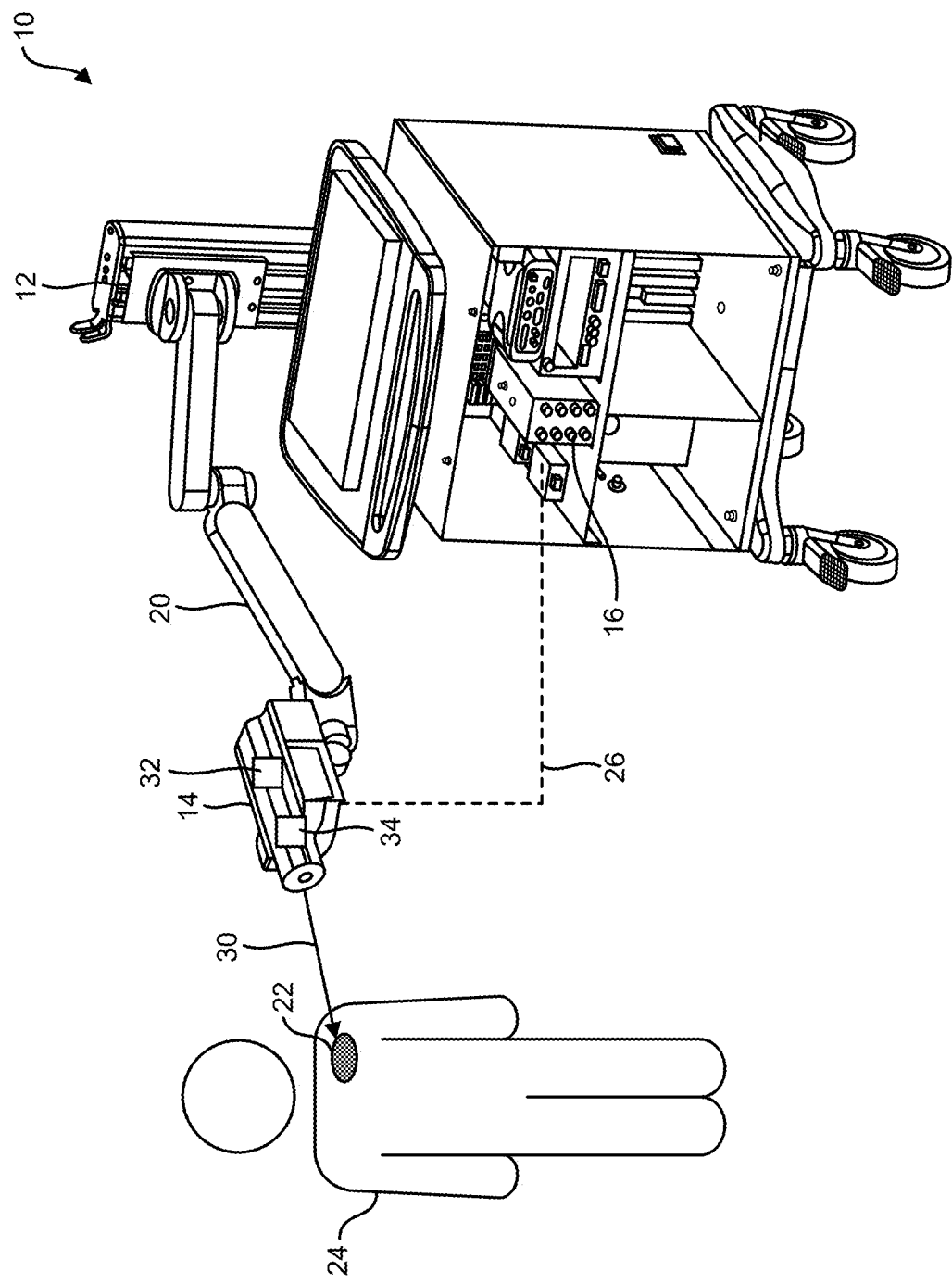
FIG. 1 illustrates an exemplary embodiment of a treatment system, according to some embodiments.

It is noted that the drawings are not necessarily to scale. The drawings are intended to depict only typical aspects of the subject matter disclosed herein, and therefore should not be considered as limiting the scope of the disclosure. The systems, devices, and methods specifically described herein and illustrated in the accompanying drawings are non-limiting exemplary embodiments.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Embodiments of the disclosure are discussed in detail below with respect to treatment of pigmentary conditions of the skin, such as melasma, to improve the appearance of such a pigmentary condition. However, the disclosed embodiments can be employed for treatment of other pigmentary and non-pigmentary conditions and other tissue and non-tissue targets without limit. Examples of pigmentary conditions can include, but are not limited to, post inflammatory hyperpigmentation (PIH), dark skin surrounding eyes, dark eyes, café au lait patches, Becker's nevi, Nevus of Ota, congenital melanocytic nevi, ephelides (freckles) and lentigo. Additional examples of pigmented tissues and structures that can be treated include, but are not limited to, hemosiderin rich structures, pigmented gallstones, tattoo-containing tissues, and lutein, zeaxanthin, rhodopsin, carotenoid, biliverdin, bilirubin and hemoglobin rich structures. Examples of targets for the treatment of non-pigmented structures, tissues and conditions can include, but are not limited to, hair follicles, hair shafts, vascular lesions, infectious conditions, sebaceous glands, acne, and the like.

Methods of treating various skin conditions, such as for cosmetic purposes, can be carried out using the systems described herein. It is understood that, although such methods can be conducted by a physician, non-physicians, such as aestheticians and other suitably trained personnel may use the systems described herein to treat various skin conditions with and without the supervision of a physician.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, high numerical aperture (NA) optical treatment systems are described that can focus electromagnetic radiation (EMR) (e.g., a laser beam) to a treatment region in a tissue. Unless otherwise noted, the terms EMR, EMR beam, and laser beam are employed interchangeably herein. The focused laser beam can deliver optical energy to the treatment region without harming the surrounding tissue. The delivered optical energy can, for example, disrupt pigmented chromophores and/or targets in a treatment region of the dermal layer of the skin, without affecting the surrounding regions (e.g., overlying epidermal layer, other portions of the dermal layer, and the like). In other implementations, the delivered optical energy can cause tattoo removal or alteration, or hemoglobin-related treatment.

Exemplary methods and devices for treating skin conditions with light or optical energy are disclosed in U.S. Patent Application Publication No. 2016/0199132, entitled "Method and Apparatus for Treating Dermal Melasma," and U.S. Provisional Application No. 62/438,818, entitled "Method and Apparatus for Selective Treatment of Dermal Melasma," each of which is hereby incorporated by reference herein in their entirety.

In general, systems and corresponding methods are provided for treatment of pigmentary conditions in tissues. As discussed in greater detail below, the disclosed systems and methods employ electromagnetic radiation (EMR), such as laser beams, to deliver predetermined amounts of energy to a target tissue. The EMR can be focused to a focal region and the focal region can be translated or rotated in any direction with respect to the target tissue. The predetermined amount of radiation can be configured to thermally disrupt or otherwise damage portions of the tissue exhibiting the pigmentary condition. In this manner, the predetermined amount of energy can be delivered to any position within the target tissue for treatment of the pigmentary condition such as to improve the appearance thereof.

FIG. 1 illustrates one exemplary embodiment of a treatment system 10. As shown, the treatment system 10 includes a mounting platform 12, emitter 14, and a controller 16. The mounting platform 12 can include one or more manipulators or arms 20. The arms 20 can be coupled to the emitter 14 for performing various treatments on a target tissue 22 of a subject 24. Operation of the mounting platform 12 and emitter 14 can be directed by a user, manually or using the controller 16 (e.g., via a user interface). In certain embodiments (not shown), the emitter can have a hand-held form factor and the mounting platform 12 can be omitted.

The emitter 14 and controller 16 (and optionally the mounting platform 12) can be in communication with one another via a communications link 26, which can be any suitable type of wired and/or wireless communications link carrying any suitable type of signal (e.g., electrical, optical, infrared, etc.) according to any suitable communications protocol.

Embodiments of the controller 16 can be configured to control operation of the emitter 14. In one aspect, the controller 16 can control movement of EMR 30. As discussed in detail below, the emitter 14 can include a source 32 for emission of the EMR 30 and a scanning system 34 for manipulation of the EMR 30. As an example, the scanning system 34 can be configured to focus EMR 30 to a focal region and translate and/or rotate this focal region in space. The controller 16 can send signals to the source 32, via the communications link 26 to command the source 32 to emit the EMR 30 having one or more selected properties, such as wavelength, power, repetition rate, pulse duration, pulse energy, focusing properties (e.g., focal volume, Raleigh length, etc.). In another aspect, the controller 16 can send signals to the scanning system 34, via the communications link 26 to command the scanning system 34 to move the focal region of the EMR 30 with respect the target tissue 22 in one or more translation and/or rotation operations.

Embodiments of the treatment system 10 and methods are discussed herein in the context of targets within skin tissue, such as a dermal layer. However, the disclosed embodiments can be employed for treatment of any tissue in any location of a subject, without limit. Examples of non-skin tissues can include, but are not limited to, surface and sub-surface regions of mucosal tissues, genital tissues, internal organ tissues, and gastrointestinal tract tissues.

Figure 2:
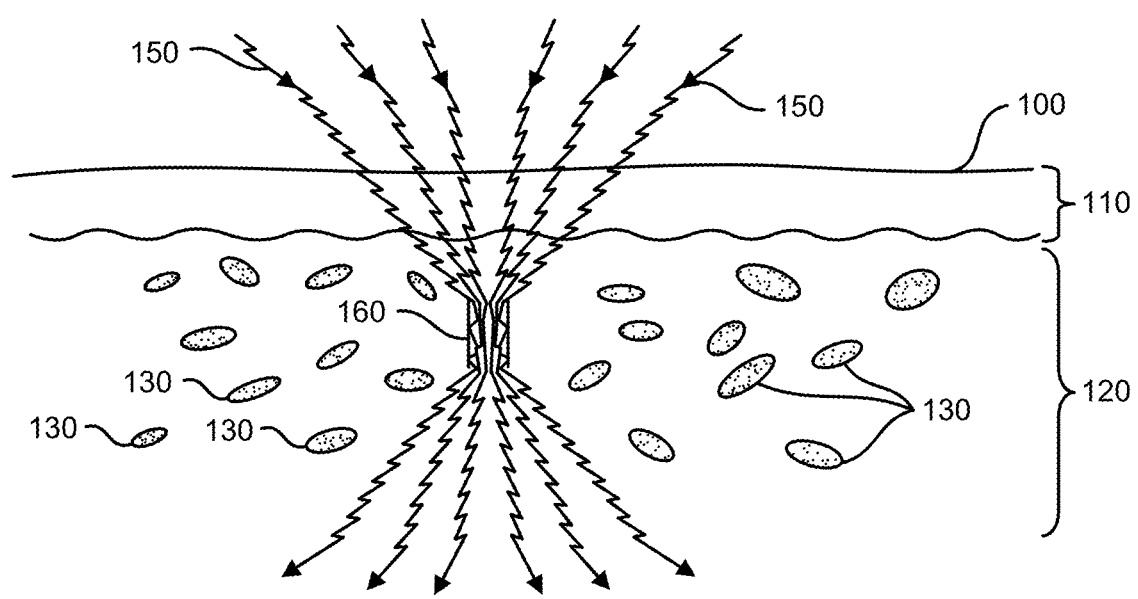
FIG. 2 is a schematic illustration of an electromagnetic radiation (EMR) beam focused into a pigmented region of a dermal layer in skin.

FIG. 2 is a schematic view of an illustration of a laser beam focused into a pigmented region of a dermal layer in a skin tissue. The skin tissue includes a skin surface 100 and an upper epidermal layer 110, or epidermis, which can be, e.g., about 30-120 µm thick in the facial region. The epidermis 110 can be slightly thicker in other parts of the body. For example, in general the thickness of the epidermis can range from about 30 µm (e.g., on the eyelids) to about 1500 µm (e.g., on the palm of the hand or soles of the feet). Such epidermis may be thinner or thicker than the examples above in certain conditions of the skin, for example psoriasis. The underlying dermal layer 120, or dermis, extends from below the epidermis 110 to the deeper subcutaneous fat layer (not shown). Skin exhibiting deep or dermal melasma can include a population of pigmented cells or regions 130 that contain excessive amounts of melanin. Electromagnetic radiation (EMR) 150 (e.g., a laser beam) can be focused into one or more focal regions 160 that can be located within the dermis 120, or the epidermis, 110. The EMR 150 can be provided at one or more appropriate wavelengths that can be absorbed by melanin. EMR wavelength(s) can be selected based on one or more criteria described below.

Properties of Treatment Radiation

Figures 3A, 3B:
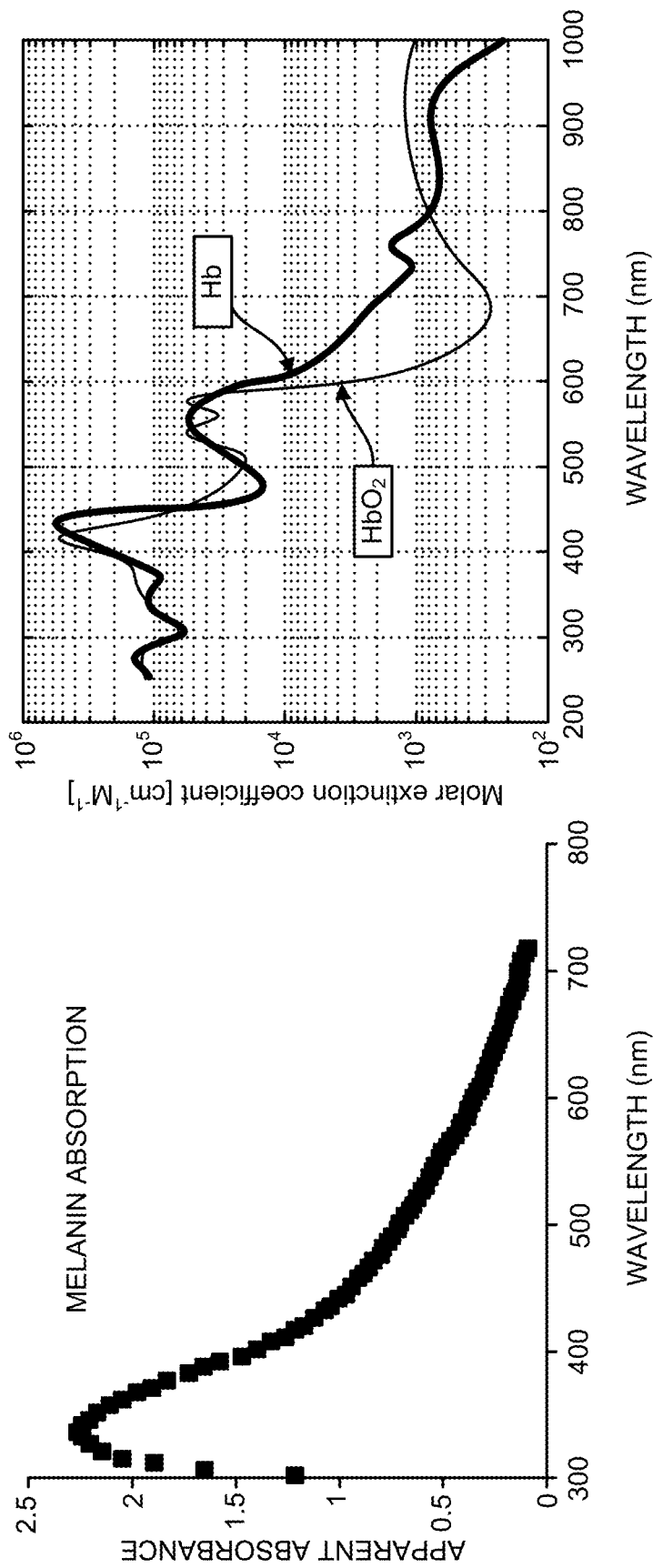
FIG. 3A is an exemplary absorbance spectrum graph for melanin.
FIG. 3B is an exemplary absorbance spectrum graph for hemoglobin.

Determination of desirable wavelength for treatment of certain skin conditions, such as pigmentary conditions and non-pigmentary conditions, can depend on, for example, the wavelength dependent absorption coefficient of the various competing chromophores (e.g., chromophore, hemoglobin, tattoo ink, etc.) present in the skin. FIG. 3A is an exemplary absorbance spectrum graph for melanin. The absorption of EMR by melanin is observed to reach a peak value at a wavelength of about 350 nm, and then decreases with increasing wavelength. Although absorption of the EMR by the melanin facilitates heating and/or disruption of the melanin-containing regions 130, a very high melanin absorbance can result in high absorption by pigment in the epidermis 110 and reduced penetration of the EMR into the dermis 120, or the epidermis 110. As illustrated in FIG. 3A, melanin absorption is relatively high at EMR wavelengths that are less than about 500 nm. Accordingly, wavelengths less than about 500 nm may not be suitable for penetrating sufficiently into the dermis 120 to heat and damage or disrupt pigmented regions 130 therein. Such enhanced absorption at smaller wavelengths can result in unwanted damage to the epidermis 110 and upper (superficial) portion of the dermis 120, with relatively little unabsorbed EMR passing through the tissue into the deeper portions of the dermis 120.

FIG. 3B is an exemplary absorbance spectrum graph for oxygenated or deoxygenated hemoglobin. Hemoglobin is present in blood vessels of skin tissue, and can be oxygenated ($HbO_2$) or deoxygenated (Hb). Each form of Hemoglobin may exhibit slightly different EMR absorption properties. As illustrated in FIG. 3B, exemplary absorption spectra for both Hb and $HbO_2$ indicate a high absorption coefficient for both Hb and $HbO_2$ at EMR wavelengths less than about 600 nm, with the absorbance decreasing significantly at higher wavelengths. Strong absorption of EMR directed into skin tissue by hemoglobin (Hb and/or $HbO_2$) can result in heating of the hemoglobin-containing blood vessels, resulting in unwanted damage to these vascular structures and less EMR available to be absorbed by the melanin when the desired treatment is a melanin-rich tissue or structure.

Figure 4:
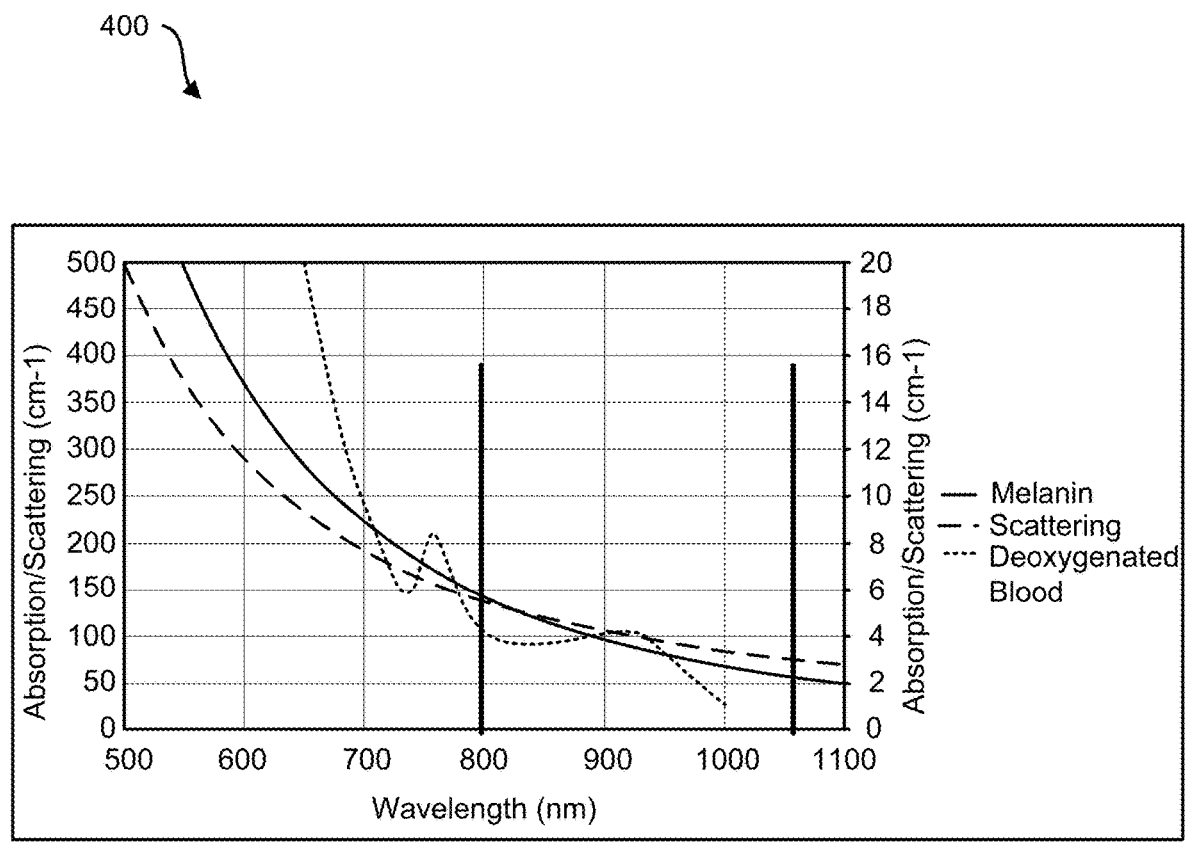
FIG. 4 illustrates a plot of the absorption coefficients of melanin and venous blood and scattering coefficients of light in skin versus wavelength.

The choice of an appropriate wavelength for EMR can also depend on wavelength dependent scattering profile of tissues interacting with the EMR. FIG. 4 illustrates a plot of the absorption coefficient of melanin and venous (deoxygenated) blood versus wavelength. FIG. 4 also illustrates a plot of the scattering coefficient of light in skin versus wavelength. Absorption in melanin decreases monotonically with wavelength. If melanin is the target of a pigmentary condition treatment, a wavelength having a high absorption in melanin is desirable. This would suggest that the shorter the wavelength of light, the more efficient the treatment. However, absorption by blood increases at wavelengths shorter than 800 nm, thereby increasing the risk of unintentional targeting of blood vessels. In addition, as the intended target can be located below the skin surface, the role of scattering by skin (e.g., dermal layer) can be significant. Scattering reduces the amount of light that reaches the intended target. The scattering coefficient decreases monotonically with increasing wavelength. Therefore, while a shorter wavelength can favor absorption by melanin, a longer wavelength can favor deeper penetration due to reduced scattering. Similarly, longer wavelengths are better for sparing blood vessels due to a lower absorption by blood at longer wavelengths.

With the above considerations in mind, wavelengths can range from about 400 nm to about 4000 nm, and more particularly about 500 nm to about 2500 nm, can be used for selectively targeting certain structures (e.g., melanin) in the dermis. In particular, wavelengths of about 800 nm and about 1064 nm can be useful for such treatments. The 800 nm wavelength can be attractive because laser diodes at this wavelength are less costly and readily available. However, 1064 nm can be particularly useful for targeting deeper lesions due to lower scattering at this wavelength. A wavelength of 1064 nm can also be more suitable for darker skin types in whom there is a large amount of epidermal melanin. In such individuals the higher absorption of lower wavelength EMR (e.g., about 800 nm) by melanin in the epidermis increases the chances of thermal injury to the skin. Hence, 1064 nm may be a more suitable wavelength of the treatment radiation for certain treatments for some individuals.

Various laser sources can be used for the generation of EMR. For example, Neodymium (Nd) containing laser sources are readily available that provide 1064 nm EMR. These laser sources can operate in a pulsed mode with repetition rates in a range of about 1 Hz to 100 KHz. Q-Switched Nd lasers sources may provide laser pulses having a pulse duration of less than one nanosecond. Other Nd laser sources may provide pulses having pulse durations more than one millisecond. An exemplary laser source providing 1060 nm wavelength EMR is a 20 W NuQ fiber laser from Nufern of East Granby, CT, USA. The 20 W NuQ fiber laser provides pulses having a pulse duration of about 100 ns at a repetition rate in the range between about 20 KHz and about 100 KHz. Another laser source, is an Nd: YAG Q-smart 850 from Quantel of Les Ulis, France. The Q-smart 850 provides pulses having a pulse energy up to about 850 mJ and a pulse duration of about 6 ns at a repetition rate of up to about 10 Hz.

The systems described herein can be configured to focus the EMR in a highly convergent beam. For example, the system can include a focusing or converging lens arrangement having a numerical aperture (NA) selected from about 0.3 to 1 (e.g., between about 0.5 and about 0.9). The correspondingly large convergence angle of the EMR can provide a high fluence and intensity in the focal region of the lens (which can be located within the dermis) with a lower fluence in the overlying tissue above the focal region. Such focal geometry can help reduce unwanted heating and thermal damage in the overlying tissue above the pigmented dermal regions. The exemplary optical arrangement can further include a collimating lens arrangement configured to direct EMR from the emitting arrangement onto the focusing lens arrangement.

The exemplary optical treatment systems can be configured to focus the EMR to a focal region having a width or spot size that is less than about 500 μm, for example, less than about 100 μm, or even less than about 50 μm, e.g., as small as about 1 μm. For example, the spot size can have ranges from about 1 μm to about 50 μm, from about 50 μm to about 100 μm, and from about 100 μm to about 500 μm. The spot size of the focal region can be determined, for example, in air. Such spot size can be selected as a balance between being small enough to provide a high fluence or intensity of EMR in the focal region (to effectively irradiate pigmented structures in the dermis), and being large enough to facilitate irradiation of large regions/volumes of the skin tissue in a reasonable treatment time.

A high NA optical system delivers different energy densities to different depths along an optical axis. For example, optical system having an NA of about 0.5 focuses a radiation to about a 2 μm diameter focal region width (i.e., waist) at focus. The focal region has a fluence (i.e., energy density) at focus of about 1 J/cm$^2$. Because of the high NA (i.e., fast) optical system, at a location just 10 μm out of focus the radiation has an energy density of 0.03 J/cm$^2$ or 3% the energy density at focus. The radiation a mere 30 μm out of focus has an energy density that is just 0.4% (0.004 J/cm$^2$) of the in-focus energy density. This precipitous change in energy density along the optical axis allows for depth selective tissue treatment to be possible; but it also requires the precise depth positioning of the focal region (e.g., to within tens of micrometers) within the target tissue.

The exemplary optical arrangement can also be configured to direct the focal region of the EMR onto a location within the dermal tissue that is at a depth below the skin surface, such as in the range from about 30 μm to about 2000 μm (e.g., between about 150 μm to about 500 μm). Such exemplary depth ranges can correspond to typical observed depths of pigmented regions in skin that exhibit dermal melasma or other targets of interest. This focal depth can correspond to a distance along the optical axis between a lower surface of the apparatus configured to contact the skin surface and the location of the focal region. Additionally, some embodiments can be configured for treating targets within the epidermis. For example, an optical arrangement may be configured to direct a focal region of the EMR to a location within the epidermis tissue (e.g., about 5 μm to about 2000 μm beneath the skin surface). Still other embodiments may be configured for treating a target deep in the dermis. For example, a tattoo artist typically calibrates his tattoo gun to penetrate the skin to a depth from about 1 mm to about 2 mm beneath the skin surface. Accordingly, in some embodiments an optical arrangement may be configured to direct a focal region of the EMR to a location within the dermis tissue in a range from about 0.4 mm to 2 mm beneath the skin surface.

It can be desirable that a treatment system for treatment of tissues be capable of identifying treatment areas in a target tissue. (e.g., by imaging: pigments, interface between dermal and epidermal layers in the target tissue, cell membranes, etc.). It can also be desirable to monitor/detect the interaction between the EMR and the target tissue (e.g., plasma generation in tissue). Additionally, based on the detection, the treatment system can modify the treatment process (e.g., by changing intensity, size/location of focal region in the target tissue, etc.). Below, various embodiments of treatment systems are described.

In order to further summarize, a table is presented below that includes parameter ranges for some exemplary embodiments.

|  | Min. | Nom. | Max. |
|---|---|---|---|
| Numerical Aperture | 0.01 | 0.5 | >1 |
| Depth of Focal Region (μm) | 0 | 250 | 5000 |
| Wavelength (nm) | 200 | 1060 | 20,000 |
| Rep. Rate (Hz) | 10 | 10,000 | 200,000 |
| Pulse Duration (ns) | $1 \times 10^{-6}$ | 100 | $1 \times 10^{5}$ |
| Pulse Energy (mJ) | 0.01 | 2 | 10000 |
| Average Power (W) | 0.001 | 20 | 1000 |
| $M^2$ | 1 | 1.5 | 3 |
| Laser Operation | Pulsed or Continuous Wave (CW) | | |
| Scan Width (mm) | 0.1 | 10 | 500 |
| Scan Rate (mm/S) | 0.1 | 250 | 5000 |
| No. Scan Layers (—) | 1 | 10 | 100 |
| Scan Pattern Form | Raster, Boustrophedon, Zig-Zag, Spiral, Random, etc. | | | where depth of focal region is a depth within the tissue (e.g., depth of focal region=0 can be at about a surface of the tissue) and $M^2$ is a parameter characterizing a quality of the EMR beam.

Feedback Detection and EMR-Based Treatment

Figure 5:
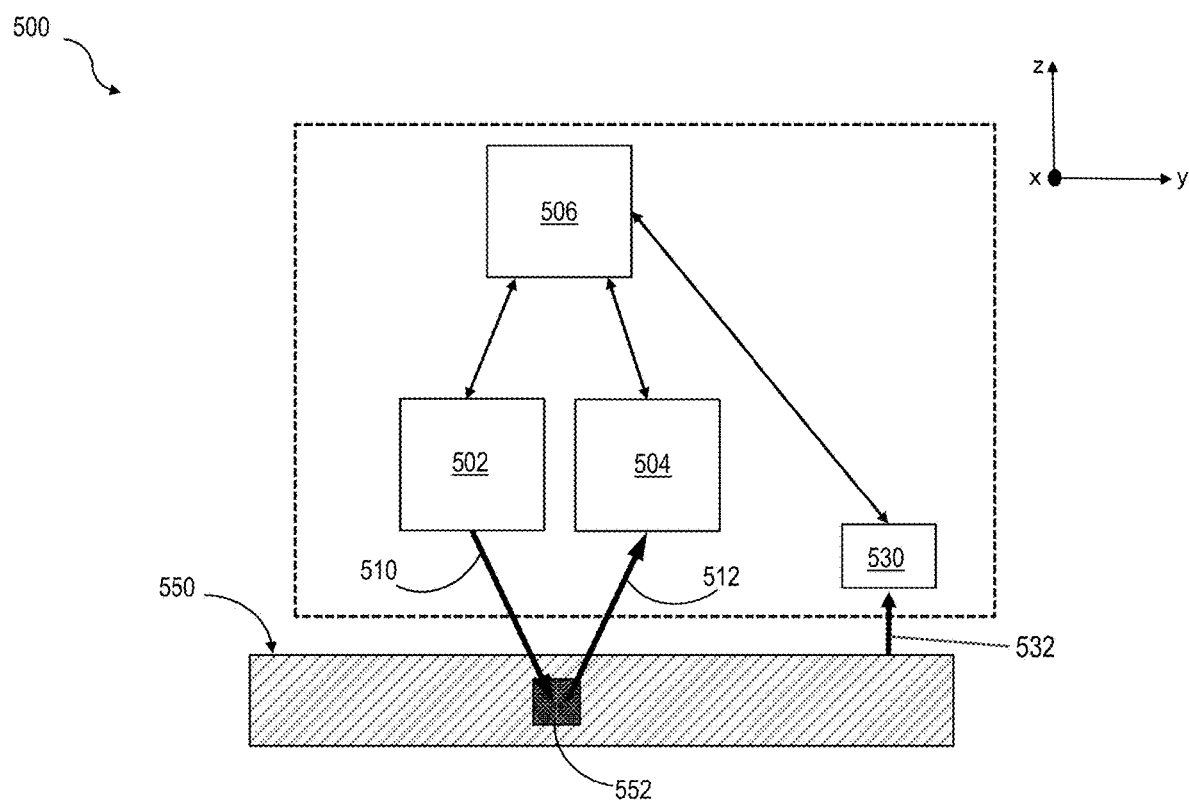
FIG. 5 is a schematic illustration of a treatment system, according to some embodiments.

FIG. 5 is a schematic illustration of a treatment system 500. The treatment system 500 can include an optical system 502, an EMR detection system 504 and a controller 506. The optical system 502 can include optical elements (e.g., one or more of mirrors, beam splitters, objectives, etc.) for directing EMR 510 generated by a source (e.g., a laser) to a focal region 552 of a target tissue 550. The EMR 510 can include an imaging radiation for imaging a dermal and/or epidermal layer of a target tissue 550 (e.g., skin). The EMR 510 can also include a treatment radiation for treatment of a region in the target tissue (e.g., region 522 of the target tissue 550). In some implementations, the EMR 510 can include only one of an imaging radiation and a treatment radiation in a given time period. For example, EMR 510 can include the treatment radiation for a first time duration and the imaging radiation for a second time duration. In other implementations, the EMR 510 can simultaneously include both the imaging and the treatment radiations in a given time period. According to some embodiments, the imaging radiation is of a wavelength generally equal to that of the treatment radiation; and, the imaging radiation has a power less than the treatment radiation. According to another embodiment, the imaging radiation is provided by an imaging radiation source other than the source providing the treatment radiation, and the imaging radiation has a wavelength different than the treatment radiation.

The EMR detection system 504 (e.g., photodiode, charged-coupled-device (CCD), spectrometer, photon multiplier tube, and the like) can detect signal radiation 512 generated by the target tissue 550 due to its interaction with EMR 510 and/or a portion of EMR 510 reflected by the target tissue. For example, EMR 510 having an intensity above a threshold value (e.g., treatment radiation) can generate a plasma in the target tissue. The plasma can produce the signal radiation 512, for example, due to its interaction with the EMR 510. The signal radiation 512 can be representative of properties of the plasma (e.g., the presence of plasma, the temperature of the plasma, the size of the plasma, components of the plasma, etc.)

In some implementations, EMR 510 having an intensity below the threshold value (e.g., imaging radiation) can interact with the target tissue without significantly perturbing the target tissue 550 (e.g., without damaging the target tissue 550, generating plasma in the target tissue 550, etc.) The signal radiation 512 generated from such an interaction can be used to image the target tissue 550 (e.g., portion of the target tissue 550 in the focal region of EMR 510). This signal radiation 512 can be used to detect pigments in the target tissue 550 (e.g., pigments located in the focal region of the target tissue). According to some embodiments, non-pigmented tissues are imaged. For example, as the imaging radiation (e.g., EMR 510) passes through cellular structures having different indices of refraction, the light is reflected as signal radiation 512.

The optical system 502 and the EMR detection system 504 can be communicatively coupled to the controller 506. The controller 506 can vary the operating parameters of the treatment system 500 (e.g., by controlling the operation of the optical system 502). For example, the controller 506 can move the focal region 552 of the EMR 510 in the target tissue 550. As discussed in greater detail below, this can be done, for example, by moving the optical system 502 relative to the target tissue 550, and/or by moving optical elements within the optical system 502 (e.g., by controlling actuators coupled to the optical elements) to vary the location of the focal region 552. The controller 506 can receive data characterizing optical detection of signal radiation 512 from the EMR detection system 504.

The controller 506 may control the properties of the EMR 510. For example, the controller 506 can instruct the source of EMR 510 (e.g., a laser source) to change the properties (e.g., intensity, repetition rate, energy per pulse, average power, etc.) of the EMR 510. In some implementations, the controller 506 can vary the optical properties (e.g., location of focal region, beam size, etc.) of the EMR 510 by placing/controlling an optical element (e.g., objective, diffractive optical element, etc.) in the path of the EMR. For example, the controller 506 can place an objective in the path of EMR 510 and/or move the objective along the path of the EMR 510 to vary the size of the focal region of the EMR 510.

The controller 506 can determine various characteristics of the target tissue 550 and/or interaction between the EMR 510 and the target tissue 550 (e.g., plasma generation in the target tissue 550) based on detection of the signal radiation 512 from the EMR detection system 504. In one implementation of the treatment system 500, the controller 506 can determine one or more of a distribution of a pigment, a topography of dermal-epidermal layer junction, etc., in the target tissue 550. Furthermore, the controller 506 can be configured to generate a map indicative of the detected distribution of one or more of the aforementioned properties of the target tissue 550. Determination of the such distributions and/or generation of the distribution map can be referred to herein as imaging.

In certain embodiments, the target tissue 550. For example, in a Cartesian coordinate system, the target can be scanned along one or more axes (e.g., along the x-axis, the y-axis, the z-axis, or combinations thereof). In alternative embodiments, scanning can be performed according to other coordinate systems (e.g., cylindrical coordinates, spherical coordinates, etc.). The scan can be performed using the imaging beam (e.g., EMR 510 having an intensity below a threshold value) and the signal radiation 512 corresponding to various regions in the target tissue 550 in the path of the imaging beam can be detected by the EMR detection system 504. Characteristics of the signal radiation 512 (e.g., intensity) can vary based on the pigments in the portions of the target tissue 550 that interact with the imaging beam (e.g., pigments in the focal region 552 of the imaging beam). The controller 506 can receive a signal from the EMR detection system 504 that can include data characterizing the detected characteristic (e.g., intensity) of the signal radiation 512. The controller 506 can analyze the received data (e.g., compare the received data with predetermined characteristic values of the detected signal radiation 512 in a database) to determine the presence/properties of pigments in the target tissue 550.

In some implementations, the controller 506 can determine a location of a portion of the target tissue 550 to be treated ("target treatment region") based on the signal radiation 512. For example, it may be desirable to treat a layer in a target tissue 550 (e.g., dermal layer in a skin tissue) located at a predetermined depth from the surface of the target tissue 550. The optical system 502 can be adjusted (e.g., by positioning the optical system 502 at a desirable distance from the surface of the target tissue 550) such that the focal region 552 is incident on the surface of the target tissue 550. This can be done, for example, by scanning the optical system 502 along the z-direction until the signal radiation 512 exhibits predetermined characteristics indicative of interaction between the EMR 510 and the surface of the target tissue 550. For example, an interface material (e.g., an optical slab, a gel, etc.) can be placed on the surface of the target tissue 550, and as the focal region 552 transitions from the target tissue 550 to the interface material, the characteristic of the signal radiation 512 can change. This can be indicative of the location of the focal region 552 of the EMR 510 at or near the surface of the tissue. Once the optical system 502 is positioned such that the focal region 552 of the EMR 510 is at or near the surface of the target tissue 550, the optical system 502 can be translated (e.g., along the z-direction) such that the focal region 552 is at the predetermined depth below the surface of the target tissue 550.

The controller 506 can vary the operating parameters of the treatment system 500 based on the signal received from the EMR detection system 504 including data characterizing the detected characteristic of the signal radiation 512. For example, some embodiments of the EMR detection system 504 can detect a depth of a dermis-epidermis (DE) junction in the target tissue 550, and the controller 506 can adjust a depth of the focal region 552 in response to the depth of the DE junction. In this manner, the DE junction can be employed as a reference for determining the depth of the focal region 552 within the dermis. Additionally, some embodiments of the EMR detection system 540 can quantify a proportion of melanin present in an epidermal layer of a skin (e.g., via use of a spectrophotometer). Based upon the proportion of melanin, the controller 506 can suggest one or more changes in laser parameters to a designated personnel (e.g., a clinician). According to some embodiments, changes in laser parameters can include at least one of varying energy per pulse inversely with the proportion of melanin detected, increasing focus angle with an increase in the proportion of melanin, and modifying depth of the focal region 552 based upon the proportion of melanin.

In some implementations, an acoustic sensor 530 (e.g., acoustic sensor) can be coupled to the target tissue 550, and the acoustic sensor 530 can detect characteristics of interaction between EMR 510 and target tissue 550. For example, an acoustic sensor can detect pressure waves 552 generated by the creation of plasma in the target tissue 550 (e.g., plasma generated in focal region 552). Examples of the acoustic sensor 530 can include: piezoelectric transducers, capacitive transducers, ultrasonic transducers, Fabry-Perot interferometer, and piezo electric films.

In one aspect, the pressure waves 532 can be shock waves, a sharp change in pressure propagating through a medium (e.g., air) at a velocity faster than the speed of sound in that medium. In another aspect, the pressure waves 532 can be acoustic waves that propagate through the medium at a velocity about equal to the speed of sound in that medium.

Photoacoustic imaging (optoacoustic imaging) is a biomedical imaging modality based on the photoacoustic effect. In photoacoustic imaging, non-ionizing laser pulses are delivered into biological tissues (when radio frequency pulses are used, the technology is referred to as thermoacoustic imaging). Some of the delivered energy will be absorbed and converted into heat, leading to transient thermoelastic expansion and thus wideband (i.e. MHz) ultrasonic emission.

Sensor measurement data from the acoustic sensor 530 can be transmitted to the controller 506. The controller 506 can use this data for validation of pigment detection via the signal radiation 512. According to some embodiments, treatment is confirmed through the detection of the shock waves 532. Presence and/or intensity of pressure waves 532 is correlated to a plasma being generated and a plasma mediated treatment being performed. Additionally, by mapping at which focal regions pressure waves 532 are detected, a comprehensive map of treated tissue may be created and documented.

Figure 6:
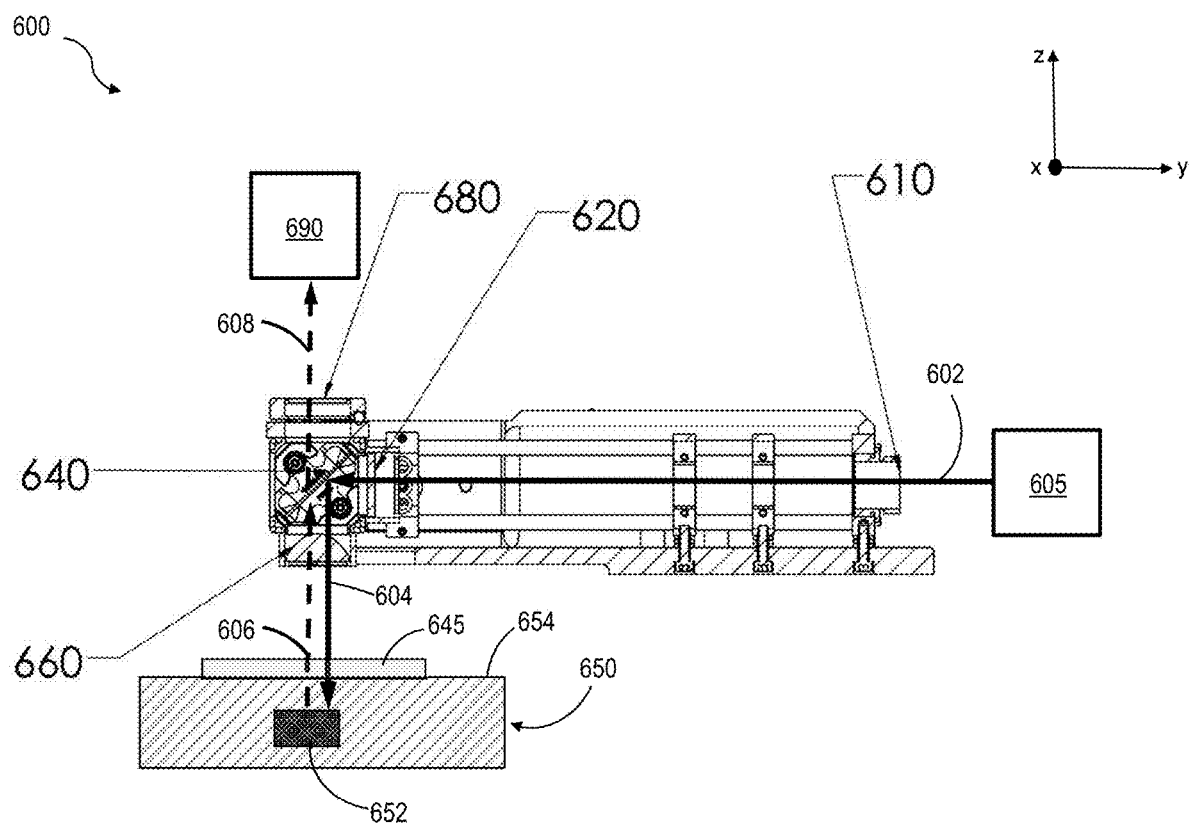
FIG. 6 is a schematic illustration of an optical system, according to some embodiments.

FIG. 6 is a diagram illustrating one exemplary embodiment of an optical system 600. The optical system 600 can guide the EMR beam 602 from an EMR source 605 to a target tissue 650. The EMR source 605 can be a laser (e.g., a Q-smart 450 laser from Quantel that has a 450 mJ pulse energy, a 6 nanosecond [nS] pulse duration, and a wavelength of 1064 nm or harmonic of 1064 nm). According to some embodiments, an EMR beam 602 can be introduced into the optical system 600 via an adapter 610. The adapter can be configured to secure an EMR source that generates the EMR beam 602 to an articulating arm e.g., arm 20 of mounting platform 12 of FIG. 1.

According to some embodiments, a diffractive optical element (DOE) 620 (e.g., beam splitters, multi-focus optics, etc.) can be placed in the path of the EMR beam 602. The DOE 620 can alter the properties of the EMR beam 602 and transmit a second EMR beam 604. For example, the DOE 620 can generate multiple sub-beams that are focused to different focal regions. Implementations and use DOE for treatment of target tissue are discussed in greater detail in U.S. Provisional Application 62/656,639, entitled "Diffractive Optics For EMR-Based Tissue Treatment," the entirety of which is incorporated by reference herein. The second EMR beam 604 (e.g., multiple sub-beams generated by the DOE 620) transmitted by the DOE 620 can be directed toward the target tissue 650 by a beam splitter 640 (e.g., a dichroic beam splitter). An example of a dichroic beam splitter can include a short pass dichroic mirror/beam splitter that has a cutoff wavelength of about 950 nm, a transmission band between about 420 nm to about 900 nm, and a reflection band between about 990 to about 1600 nm (Thorlabs PN DMSP950R). The second EMR beam 604 can be reflected by the beam splitter 640, and directed to an objective 660. The objective 660 can focus the EMR beam 604 to a focal region 652 in the target tissue 650 via the window 645. An example of the objective 662 is an Edmunds Optics PN 67-259 aspheric lens having a diameter of about 25 millimeters (mm), a numerical aperture (NA) of about 0.83, a near infrared (NIR) coating, and an effective focal length of about 15 mm. The window 645 can be used to hold the target tissue 650 in place.

In some implementations, the EMR beams 602, 604 can be expanded by a beam expander (not shown) placed in the path of the EMR beams 602, 604. Beam expansion can allow for a desirable NA value of the optical system 600. For example, a laser beam generated by a Q-smart 450 laser can have a beam diameter of about 6.5 mm and can require a beam expander that can expand the laser beam to twice the diameter. The expanded EMR beams 602, 604 can be focused using an approximately 15 mm EFL lens to focus the EMR beams 602, 604 with a sufficiently high NA (e.g., greater than 0.3).

The optical system 600 can be arranged such that the focal region 652 of the EMR beam 604 is located below the epidermis of the target tissue 650. This can be done, for example, by moving the optical system 600 relative to the target tissue 650 and/or moving the objective 660 along the beam path of the EMR 604. In one implementation, a position of the optical system 600/optical elements in the optical system 600 can be moved by a controller (e.g., controller 506). Placing the focal region 652 below the epidermis (e.g., below the dermis-epidermis (DE) junction) can reduce or substantially inhibit undesirable heat generation in the epidermis, which can lead to hyperpigmentation or hypopigmentation of the epidermis. This can also allow for targeting of regions in the dermis for heat and/or plasma generation.

Interaction between the second EMR beam 604 and the target tissue 650 can lead to the generation of signal radiation 606. As described above, signal radiation 606 can include radiation generated by plasma in the target tissue 650 ("tissue radiation"). Tissue radiation can have wavelengths that lie in the transmission band of the beam splitter 640. As a result, tissue radiation can be largely transmitted by the beam splitter 640. The signal radiation 606 can also include radiation having a wavelength similar to that of the second EMR beam 604 ("system radiation"). The wavelength of the system radiation can lie in the reflection band of the beam splitter 640. As a result, a small portion (e.g., 10%) of the system radiation is transmitted by the beam splitter 640.

Signal radiation 608 transmitted by the beam splitter 640 can include both tissue radiation and system radiation (or a portion thereof). Portions of the signal radiation 608 can be captured by EMR detector 690. The EMR detector 690 can communicate data characterizing the detection of signal radiation 608 (or a portion thereof) to a controller (e.g., controller 506). The controller can, for example, based on the detection (e.g., intensity of the transmitted signal radiation 608) alter the operation of the source 605 (e.g., switch off the source 605).

In one implementation, the optical system 600 can be used as a confocal microscope. This can be done, for example, by placing a second objective (not shown) upstream from the aperture 680. The aperture can reimage the signal radiation 606 by focusing at a focal plane that includes the aperture 680. The aperture 680 can filter (e.g., block) undesirable spatial frequencies of the signal radiation 608. This configuration can allow for filtering of signal radiation associated with different regions in the target tissue 650 (e.g., regions of target tissue at different depths relative to tissue surface 654). By changing the distance between the imaging aperture 680 and the target tissue 650 (e.g., by moving imaging aperture 680 along the path of signal radiation 608), different depths of the target tissue can be imaged. In some implementations, a controller (e.g., controller 506) can move the imaging aperture 680 by transmitting commands to an actuator. The controller 506 can analyze the detection data and determine the presence of plasma in the target tissue 650, distribution of pigments in the target tissue, and the like. The optical system 600 can be used to detect damage in the window 645. The damage to the window 645 can be caused by interaction between the second EMR beam 604 and the window 645 (e.g., when the intensity of the EMR beam is high, prolonged interaction with the EMR beam 604, etc.). Detection of damage in the window 645 can be implemented by determining a change in intensity in the signal radiation resulting from damage in the window 645. This can be done, for example, by positioning the focal region 652 incident on the window 645 (e.g., near the surface of the window 645, at the surface of the window 645, within the window 645) and detecting an intensity of the signal radiation 606 (e.g., by using a photodetector as the EMR detector 690). This intensity can be compared with an intensity previously measured when the focal region 652 is located on comparable location of an undamaged window 645. Based on this comparison damage in the window 645 can be determined.

Figure 7:
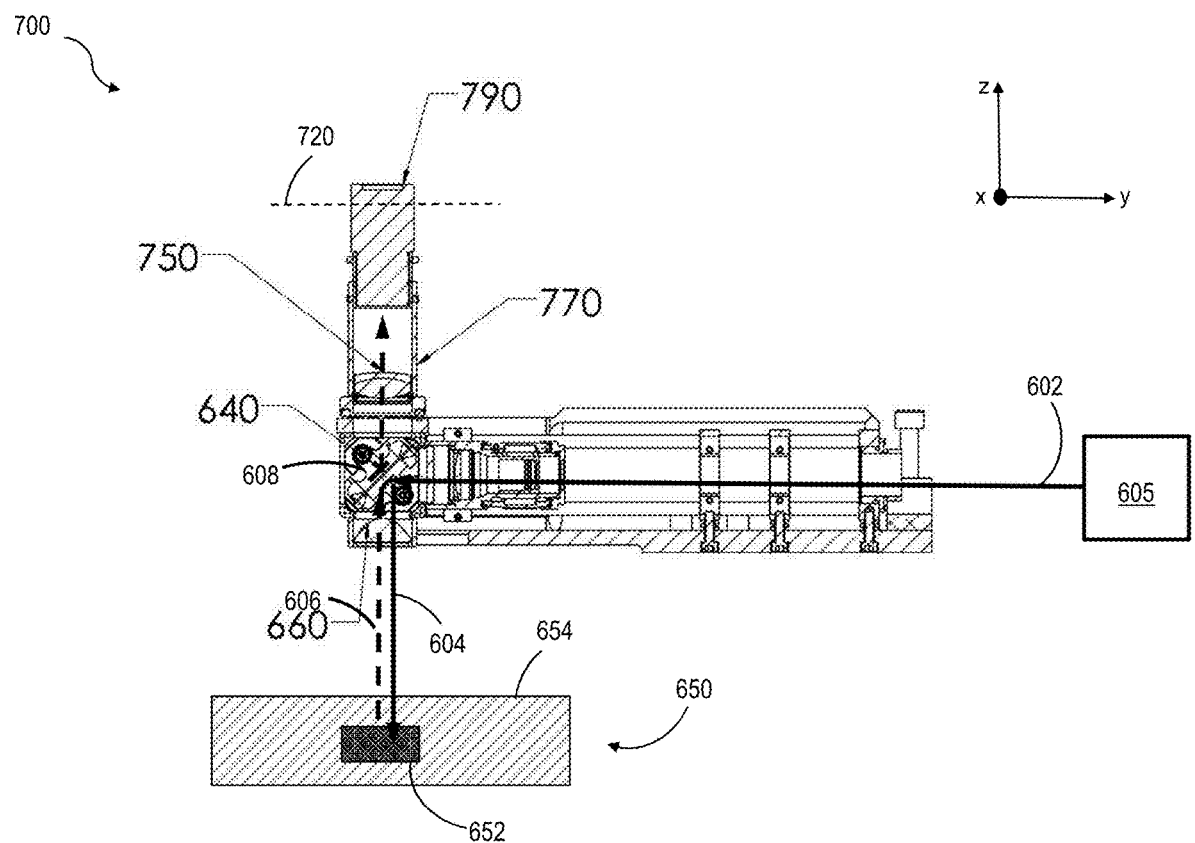
FIG. 7 is a schematic illustration of an optical system having a microscope attachment, according to some embodiments.

FIG. 7 is an illustration of an embodiment of an optical system 700. The optical system 700 can include a microscope attachment 770 having an eyepiece 790. The microscope attachment 770 can capture signal radiation 608 (or a portion thereof) transmitted by beam splitter 640. The signal radiation 608 can be reimaged by a tube lens 750 (e.g., Edmunds Optics PN 49-665 25 mm Diameter×50 mm EFL aspherized achromatic lens). The tube lens 750 can reimage the signal radiation 608 to a pupil plane 720 of the eyepiece 790 (e.g., Edmunds Optics PN 35-689 10X DIN eyepiece).

As described above, the signal radiation 608 can include both tissue radiation and system radiation. Due to difference in their wavelengths, images of the tissue radiation and system radiation are generated at different locations (e.g., at different planes). As a result, if the eyepiece 790 is positioned to capture the image generated by system radiation, it may not be able to accurately capture the image associated with tissue radiation. However, the eyepiece 790 can be calibrated to capture signal radiation having a different wavelength than the system radiation at the focal region of the system radiation. One way of calibrating is by using a material having an index of refraction similar to that of the target tissue 650 as a phantom (e.g., acrylic). Calibrating the eyepiece 790 can include focusing the second EMR beam 604 into the phantom (e.g., by objective 660) and inducing a breakdown (e.g., laser induced optical breakdown) at the focal region of the second EMR beam 604. This can be followed by impinging the second EMR radiation having a predetermined wavelength onto the phantom (e.g. at an oblique angle) and measuring the intensity of EMR radiation having the predetermined wavelength at the eyepiece 790. The axial location of the eyepiece 790 can be adjusted (e.g., along the z-axis) to maximize the intensity of detected radiation from the second EMR source. In certain embodiments, a sensor can be used instead of the eyepiece 790. Examples of sensors can include CMOS and CCD imagers. The sensor generates a digital image in response to radiation at a sensor plane. The digital image represents an image of the focal region 652.

Figure 8:
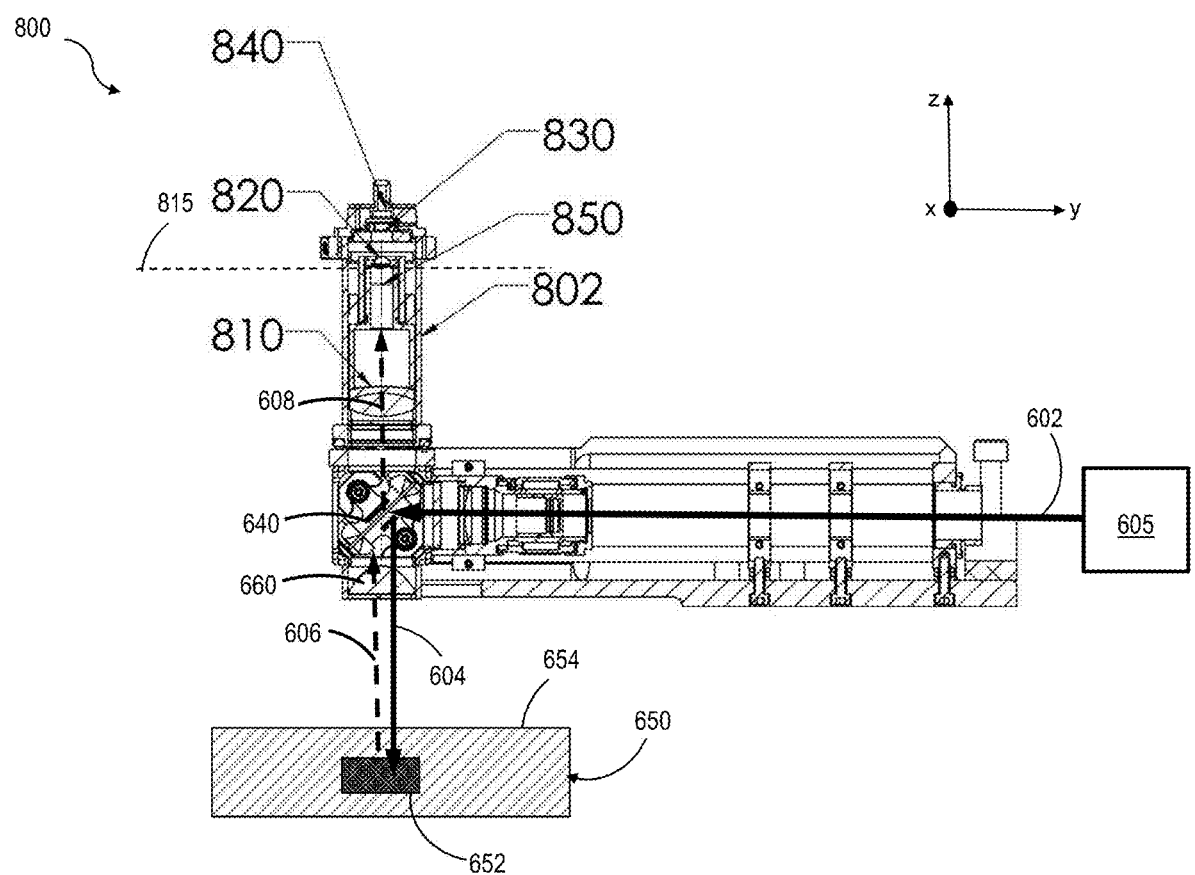
FIG. 8 is a schematic illustration of an optical system having a fiber coupler attachment, according to some embodiments.

FIG. 8 is an illustration of an embodiment of an optical system 800 having a fiber coupler attachment 802. The fiber coupler attachment 802 includes a lens tube 810 that can image light from the objective 660 and beam splitter 640 as described above. The lens tube 810 can focus the signal radiation 608 at a pupil plane 815 (e.g., plane parallel to the x-y axis and including the collimating lens 820). The focused signal radiation 608 can be collimated to a desirable size using the collimating lens 820, and can be directed to a coupling lens 830. The coupling lens 830 can focus the signal radiation 608 with an NA which is desirable for coupling into a fiber attached to a fiber connector 840. The fiber can be optically connected to one or more EMR detectors (e.g., detector 504). According to some embodiments, the coupler attachment 802 can further include an imaging aperture 850 located at the pupil plane 815. The aperture can filter portions of the signal radiation 608 that are not emanating from the focal region 652. According to some embodiments, a detection instrument (e.g., photodiode, spectrometer, etc.) may be placed directly after the imaging aperture 850 without a fiber optic or related optics. Calibration of the imaging aperture 850 relative the lens tube 810 may be achieved in a process similar to that described above in reference to calibration of the eyepiece 790.

Feedback detection can be used in conjunction with EMR-based treatment in many ways. Exemplary applications are described below to demonstrate some ways feedback informed EMR-treatment may be practiced. Broadly speaking, the examples described below may be categorized into three species of feedback informed EMR-treatment. These three species encompass examples that 1.) detect plasma; 2.) reference a focal region position; and 3.) image a tissue. These three categories of use are not intended to be an exhaustive (or mutually exclusive) list of applications for feedback informed EMR-based treatment.

Plasma Feedback Examples

Some treatments include the formation of a plasma during treatment (e.g., thermionic plasma or optical breakdown). In some embodiments, properties of a detected plasma are indicative of potential effectiveness of treatment. For example, in treating a dermal pigment condition a focal region is located deep within the skin, so that it will coincide with dermal pigment as it is scanned during treatment. As the focal region is scanned over the skin, a laser source delivers a pulsed laser, such that where the focal region and dermal pigment coincide thermionic plasma is formed. The formation of the thermionic plasma is indicative that 1.) a pigment is present within the skin, 2.) the pigment at a moment of plasma formation is collocated with the focal region (e.g., X-Y coordinates, as well as depth), and 3.) the pigment at this location has been treated (e.g., the pigment has been disrupted).

In other circumstances, plasma formation can indicate a need for system maintenance. For example, some systems include a window that is placed in contact with a tissue undergoing treatment. The window can serve many functions including: contact cooling, stabilizing the tissue, providing a depth reference for the tissue, and evacuating blood or other fluids from the tissue through pressure. Radiation (e.g., laser beam) also passes through the window for treatment of a treatment region below. In some cases, the radiation can cause breakdown within the window or at a surface of the window, resulting in plasma generation and window etching. If the system continues to deliver radiation after plasma generation at the window, burning or thermal damage of the tissue directly in contact with the window often results.

Figure 9:
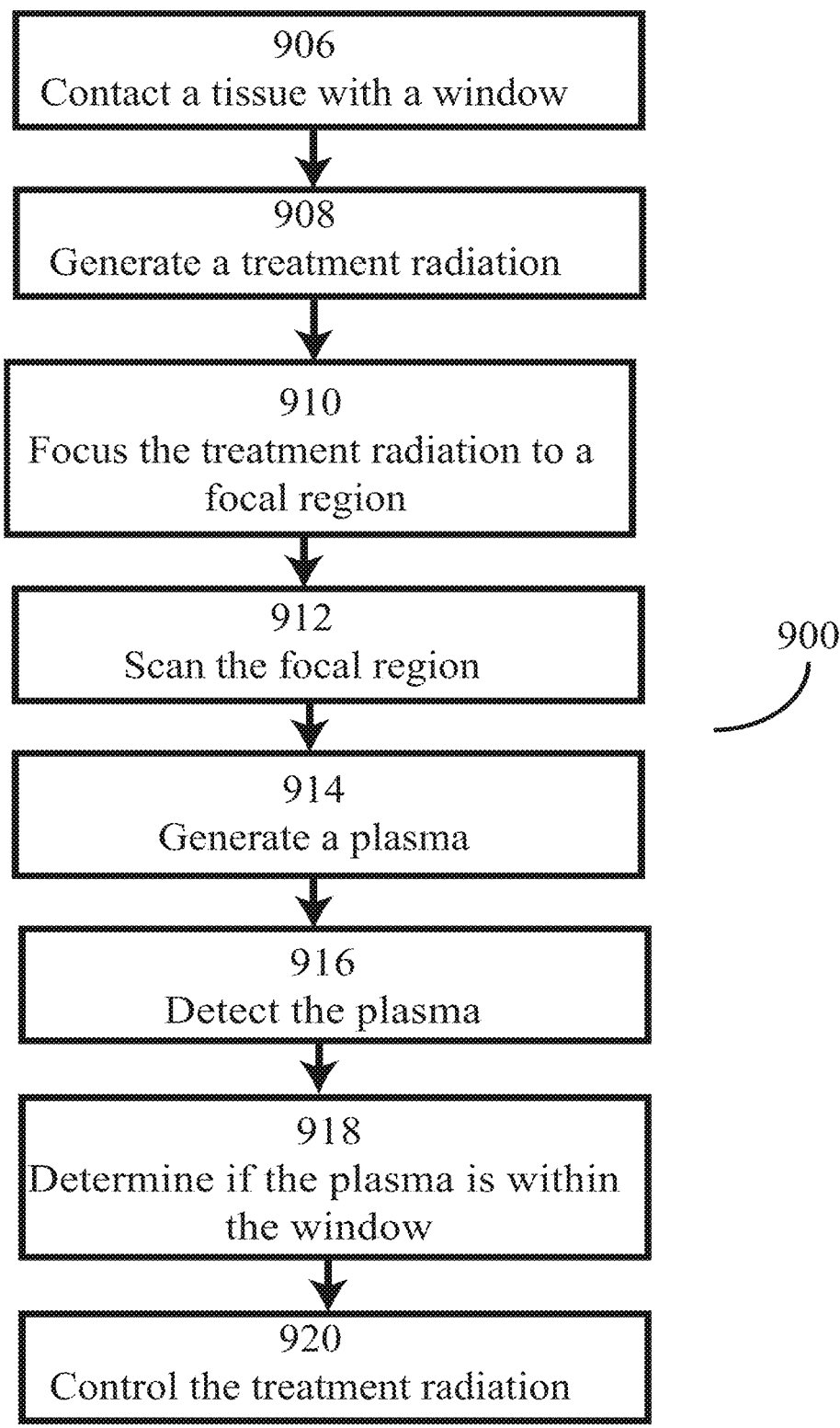
FIG. 9 illustrates a flow chart for a plasma detection method, according to some embodiments.

FIG. 9 illustrates a flow chart for a plasma detection method 900 during radiation-based tissue treatment, according to some embodiments. First, a surface of a tissue is contacted using a window 906. The window contacts an outer surface of the tissue. The window is configured to transmit the transmit a treatment radiation. Typically, the window provides a datum surface, such that placing the surface of the tissue in contact with the window effectively references the outer surface of the tissue. According to some embodiments, the window provides additional functions including, but not limited to, preventing movement of the tissue during treatment, contact cooling of the tissue being treated, and evacuation of blood (or other competing chromophores) within the tissue through compression.

A treatment radiation is then generated 908. The treatment radiation is typically generated by a radiation source. The treatment radiation is configured to produce an effect in the tissue, which can result in an improved or desired change in appearance. In certain embodiments, tissue effects can be cosmetic. In other embodiments, tissue effects can be therapeutic. According to some embodiments, the tissue effect includes generation of selective thermionic plasma in presence of a chromophore. Parameter selection for a treatment radiation is dependent on the treatment being performed as well as the tissue type and individual patient. Details related to treatment radiation generation 900 and relevant parameter selection to produce an effect in tissue (e.g., a cosmetic effect) are described in detail above.

The treatment radiation is focused to a focal region 910. Typically, the treatment radiation is focused 910 by a focus optic. According to some embodiments, the focal region has a width that is smaller than about 1 mm, about 0.1 mm, about 0.01 mm, or about 0.001 mm. The focal region may be positioned at a first region. In some embodiments, the first region is located within the tissue specifically at a location to be treated. In some cases, the first region may be intentionally or unintentionally located outside of the tissue, for example within the window that is in contact with the tissue.

The focal region is scanned 912, typically by a scanning system (e.g., scanner). Examples of scanning include: tipping/tilting the focal region, rotating the focal region, and translating the focal region. Further description of relevant scanning means is described in U.S. patent application Ser. No. 16/219,809 "Electromagnetic Radiation Beam Scanning System and Method," to Dresser et al., incorporated herein by reference in its entirety. According to some embodiments, the treatment radiation is pulsed, such that approximately no treatment radiation is delivered as the focal region is scanned (e.g., moved for the first region to a second region). The focal region may also be scanned continuously. In this case, timing of treatment radiation pulses and scan parameters control the locations for the first region and the second region.

A plasma is generated by the treatment radiation 914. The plasma is typically generated within or near the focal region, because fluence is at a maximum within the focal region. According to some embodiments, plasma is generated 914 selectively a pigmented region through thermionic-plasma generation. Alternatively, the plasma may be generated 914 through non-selective laser induced optical breakdown.

The plasma is then detected 916. A detector typically detects a signal radiation emanating from the plasma 916. Examples of signal radiation detection include: optical detection, acoustic detection, spectroscopic detection of laser induced breakdown (e.g., laser induced breakdown spectroscopy), plasma generated shockwave (PGSW) detection, plasma luminescence detection, plasma (plume) shielding detection, and plasma photography. In some embodiments, properties of the plasma are determined based upon the detection of the plasma 916. Examples of properties of the plasma include: presence of plasma, intensity of plasma, spectral content of plasma, and position of plasma. According to some embodiments, a property of the signal radiation is recorded and stored, for example by the controller.

In some embodiments, it is determined if the plasma is located at least partially within the window 918, based upon the detected plasma. For example, in some embodiments an optical signal radiation including a spectral component known to be representative of a material in the window and not in the tissue may be detected indicating that the plasma is partially within the window. In another version, intensity of an optical signal radiation may reach exceed a known threshold implying that the plasma is at least partially within the window.

Parameters related to the treatment radiation are controlled 920 based in part upon the detected plasma (e.g., the determination 918 that the plasma is or is not partially located in the window). Examples of parameters related to the treatment radiation can include, but are not limited to, an energy per pulse, a repetition rate, a position of the focal region, or a size of the focal region. These treatment radiation parameters can be employed alone or in combination with one another or other treatment radiation parameters without limit. For example, the determination that the plasma is partially located in the window may be used as a triggering event to cease the treatment radiation.

In some embodiments, a map is generated that can include a matrix of properties mapped to location, for example by the controller. As an example, the map may include: a first property of a first signal radiation emanating from a first plasma at a first location can be mapped to a coordinate for the first location, and a second property of a second signal radiation emanating from a second plasma at second location mapped to a coordinate for the second location. An exemplary map can include a four-dimensional matrix having three orthogonal axes related to the position of the focal region, and a fourth axes related to one or more properties of the plasma. In some versions, the map may be used as an indication of individual treatment effectiveness. A system suitable for performing the above described plasma detection method is described in detail below Referring to FIG. 10, schematics are shown for a plasma detection and treatment system 1000, according to some embodiments. In some embodiments, a window 1006 is configured to contact a surface of a tissue 1008, for example an outer surface of the tissue 1008. The window 1006 includes an optical material configured to transmit the EMR beam, for example: glass, a transparent polymer (e.g., polycarbonate), quartz, sapphire, diamond, zinc-selenide, or zinc-sulfide.

The imaging and treatment system 1000 includes a focus optic 1010. The focus optic 1010 (e.g., objective) is configured to focus an electromagnetic radiation (EMR) beam 1011 and generate a plasma 1012 within the tissue 1008. The plasma may be generated selectively at a chromophore within the tissue 1008 through thermionic generation. In other embodiments, the plasma 1012 is non-selectively generated through optical breakdown. The EMR beam 1011 may be generated using a radiation source (not shown). The EMR beam 1011 may include any of collimated or non-collimated light and coherent and non-coherent light.

A detector 1014 is configured to detect the plasma 1012. Examples of plasma detectors 1014 include: photosensors, for example photodiodes and image sensors; acoustic sensors, for examples surface acoustic wave sensors, piezoelectric films, vibrometers, and etalons; and, more specialized detectors, for example spectrometers, spectrophotometers, and plasma luminance (or shielding) optical probes.

In the shown embodiment, the plasma detector includes a photodetector (e.g., a photodiode), which senses visible light 1016 (e.g., signal radiation) emanating from the plasma 1012. According to some embodiments, a tube lens 1018 is used in conjunction with the focus optic 1010 to direct and focus the visible light 1016 incident the detector 1014. The detector 1014 is communicative with a controller 1015, such that data associated with the detected plasma is input to the controller 1015.

Figure 10:
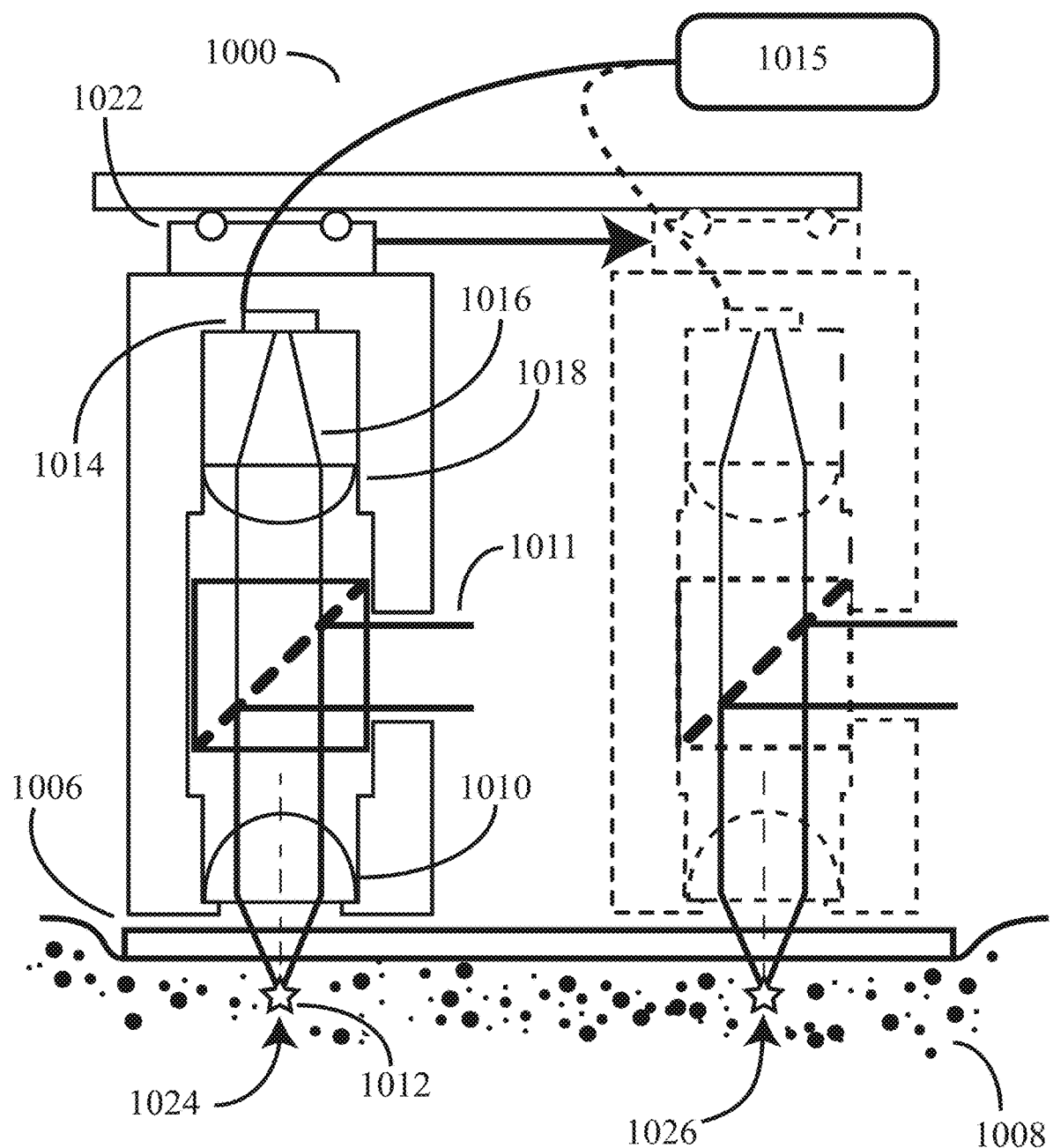
FIG. 10 illustrates a schematic of a plasma detection system, according to some embodiments.

A scanner 1022 is configured to scan a focal region of the EMR beam 1011. The scanner typically scans the focal region in at least one dimension. And, in some embodiments, the scanner 1022 scans the focal region in all three dimensions. Referring to FIG. 10, the scanner 1022 is shown scanning the focal region left to right from a first region 1024 to a second region 1026 of the tissue 1008.

As the scanner 1022 scans the focal region, the EMR beam 1011 can be pulsed, causing a first plasma to be generated at the first region 1024 and then a second plasma to be generated at the second region 1026. The first plasma and the second plasma are both detected by the detector 1014. In some embodiments, data associated with the first detected plasma and the second detected plasma are input to the controller 1015. In some embodiments, the data associated with one or more plasma events are used by the controller to control parameters associated with at least one of the EMR beam 1011 and the scanner 1022.

According to some embodiments, the controller 1015 is configured to control the EMR beam 1011 (e.g., terminate the EMR beam 1011) based upon a determination if the plasma 1012 is located at least partially within the window 1008. In some versions, the controller 1015 determines if the plasma 1012 is at least partially located within the window 1006 based upon an intensity of the signal radiation 1016 emanating from the plasma 1012. The intensity of the signal radiation 1016 may be detected using a photosensor (e.g., photodiode). According to another version, the controller 1015 determines if the plasma 1012 is at least partially located within the window 1006 based upon a spectral component of the signal radiation 1016. For example, according to some embodiments the window 1006 can include sapphire, which includes aluminum. A spectra peak corresponding to aluminum is centered at about 396 nm. Skin does not normally contain aluminum. Therefore, if the signal radiation (taken a precise time after a laser pulse [e.g., 10 us]) includes a spectral peak centered at about 396 nm it is likely that the plasma 1012 is at least partially located within the window 1006. According to some embodiments, a spectral filter (e.g., notch filter) and a photosensor is used to detect the spectral content of the signal radiation. According to other embodiments, a spectrometer or spectrophotometer is used to detect the spectral content of the signal radiation.

The controller 1015 may be configured to record one or more detected properties of the plasma 1012. In some embodiments, the controller 1015 is configured to record a matrix (or map) of detected properties of the plasma 1012. For example, the controller 1015 may be configured to: record a first property of a first signal radiation emanating from a first plasma 1012 at a first location 1024; map the first property to a coordinate for the first location 1024; record a second property of a second signal radiation emanating from a second plasma at a second location 1026; and map the second property to a coordinate for the second location 1026.

Individual embodiments are provided below to further explain plasma detection in an EMR treatment device.

Plasma Feedback Example 1

A first plasma feedback example describes an in vitro study, which quantifies changes in relative plasma light intensity demonstrating plasma presence. The in vitro study is performed with skin from a female Yucatan pig, selected for its dark skin. A 10 W Nufern fiber laser having a wavelength of about 1060 nm is used as a laser source in the in vitro study.

Figure 11A:
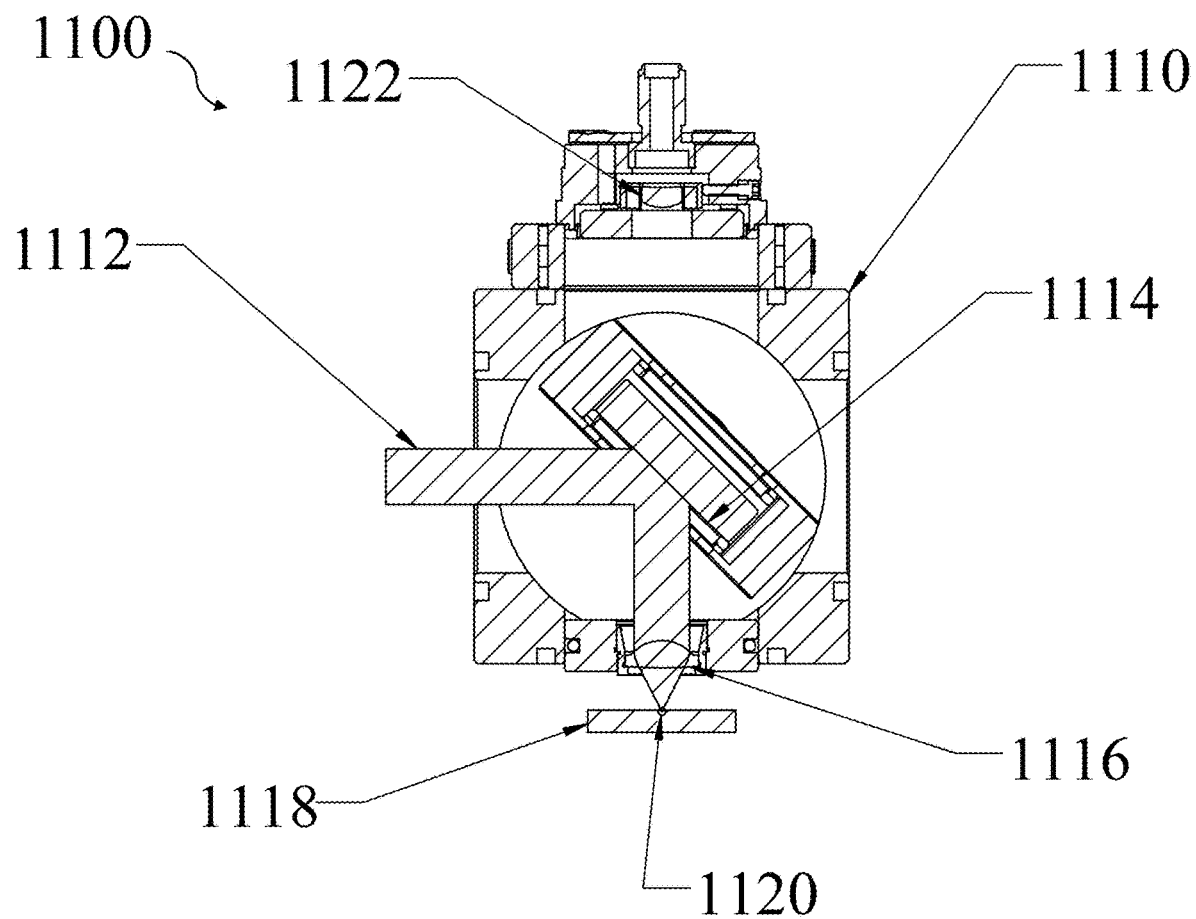
FIG. 11A is a schematic illustration of a treatment optical system, according to some embodiments.

FIG. 11A is a schematic illustration of a treatment optical system 1100 used in the in vitro study. The treatment optical system 1100 includes a beam combiner 1110 configured to receive a collimated laser beam 1112. The beam combiner 1110 includes a reflector 1114 that reflects the incident laser beam 1112. The reflector 1114 is selected to reflect light having a predetermined wavelength range. In the current in vitro study, the laser beam 1112 has a wavelength of 1060 nm, and the reflector is a Thorlabs NB1-K14, which is 99.5% reflective over a wavelengths range of 1047 to 1064 nm. The reflected laser beam 1112 is imaged and focused by a focus optic 1116. The focus optic 1116 used in the in vitro study is a Thorlabs C240TME-C, which is an aspheric lens capable of diffraction limited performance having an NA of 0.5 and an effective focal length of 8 mm. The laser beam 1112 is focused to a waist (e.g., focal volume) in a skin sample 1118. At the waist of the laser beam 1112, a plasma plume 1120 is generated within the skin sample 1118. Radiation 1124 generated from the plasma plume 1120 is imaged by the focus optic 1116 and is transmitted through the reflector 1114. After transmission through the reflector 1114, the radiation 1124 is imaged into a first end of a fiber optic (not shown) by a fiber coupler, 1122. The fiber coupler used in the in vitro study is a Thorlabs PAF-SMA-7-A. A second end of the fiber optic is coupled to a spectrometer (not shown) which is an Ocean Optics HR2000+ ES. In another implementation of the in vitro study, a notch filter (not shown) is disposed between the reflector 1114 and the fiber coupler 1122 to block portions of the radiation 1124 having a wavelength similar to that of the laser beam 1112 from entering the fiber optic. The skin sample, 1118, is mounted on motorized staging 1130. A working distance between the skin sample 1118, and the focus optic 1116, is maintained to control a depth of the waist of the laser beam 1112 within the skin sample 1118.

In another implementation of the in vitro study, a skin sample 1118 having a melanin tattoo is placed on the motorized stage 1130 such that the waist of the laser beam 1112 is located about 0.2 mm deep into the sample 1118. The melanin pigment used in the melanin tattoo is from Cuttlefish ink (e.g., sepia ink). The melanin tattoo is located approximately between a quarter of a millimeter and a millimeter deep in the dermis of the skin sample. Depth of the tattoo pigment within the skin is verified by viewing a histological sample of the skin.

Figure 11B:
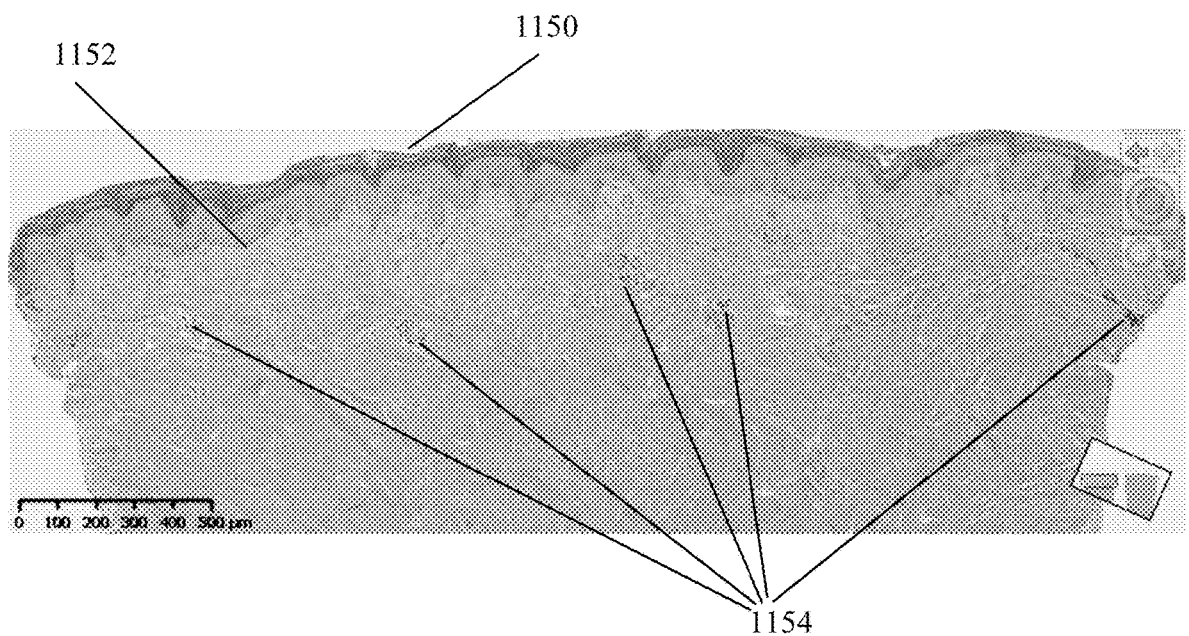
FIG. 11B illustrates the histology of a section of a skin sample having melanin tattoo.

FIG. 11B illustrates a scan of a histological sample of the skin sample 1118 having a melanin tattoo. The skin surface 1150 is shown at the top of the histology. An epidermis-dermis junction 1152 demarcates the epidermis and dermis layers of the skin. Melanin globules 1154 present in the dermis constitute the melanin tattoo. The laser is operated at 20 KHz, 100 ns pulse duration, and 0.5 mJ/pulse. The sample is scanned during laser irradiation at a rate of 100 mm/s. The spectrometer is adjusted to capture light over a 5000 ms period and trigger the capturing in response to the laser irradiation.

Figure 12:
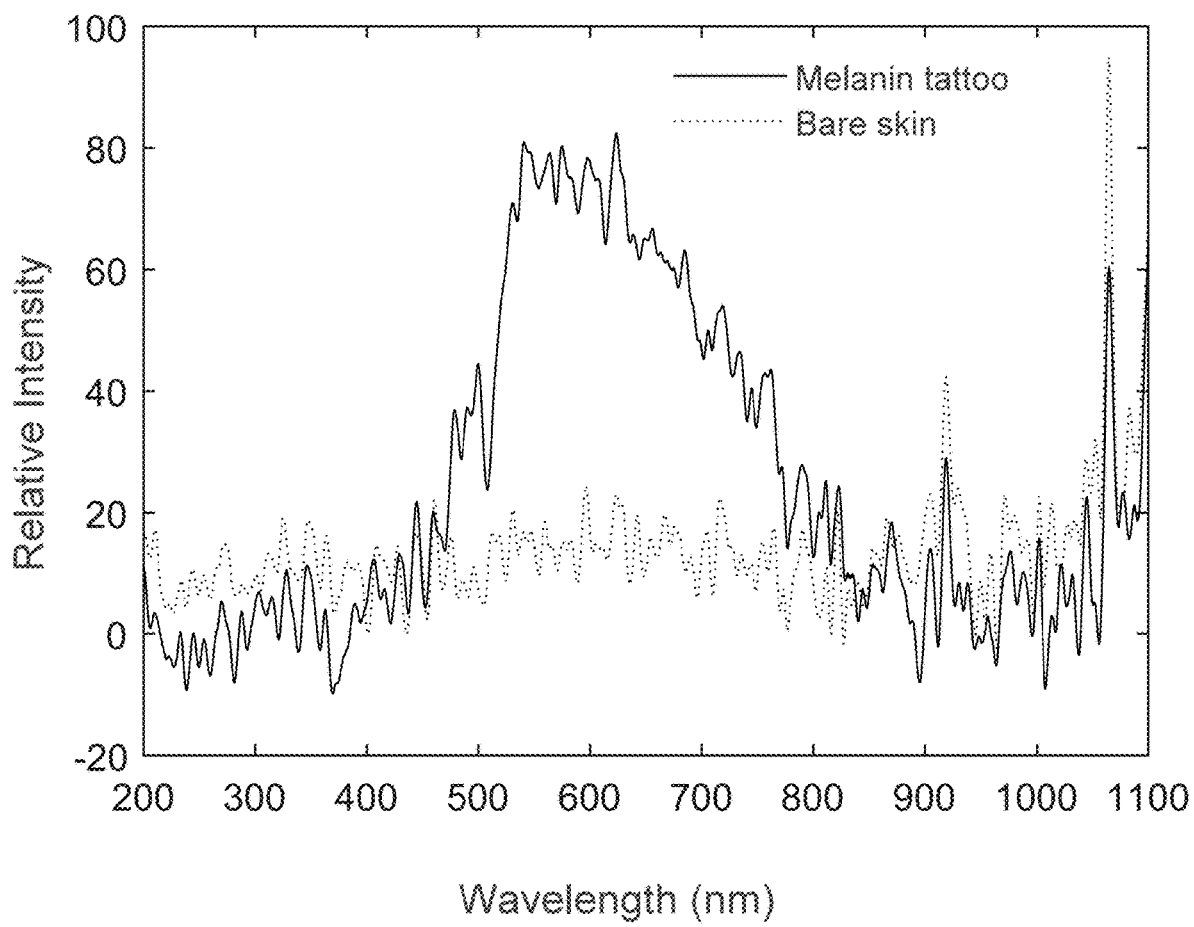
FIG. 12 illustrates spectra associated with radiation from plasma generated in melanin tattoo and radiation from no-plasma generated in bare skin, according to some embodiments.

FIG. 12 illustrates spectra associated with radiation from melanin tattoo and bare skin. The horizontal axis represents the wavelength of the radiation from the sample skin 1118 and the vertical axis represents the relative intensity of the radiation. FIG. 12 illustrates a melanin tattoo spectrum (e.g., centered at about 600 nm) and a bare skin spectrum generated when the skin 1118 is irradiated with a laser beam 1112 (e.g., having a spectrum centered at about 1060 nm). The melanin tattoo spectrum shows a measurement taken during irradiation of the sample at the location of the melanin tattoo (e.g., when waist/focal volume of the input laser beam 1112 irradiates portions of the skin having melanin tattoo). The bare skin spectrum shows a measurement taken during irradiation of a region of the sample skin 1118 that does not include the melanin tattoo. The melanin tattoo spectrum shows a presence of a broad-spectrum light that includes radiation in the visible spectrum (e.g., between 400 nm and 800 nm). The broad-spectrum light indicates plasma formation during irradiation of the melanin tattoo. The bare skin spectrum has generally no or very small visible spectrum component. The lack of visible light component in the bare skin spectrum indicates that generally no plasma was formed during irradiation of the bare skin.

Another skin sample 1118 having a carbon tattoo (e.g., India ink) is placed on the motorized stage 1130 beneath the focus optic 1116 such that the focus waist of the laser beam is located about 0.2 mm below the surface of the skin sample 1118. The Carbon tattoo is located approximately between a quarter of a millimeter and a millimeter deep in the dermis of the skin sample 1118. The laser is operated at 20 KHz, 100 ns pulse duration, and 0.5 mJ/pulse. The sample is scanned during laser irradiation at a rate of 100 mm/s. The spectrometer is adjusted to capture light over a 5000 ms period and trigger capturing in response to the laser irradiation.

Figure 13:
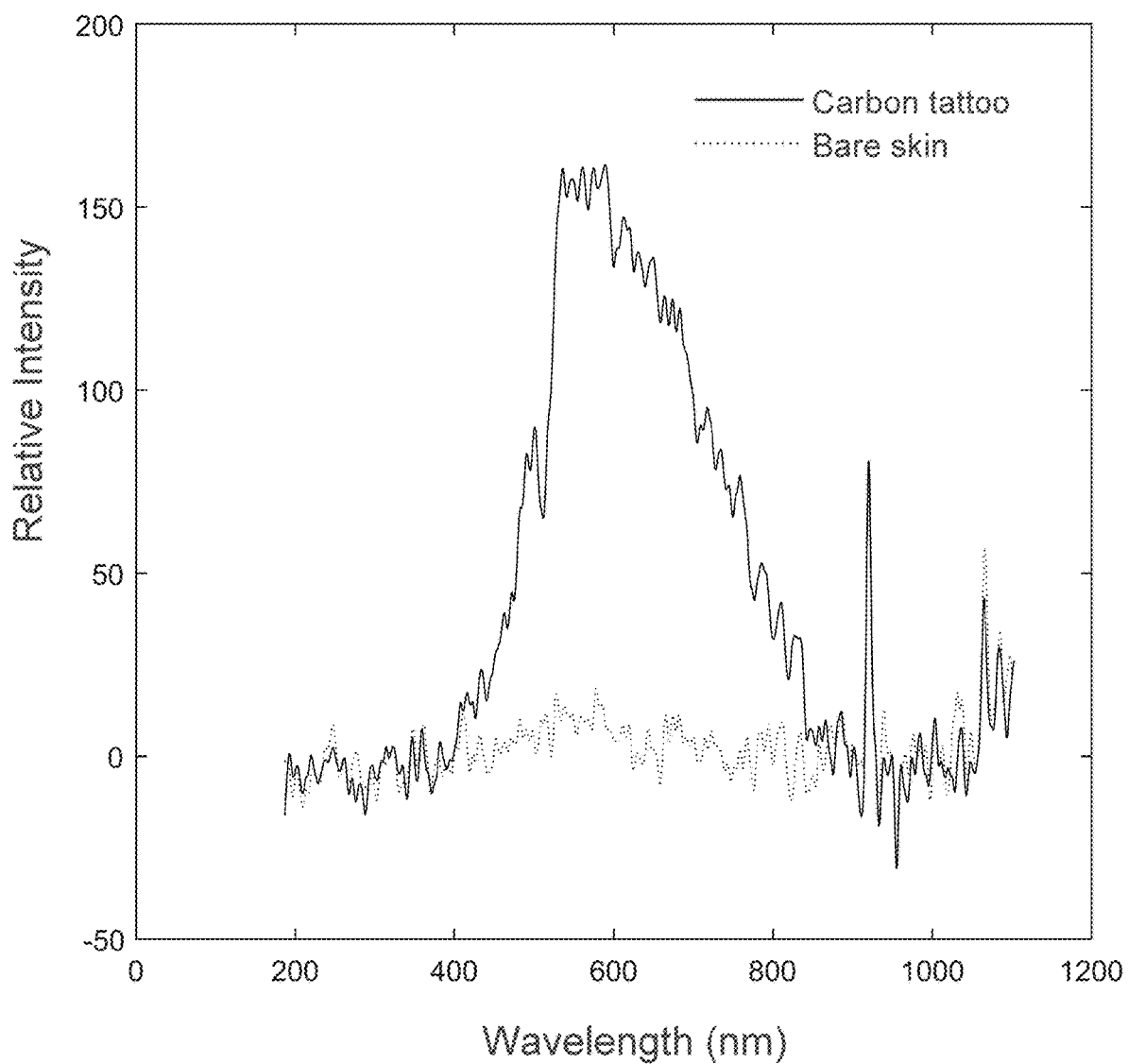
FIG. 13 illustrates spectra associated with radiation from plasma generated in carbon tattoo and radiation from no-plasma generated in bare skin, according to some embodiments.

FIG. 13 illustrates spectra associated with radiation from carbon tattoo and bare skin. The horizontal axis represents the wavelength of the radiation from the sample skin 1118 and the vertical axis represents the relative intensity of the radiation. FIG. 13 illustrates a carbon tattoo spectrum and a bare skin spectrum generated when the skin 1118 is irradiated with laser beam 1112. The carbon tattoo spectrum shows a measurement taken during irradiation of the sample at the location of the carbon tattoo (e.g., when waist/focal volume of the input laser beam 1112 irradiates portions of the skin having carbon tattoo). The bare skin spectrum shows a measurement taken during irradiation of a region of the sample skin 1118 that does not include the carbon tattoo. The carbon tattoo spectrum shows a presence of a broad-spectrum light that includes radiation in the visible spectrum (e.g., between 400 nm and 800 nm). The broad-spectrum light indicates plasma formation during irradiation of the carbon tattoo. The bare skin spectrum has a generally no visible spectrum component. The lack of light indicates that generally no plasma was formed during irradiation of the bare skin.

It should be noted that the broad spectrum captured in the above experiments results from the generation of plasma at many locations at a rate of 20 KHz which is the repetition rate of the laser beam 1112. An integration time of the spectrometer is set at 1 ms or greater. This allows for characterization of the spectral information of plasma generated over multiple pulses of the laser beam 1112. After the interaction between an incident laser pulse (of laser beam 1112) and the plasma, the plasma begins to cool and its electrons drop an energy level thereby emitting light over narrow spectral bands. As the above spectrometer measurements were integrated over multiple pulses it should be understood that these narrow bands were not observable in this example. A second example is described below in which narrow spectral bands were detected.

Plasma Feedback Example 2

In the second example, narrow spectral bands of radiation 1124 generated by plasma in the skin sample 1118 are experimentally observed. The optical system used for this detection is described in FIG. 11A. The optical system includes a fiber optic that allows for optical communication between the optical system and an Ocean Optics Spectrometer Model No. HR2000+ES. The optical system is optically communicative with a Q-switch Nd: YAG laser (Quantel Q-Smart 450) with an articulating arm such that a laser beam from the Q-switch Nd: YAG laser is directed into the system.

The skin sample 1118 is placed generally parallel to a focal region of the laser beam. The focal region is first placed just below a surface of the skin sample 1118. Multiple laser pulses were directed towards the sample skin 1118 with a spectrometer measurement being taken just after each laser pulse. Each laser pulse has sufficient peak power to produce an optical breakdown resulting in the generation of a plasma in the skin sample 1118. Radiation 1124 from the plasma is captured, as described in reference to FIG. 11A, and communicated to the spectrometer.

Figure 14:
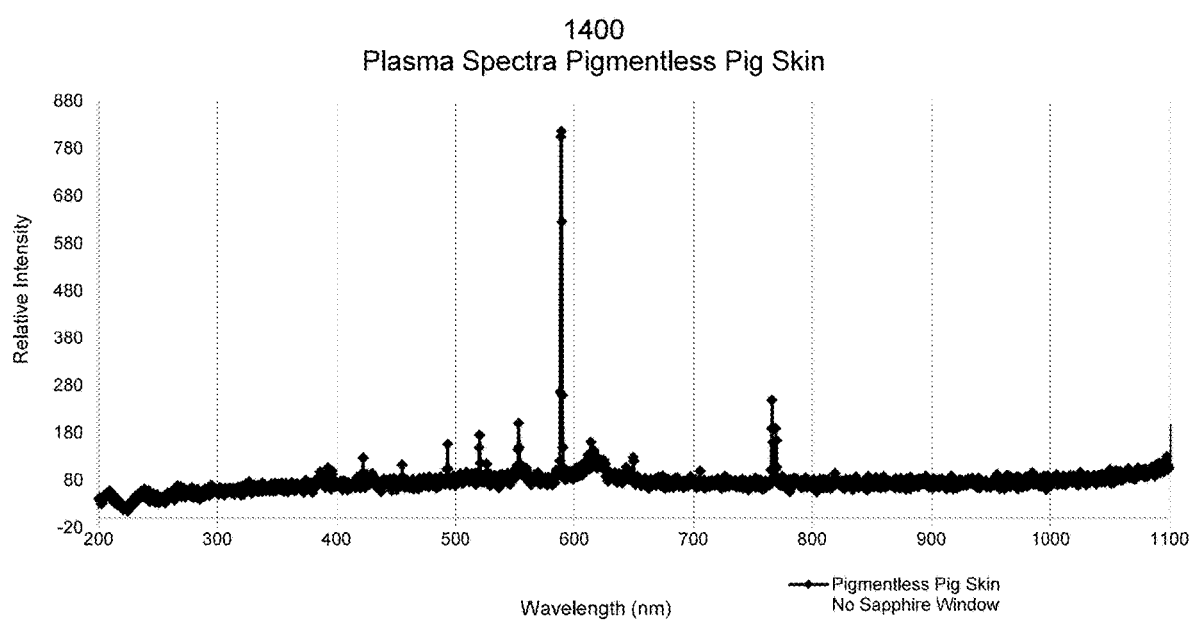
FIG. 14 illustrates spectra of radiation generated by plasma in a skin sample, according to some embodiments.

FIG. 14 illustrates spectra of radiation 1124 generated by plasma in the skin sample 1118. Spectral results captured from the plasma after each laser pulse were averaged. The average spectra is shown in a chart 1400 shown in FIG. 14. The chart 1400 has relative intensity in arbitrary units along a vertical axis and wavelength in nanometers along a horizontal axis. The averaged spectra includes spectral peaks at about 589 nm and 766 nm. The averaged spectra also includes minor spectral peaks at about 422 nm, about 455 nm, about 493 nm, about 521 nm, about 553 nm, about 614 nm, and about 649 nm.

Figure 15:
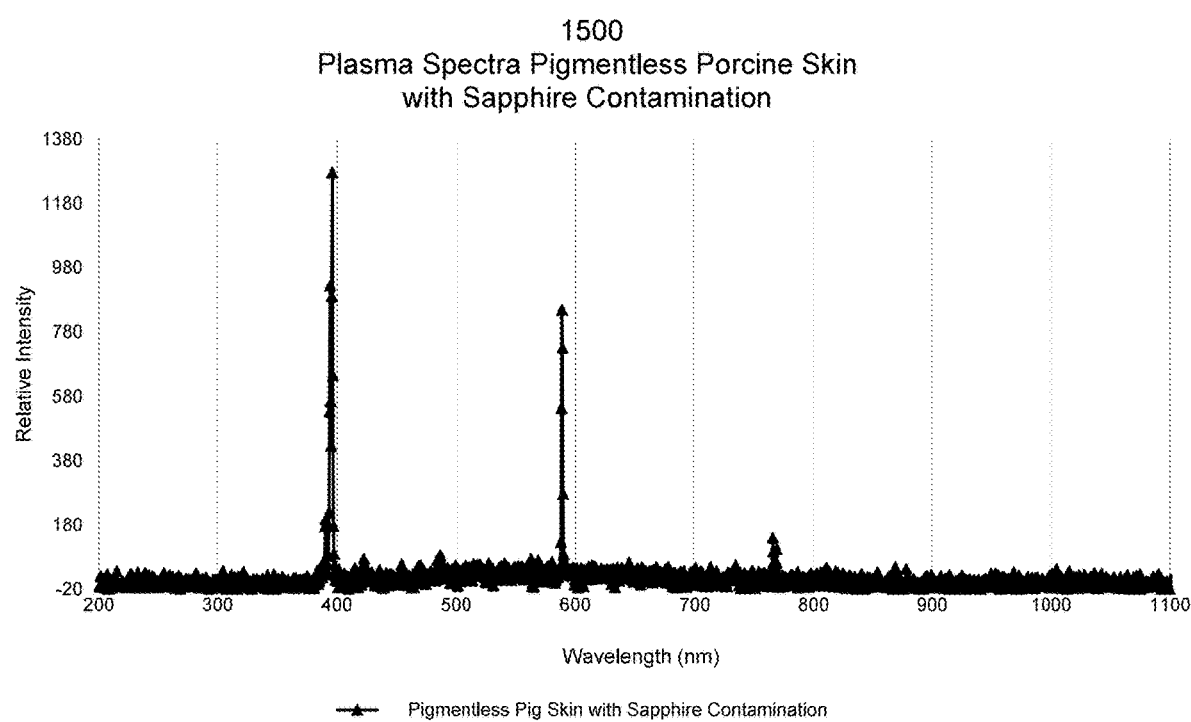
FIG. 15 illustrates the radiation spectra from a plasma formed using a sapphire window, according to some embodiments.

During the experiment, a sapphire window is placed between the skin sample 1118 and the focus optic 1116 in the path of the laser beam 1112. The laser beam 1112 is directed through the sapphire window into a waist/focal region located about 0.5 mm below the surface of the skin. FIG. 15 contains a chart 1500 that illustrates a radiation spectra from a plasma formed using a sapphire window in contact with the tissue. The chart 1500 has relative intensity in arbitrary units along a vertical axis and wavelength in nanometers along a horizontal axis. It can be seen in FIG. 15 that the major peaks at about 589 nm and about 766 nm are present. Additionally, an even larger peak is located at about 396 nm. It has been discovered after the measurement that the sapphire window is damaged (e.g., etched) in a way consistent with a plasma being formed within it. The 396 nm peak occurs repeatedly with the sapphire window present, only occurs when the sapphire window is present; and, the sapphire window appears damaged by plasma formation. This observation indicates that this peak at about 396 nm can be used as an indicator of plasma formation within the sapphire window.

According to some embodiments, material components of a plasma are determined through spectral analysis and one or more parameters of laser beam are adjusted based upon the material components of the plasma. For example, according to some embodiments a controller determines, from the spectral data, that a material other than that being treated is being affected by a plasma and adjusts laser parameters or deactivates a laser source. Although, the second example uses a spectrometer for detection of spectral content of the plasma, some embodiments determine spectral content of the plasma through alternative methods. For example, in some versions, a narrow band filter that passes only light centered about 396 nm is placed over a photodiode, such that the photodiode detects light only at 396 nm. The photodiode is triggered to collect moments after (e.g., 10 μS) after an EMR pulse. And, the controller is configured to stop firing the EMR source when the photodiode detects relatively high values, as relatively high values will only occur when the plasma affects the sapphire window.

Plasma Feedback Example 3

A third example demonstrates a plasma detection system that detects plasma incorporated into an EMR-based treatment hand piece.

Figure 16A:
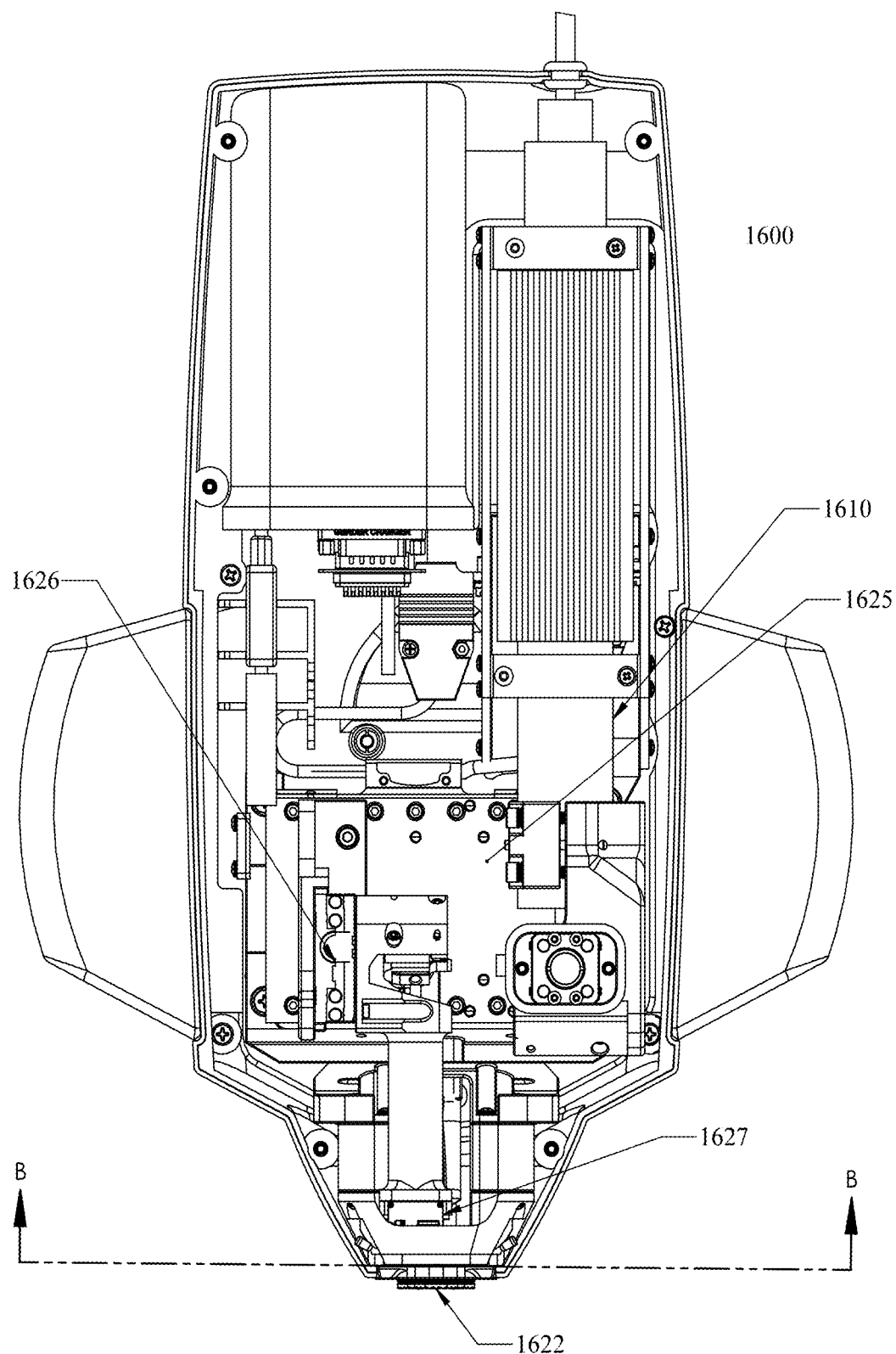
FIG. 16A illustrates a front view of an exemplary version of a plasma detection system, according to some embodiments.
Figure 16B:
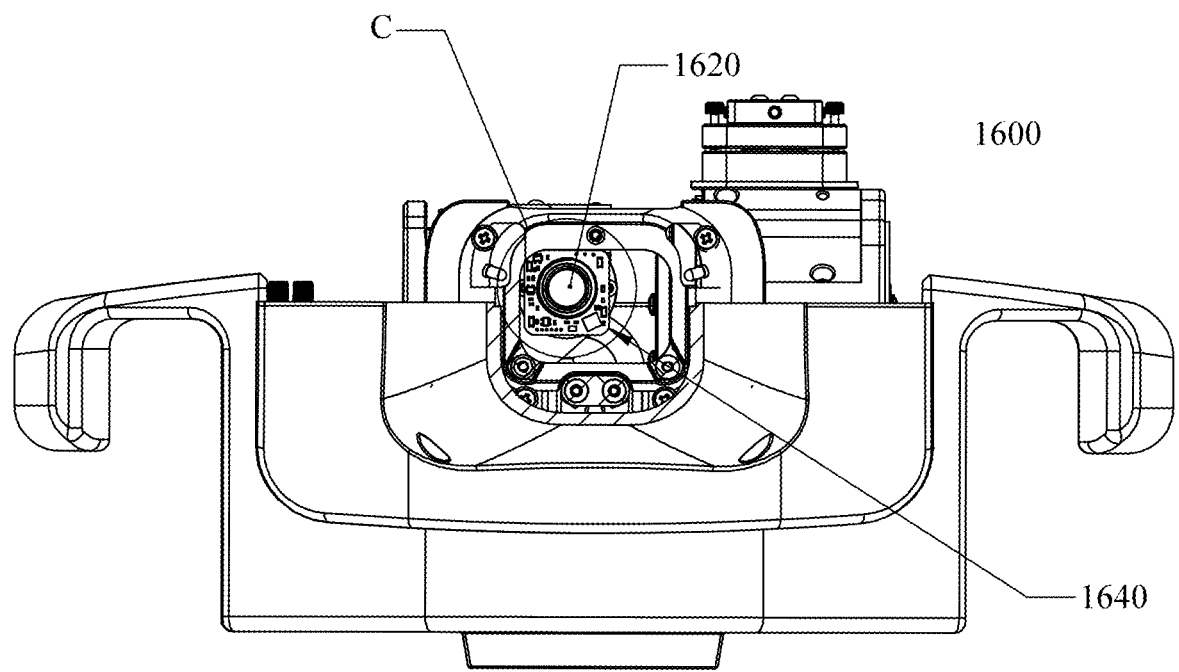
FIG. 16B illustrates a cross-sectional view of an exemplary version of a plasma detection system, according to some embodiments.
Figure 16C:
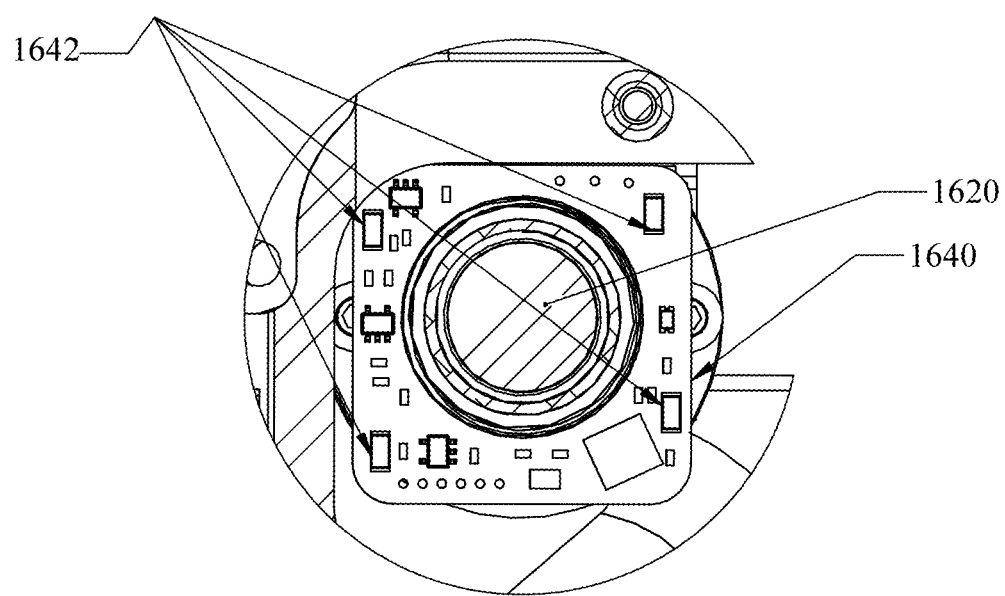
FIG. 16C illustrates a detail view of an exemplary version of a plasma detection system, according to some embodiments.

FIGS. 16A-16C illustrate drawings of according to the third example of tissue treatment and plasma detection. A tissue treatment and plasma detection system 1600 is shown in FIGS. 16A-16C. FIG. 16A shows a front view of the system 1600. FIG. 16B shows a cross-sectional view of the system 1600 taken along a B-B section line in FIG. 16A. And FIG. 16C shows a detail view taken from within a C detail circle in FIG. 16B.

A fiber laser 1610 is configured to output a treatment radiation. An example of the fiber laser 1610 is a Feibo 1060 nm, 40 W, 20 kHz, fiber laser from Feibo Laser Technologies Co., Ltd. Of Shanghai, China. The treatment radiation is directed by an optical system to a focus optic 1620. An example focus optic is Thorlabs Part No.: A240. The focus optic 1620 is configured to focus the treatment radiation through a window 1622 to a focal region in a tissue (not shown). The optical system is configured to allow the focus optic 1620 to be scanned in all three dimensions. This subsequently causes the focal region of the treatment radiation to be scanned in all three dimensions within the tissue. Scanning is achieved by three separate stages each responsible for a single axis. An X-stage 1625 scans the focus optic in an X-axis. A Y-stage 1626 mounted to the X-stage 1625 scans the focus optic in a Y-axis. And, a Z-stage 1627 mounted to the Y-stage 1626 scans the focus optic in a Z-axis (e.g., generally along an optical axis of the focus optic). An exemplary X-stage is a Dover MMX 50 from Dover Motion of Boxborough, Massachusetts, USA, controlled with an Elmo DC whistle Gold controller from Elmo Motion Control Ltd. of Petach-Tikva, Israel. An exemplary Y-stage is a Q545.140 stage controlled with E 873 controller both from Physik Instrumente L.P. of Auburn, Massachusetts, USA. An exemplary Z-stage is a New Scale 3M-FS from New Scale Technologies, Inc. of Victor, New York, USA.

A printed circuit board (PCB) 1640 is adhered to the Z-stage 1627 and faces the window 1622. The PCB 1640 contains a number of electronic components and four photodiodes 1642. An example photodiode is an Osram CHIPLED part number SFH 2711 from OSRAM GmbH of Munich, Germany. Another example photodiode is a Gallium Nitride Based sensor, GUVA-S12SD from Roithner Lasertechnik GmbH of Vienna Austria. Both example photodiodes may be advantageous in some embodiments, because they are more sensitive detecting light in ultra-violet (UV) and visible spectrum than in near-infrared (NIR). For this reason, these example photodiodes will detect light from a plasma, but detect less reflected or scattered treatment radiation (e.g., 1060 nm laser light). In other embodiments, the photodiodes may be coated with an optical coating (e.g., interference notch filter coating) to prevent detection of the treatment wavelength. In still other embodiments, the photodiodes may be placed behind a spectral filter (e.g., interference notch filter film) to prevent detection of the treatment wavelength.

Light from a plasma is converted into a small current by one or more of the photodiodes 1642. The current is converted into a voltage by a transimpedance amplifier. The voltage is then amplified by one or more amplifiers and sampled by a microcontroller. The microcontroller samples the voltage using at least one of an analog to digital converter (ADC) and a comparator.

In some versions, a comparator compares the voltage to a threshold value and triggers a timer (e.g., 32678 Hz) when the voltage exceeds the threshold value. The microcontroller detects a plasma when the voltage stays above the threshold value for a defined duration (e.g., 3 ticks of the timer). In some embodiments, the threshold value is set high so that plasma originating from treatment within the tissue will not exceed the threshold value, but closer and brighter plasma originating from within an optical window will. In this case, the plasma detector may be used for detecting unwanted plasma, such as plasma in the periphery tissue or optical window, which may cause damage to the patient or the system. Once the plasma is detected, a signal can be sent to another controller (e.g., laser controller) that can log the plasma detection or alter treatments based upon the detection (e.g., stop treatment radiation).

According to some embodiments, the ADC may be used to detect plasma within the tissue (e.g., plasma consistent with treatment). The ADC assigns a digital value representative of plasma intensity based upon the voltage from the one or more photodetectors. In some cases, the digital value is logged along with current location values for one or more of the X-stage 1625, the Y-stage 1626, and the Z-stage 1627. In this case, the logging of digital values relative focal region location can be formatted into a matrix (e.g., a map). The matrix may be used to indicate effectiveness of treatment or presence of chromophores within the tissue.

In some embodiments, presence of plasma at a first depth (e.g., relatively shallow) can indicate damage to the system or an adverse event; while, presence of plasma at a second depth (e.g., relatively deep within the tissue) can indicate an effective treatment. It is, therefore, important in some embodiments, to ensure that a focal region of the EMR beam is position at a desired focal depth.

Focal Depth Referencing Examples

As described in detail above, a depth of a focal region within a tissue needs to be tightly controlled (e.g., +/−20 μm), in some embodiments. For example, treatment of dermal pigment requires a focal region be placed at a depth approximately at the depth of the dermal pigment within the tissue. If the focal region is too deep below the dermal pigment treatment will not be effective. If the focal region is too shallow, melanocytes at the basal layer will be irradiated potentially causing an adverse event (e.g., hyperpigmentation or hypopigmentation).

Figure 17:
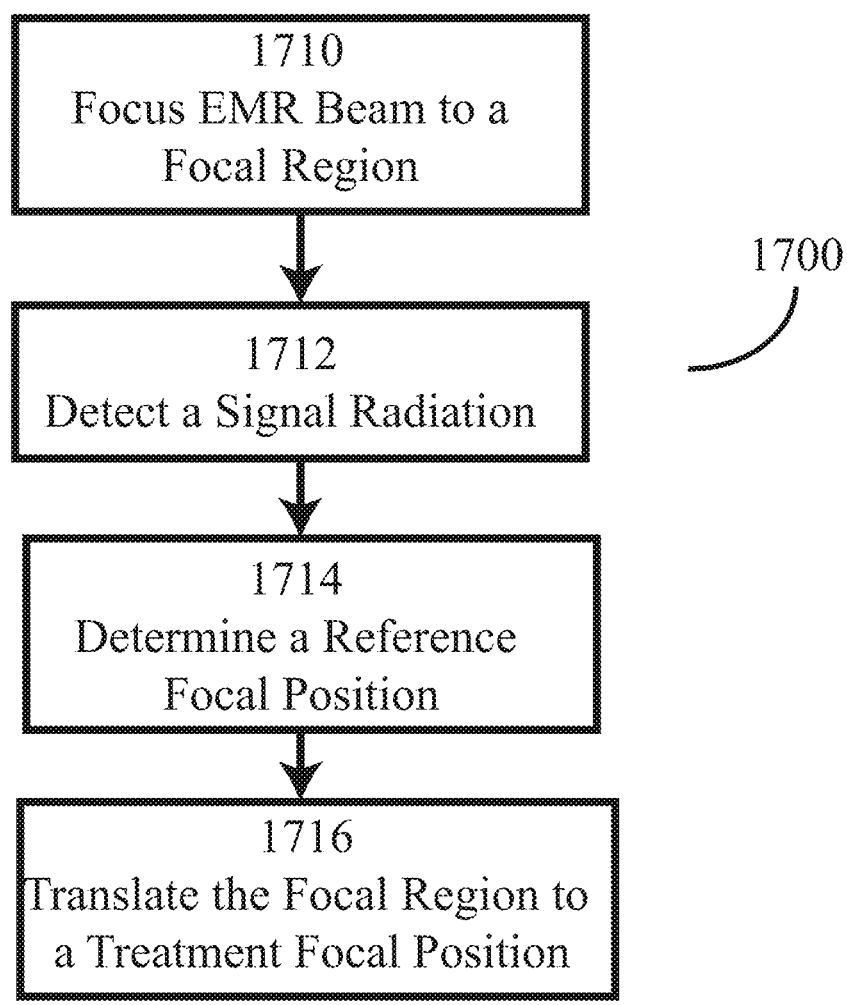
FIG. 17 illustrates a flow chart for window referencing, according to some embodiments.

Referring to FIG. 17, a flow chart 1700 is shown for a focal depth referencing method 1700, according to some embodiments. First, an electromagnetic radiation (EMR) beam is focused along an optical axis to a focal region 1710. In many cases, the EMR beam is generated by an EMR source (e.g., laser). An optical window is disposed to intersect the optical axis. In some versions, a surface of the window is substantially orthogonal to the optical axis. The EMR beam impinges upon at least one surface of the optical window and a signal radiation is generated. The signal radiation in some embodiments includes a reflected portion of the EMR beam that is reflected at a surface of the window. In some embodiments, the window is configured to contact a tissue. The surface of the window may be understood optically as an optical interface between a window material of the window and an adjacent material proximal the surface of the window (e.g., air or tissue). In some cases, a difference in index of refraction between the window material and the adjacent material results in reflection of the reflected portion of the EMR beam. According to some embodiments, a signal radiation is generated by scatter or transmission of a portion of the EMR beam at the window.

The signal radiation is detected 1712. According to some embodiments, the signal radiation is imaged by an imaging system. In some cases, an image of the signal radiation is formed at a sensor by the imaging system. Examples of sensors include photosensors and image sensors. In some versions, a detector detects and measures an image width. In general, the image width will be proportionally related to a beam width of the EMR beam incident the surface of the window. A magnification of the imaging system typically determines the proportionality of the image width to a width of the EMR beam incident the window. According to some embodiments, the detector detects and measures an intensity of the signal radiation.

Based upon the signal radiation, a reference focal position is determined 1714. For example, in some versions, the beam width of the EMR beam incident a surface of the window is measured, and a focal position of the focal region is translated along the optical axis as the beam width is measured. The reference position is found where the beam width is determined to be at a minimum. For another example, in some versions, an intensity of the signal radiation is detected as the focal position of the focal region is translated along the optical axis. In this case, the reference position is found where a radiation signal intensity is found to be at a maximum.

Once the reference focal position is determined, the focal region is translated to a treatment focal position 1716. Typically, the treatment focal position is a predetermined distance away from the reference focal position along the optical axis. According to some embodiments, the focal region is translated by moving an optical element (e.g., objective) along the optical axis. In other embodiments, the focal region is translated by adjusting a divergence of the EMR beam, for example adjusting an optical power of an optical element. Eventually, the window is placed in contact with a target tissue resulting in the focal region being positioned within the target tissue. According to some embodiments, the target tissue is skin and the focal region is positioned within a dermal tissue of the skin. Precise depth positioning of the focal region within tissue allows for treatment of previously untreatable pigmentary conditions through thermionic-plasma or thermal disruption. For example, the EMR beam can perform selective thermionic-plasma mediated treatment of dermal pigmentary condition (e.g., dermal melasma) at a focal region located within the dermis without risking adverse irradiation of the epidermis.

Figure 18A:
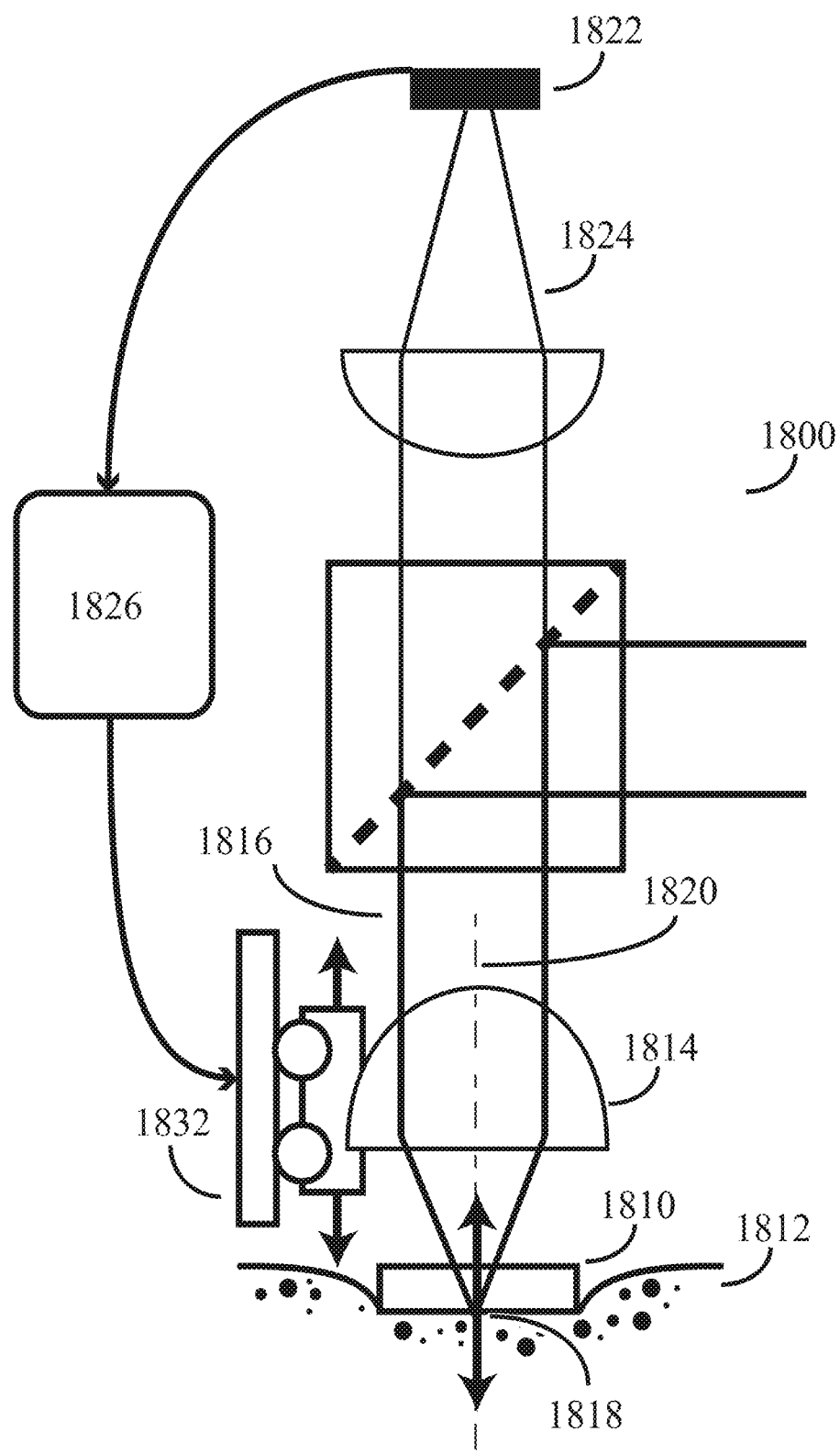
FIG. 18A illustrates schematics of a window referencing system, according to some embodiments.
Figure 18B:
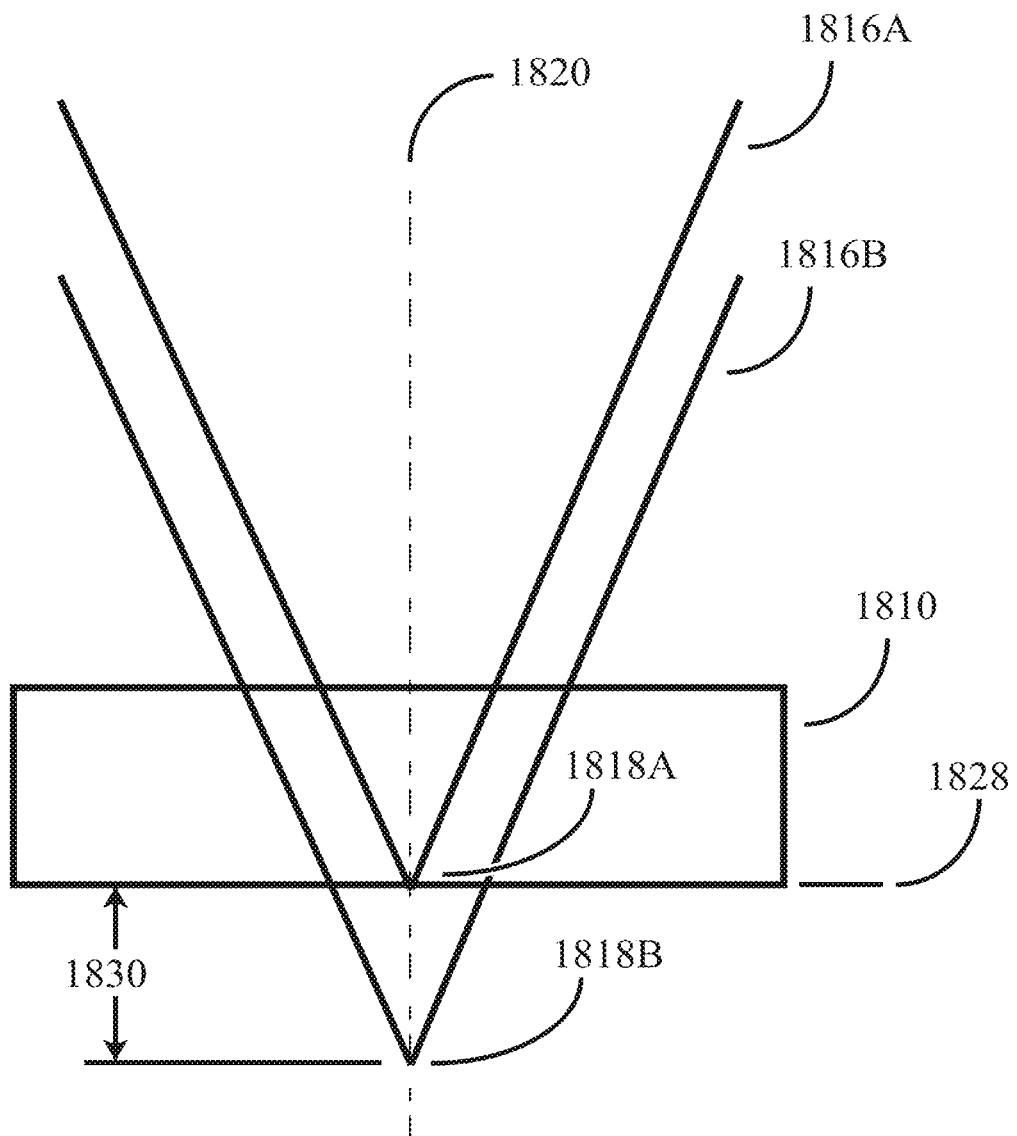
FIG. 18B illustrates performance of a window referencing system, according to some embodiments.

Referring to FIG. 18B, in some embodiments, a second EMR beam 1816B is configured to be converged by the focus optic to a second focal region 1818B located in the treatment position. In this case, the first EMR beam 1816A may be configured only for referencing (e.g., by bringing a first focal region 1818A incident upon the surface of window 1810 and the second EMR beam 1816B may configured to achieve the desired effect in the tissue (e.g., a cosmetic effect). This may be advantageous in embodiments, where the tissue effect requires very high fluence (e.g., $10^{12}$ W/cm$^2$) and the window 1810 would likely be damaged if the first EMR beam were to be used during referencing. According to some embodiments, the second EMR beam 1816B has a wavelength that approximately equal to the first EMR beam 1816A. In other embodiments, the second EMR beam 1816B has a wavelength that is different than that of the first EMR beam 1816A. In this case, the treatment position may require calibration based upon differences in a focal length of the focus optic at the two different wavelengths.

Referring to now FIGS. 18A-18B, schematics are shown for a focal depth referencing and treatment system 1800, according to some embodiments. The focal depth referencing system 1800 includes a window 1810 configured to contact a target tissue 1812. An optical system (e.g., objective or focus optic) is configured to focus an electromagnetic radiation (EMR) beam 1816 to a focal region 1818 along an optical axis 1820. The optical axis 1820 intersects the window 1810. An optical detector 1822 is configured to detect a signal radiation 1824. According to some embodiments, the signal radiation 1824 is generated by an interaction between the EMR beam 1820 and the window 1810. In some versions, the interaction between the EMR beam 1820 and the window 1810 is an interaction between a surface of the window 1810 and the EMR beam. The interaction between the EMR beam 1820 and the window 1810 typically is at least one of reflection, transmission, and scatter.

A controller 1826 is configured to take input from the optical detector 1822 and translate a focal position of the focal region 1818 along the optical axis 1820. Based at least in part upon feedback from the optical detector 1822, the controller 1826 determines a reference position 1828 where a portion of the focal region 1818 is substantially coincident with a surface of the window 1810.

The signal radiation 1824 may emanate from a reflection of the EMR beam 1816 incident the surface of the window 1810 and be imaged incident an image sensor 1822 using (in part) the focus optic 1814. According to some embodiments, the controller 1826 determines the reference position by determining a transverse width of the EMR beam 1816 that is incident upon the surface of the window based upon the signal radiation; and, translating the focal region until the transverse width has a minimum value. According to another embodiment, the signal radiation emanates from a reflection of the EMR beam 1816 at a surface of the window 1810 and the detector 1822 is configured to detect an intensity of the signal radiation. In this case the controller may determine the reference position by translating focal region until the intensity of the signal radiation has a maximum value.

Finally, the controller 1826 translates the focal region 1818 to a treatment position a predetermined distance 1830 from the reference position 1828. In general, translating the focal region 1818 away from the reference position 1828 is done in a positive direction along the optical axis 1820 (i.e., away from the optical system 1814). In some embodiments, the treatment position is configured to be located within a tissue. For example, the predetermined distance can be configured to locate the treatment position within a dermal tissue in skin. A stage 1832 can be used to translate one or more optical elements (e.g., the focus optic) in order to translate the focal region. The EMR beam 1816 typically is configured to perform an effect in tissue (e.g., a cosmetic effect) at or near the focal region located in the treatment position. An example tissue effect is selective thermionic plasma-mediated treatment of the tissue 1812.

In some embodiments, a second EMR beam is configured to be converged by the focus optic to a second focal region located in the treatment position. In this case the first EMR beam may be configured only for referencing and the second EMR beam may configured to perform the tissue effect. This may be advantageous in embodiments, where the tissue effect requires very high fluence (e.g., $10^{12}$ W/cm$^2$) and the window 1810 would likely be damaged during referencing. According to some embodiments, the second EMR beam has a wavelength that is identical to the first EMR beam. In other embodiments, the second EMR beam has a wavelength that is different than that of the first EMR beam. In this case, the treatment position will need to be calibrated based upon differences in a focal length of the focus optic at the two different wavelengths. In some embodiments, a window referencing and treatment system 1800 is used to measure more than one reference position 1828.

For example, according to some embodiments, the window referencing and treatment system 1800 also includes a scanning system. The scanning system is configured to move the focal region 1818 and optical axis 1820 in at least one scan axis. In some cases, the scan axes can be generally perpendicular to the optical axis 1820.

A parallelism measurement between the window and a scan axis can be determined by way of multiple reference position 1828 measurements at multiple scan locations. For example, the referencing system 1800 is first used to determine a first reference position at a first scan location. Then, the scanning system relocates the optical axis 1818 to a second scan location a distance along the scan axis from the first scan location. The referencing system 1800 then determines a second reference position. A difference between the first and second reference positions divided by the distance along the scan axis indicates a slope of non-parallelism between the window and the scan axis. Individual embodiments are provided below to further explain focal depth referencing in an EMR treatment device.

Focal Depth Referencing Example 1

A first focal depth referencing example is described below. The first focal depth referencing example employs a feedback system such as a confocal microscope. This configuration is advantageous in some embodiments as it can be used to reference surfaces within a tissue as well as external tissue surfaces and window surfaces. For example, according to some embodiments, a focal region is referenced relative a dermal-epidermal (DE) junction within the skin. This is achievable in some embodiments because of an index of refraction difference between the epidermis (or melanin in a basal layer of the epidermis) and the dermis.

Figure 19:
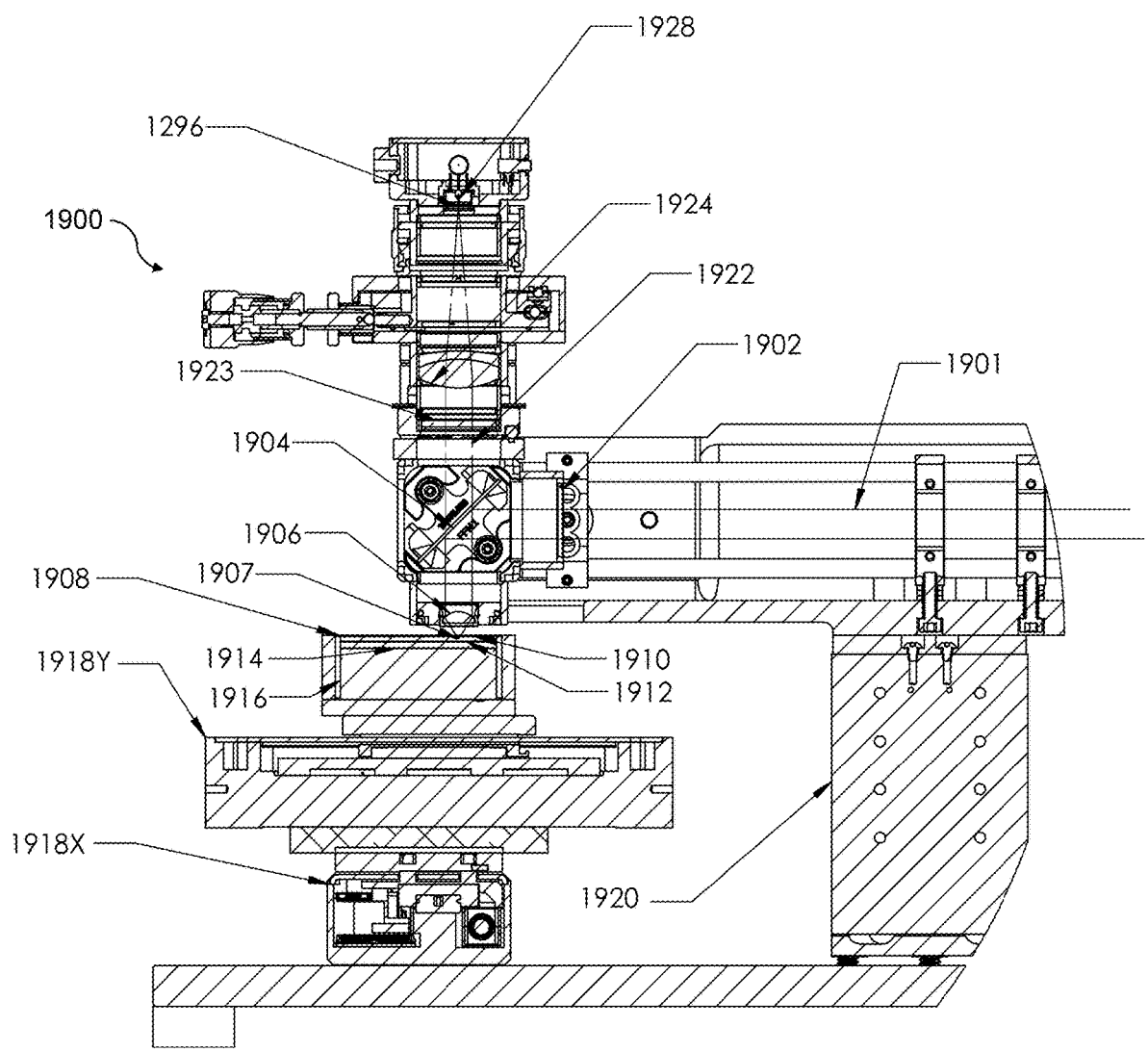
FIG. 19 illustrates an exemplary bench prototype for confocal imaging, according to some embodiments.

FIG. 19 illustrates a bench prototype 1900 for confocal imaging and plasma mediated therapy. A collimated laser beam 1901 enters the prototype 1900 through an entrance aperture 1902 and is projected upon a reflector 1904. The reflector 1904 folds the laser beam 1901 toward an objective 1906. The objective 1906 focuses the laser beam 1901 to a focal region 1907. The focused laser beam 1901 is directed toward a sample holder 1908. The sample holder 1908 includes a window 1910, and a sample located optically downstream from the window 1910. The sample shown in FIG. 19 is skin that includes an epidermis 1912 and a dermis 1914 located optically downstream from the epidermis 1912. A compliant material, such as foam 1916, is used to press the sample against the window 1910 and the window against a landing of the sample holder 1908. The sample holder sits atop an X-Y stage 1918X and 1918Y. The prototype 1900 scans the sample relative the laser beam. A Z-stage 1920 allows a distance between the objective 1906 and the sample holder 1908 to be adjusted. A micrometer screw gauge allows for tightly controlled movement of the Z-stage 1920. The objective 1906 collimates a returned light 1922 from the focal region 1907. The radiation 1922 is at least partially transmitted through the reflector 1904. According to some embodiments, radiation 1922 passes through a filter 1923 (e.g. a notch filter) such that only portions of the radiation 1922 having a certain wavelength range are accepted. The radiation 1922 is focused by a tube lens 1924 to an aperture 1926. The aperture 1926 is sized to accept only rays of light originating from focus 1907 (e.g., less than 50 μm). Finally, the radiation 1922 is projected upon a photodiode 1928.

In one implementation, the optical system 1900 is used as a confocal microscope. This can be done, for example, by placing the second objective 1924 upstream from the aperture 1926. The aperture 1926 can reimage the signal radiation 1922 by focusing the signal radiation at a focal plane that includes the aperture 1926. The aperture 1926 can filter (e.g., block) undesirable spatial frequencies of the signal radiation 1922. This configuration can allow for filtering of signal radiation associated with different regions in the target tissue 1912 and 1914 (e.g., regions of target tissue at different depths relative to tissue surface). By changing the distance between the imaging aperture 1926 and the target tissue 1912 and 1914 (e.g., by moving imaging aperture 1926 along the path of signal radiation 1922), different depths of the target tissue can be imaged 1926 by transmitting commands to an actuator. The controller 506 can analyze the detection data and determine the presence of plasma in the target tissue 1912 and 1914, distribution of pigments in the target tissue, and the like.

Focusing a laser beam at a prescribed depth below a surface requires precise placement of the focal region 1907 relative to the surface. It is therefore advantageous in some embodiments, to determine the location of the objective 1916 relative the surface of the sample (e.g., surface of the sample facing the objective 1906). This can be done by referencing the focal region 1907 with the surface of the sample. Using the bench prototype as described above, a test is performed to determine where the focal region is located with respect to the top and bottom surface of the window 1910 as well as to a top surface of a porcine skin sample.

A Nufern 30 W fiber laser operating at a wavelength of 1060 nm is used to provide the laser beam 1901 that has a diameter of about 7.5 mm. The reflector 1904 is a dichroic mirror which reflects more than 90% of the laser beam 1901 and transmits less than 10% at 1060 nm wavelength. The objective has an effective focal length of about 8 mm. The lens tube 1924 focuses the returned light 1922 with an effective focal length of about 30 mm. The aperture 1926 is about 30 micrometers wide. The fiber laser is operated at a power level of 0.1% (1 mJ/pulse) and a repetition rate of 30 KHz. A signal from the photodiode 1928 is displayed upon an oscilloscope. When the fiber laser is turned on, the Z-stage 1920 is slowly scanned until a maximum signal is captured by the oscilloscope.

Figure 20:
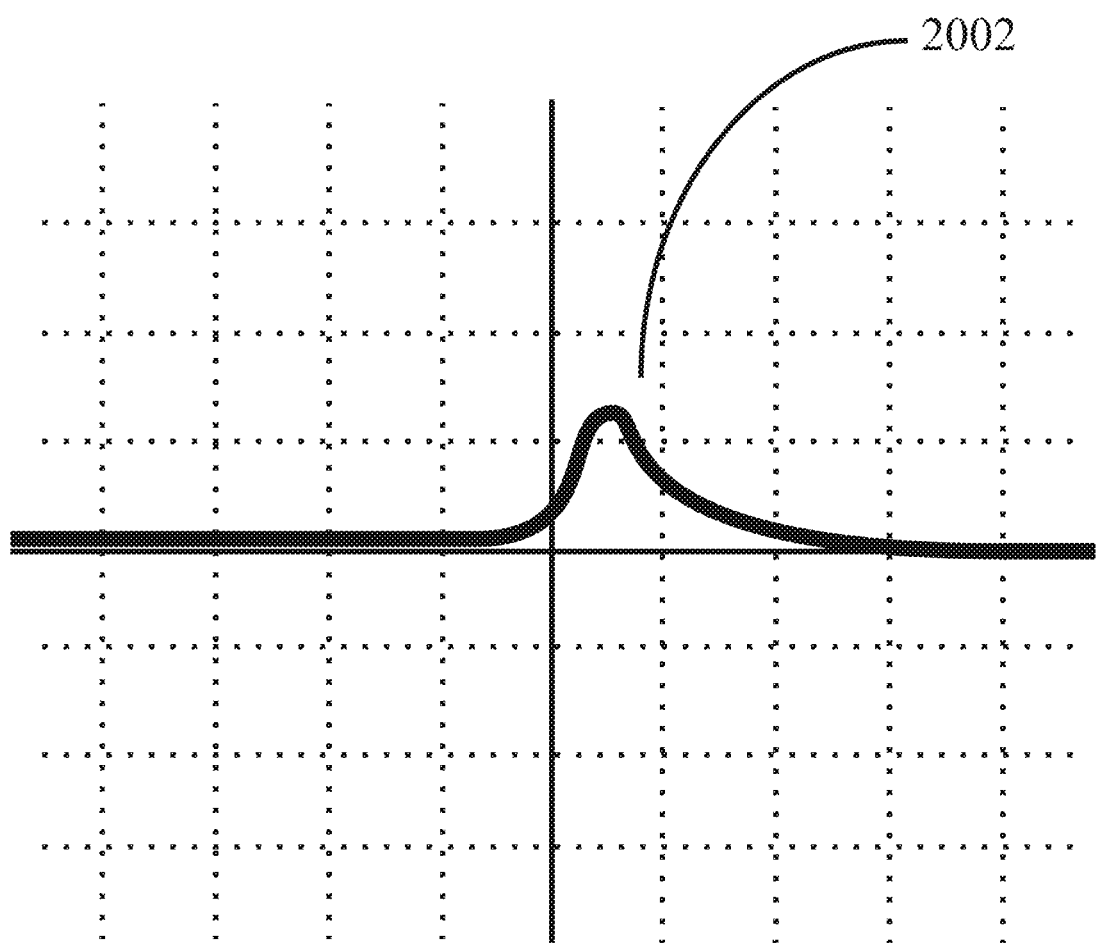
FIG. 20 illustrates a maximum radiation intensity measurement, according to some embodiments.

FIG. 20 illustrates a maximum radiation intensity measurement. Intensity is shown along a vertical axis in arbitrary units and time is shown along a horizontal axis. The maximum radiation intensity signal 2002 is generated when the focal region 1907 is collocated on the top surface of the window 1910. The Z-stage 1920 micrometer reported a relative position of 0.487 mm where the maximum signal 2002 is observed. No detectable signal is observed at relative Z-stage positions of 0.458 mm and 0.519 mm.

In the above example, the position of the focal region was referenced at a window interface where reflection at the interface was found to be greatest. A difference in the index of refraction between materials causes reflection at an interface between the two materials (e.g., air and the window). Reflection arising from a mismatch of index of refraction is sometimes understood as Fresnel reflection. Fresnel reflection varies with angle of incidence and light polarization. For simplicity, Fresnel reflection at a normal angle of incidence (which does not depend on polarization) will be shown as an example. A normal Fresnel reflection arising at a boundary between to materials having different indices of refraction will generally act according to:

$$R = \left| \frac{n_1 - n_2}{n_1 + n_2} \right|^2$$

where R is reflectance (proportion of light reflected), $n_1$ is index of refraction of a first material, and $n_2$ is index of refraction of a second material. A good example of Fresnel reflection is provided by diamond. A diamond has a very high index of refraction (e.g., 2.42). Air has an index of refraction of unity (e.g., 1.00). Fresnel reflectance of light normal to an air-diamond interface is approximately 17%. Fresnel reflectance tends to be at a minimum at a perpendicular angle and increases at grazing angles. So, for a diamond, nearly ⅕ of the light is reflected at the air diamond interface, at a minimum. The result is that a diamond sparkles in light.

Within skin, melanin has a different index of refraction different than the surrounding tissue at optical wavelengths (e.g., melanin's index of refraction at 1064 nm is about 1.78 and the epidermal index of refraction is about 1.35). Therefore, normal Fresnel reflectance is about 2% at a skin-melanin interface. A basal layer at the bottom of the epidermis contains melanocytes and is therefore very melanin rich. Just below the basal layer the dermis is typically free from melanin, except in pathological cases (notably dermal melasma). Therefore, in some embodiments the focal region is referenced with a dermal-epidermal junction (e.g., basal layer) of the skin.

Focal Depth Referencing Example 2

Figure 21A:
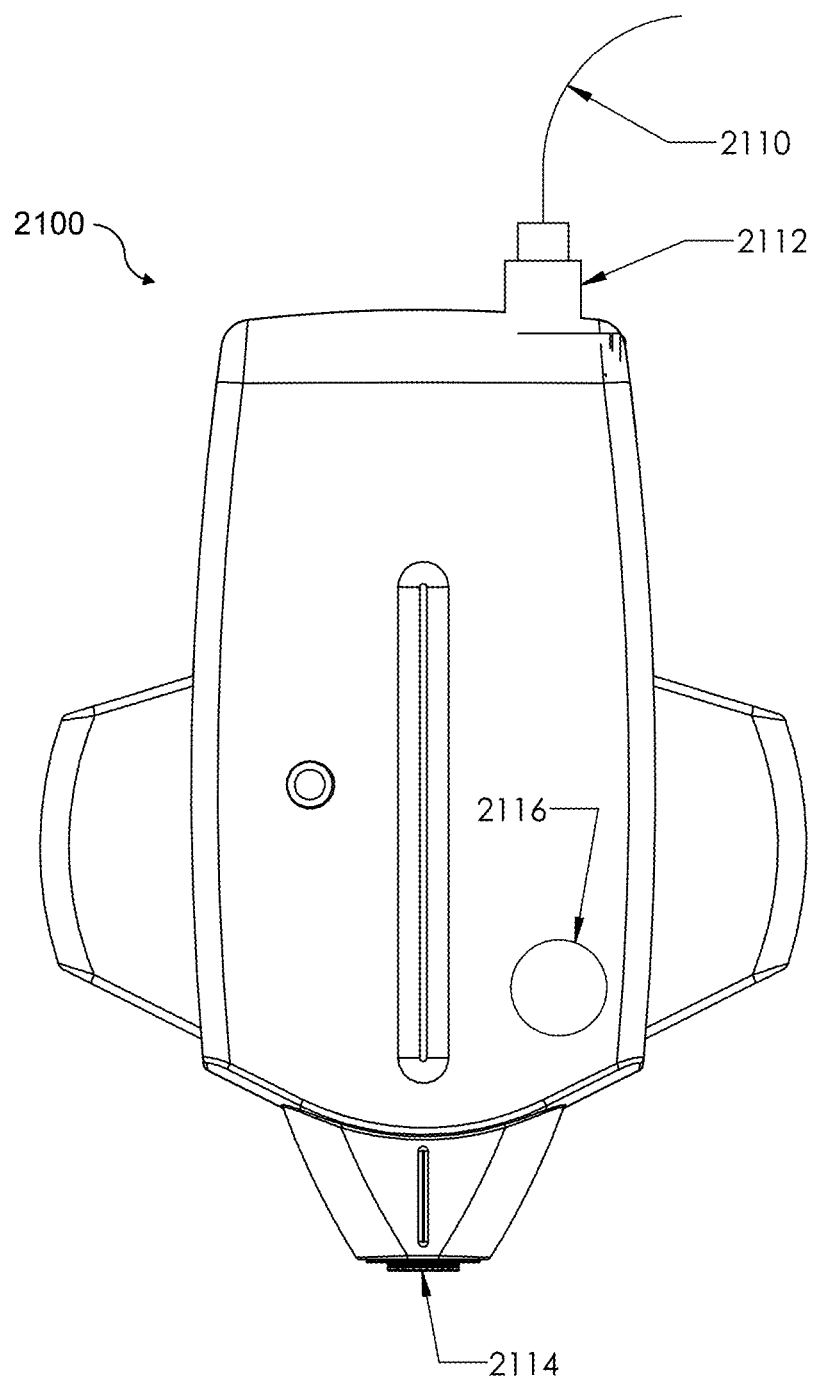
FIG. 21A illustrates a front view of an exemplary version of a treatment system without a removable window referencing system attached, according to some embodiments.
Figure 21B:
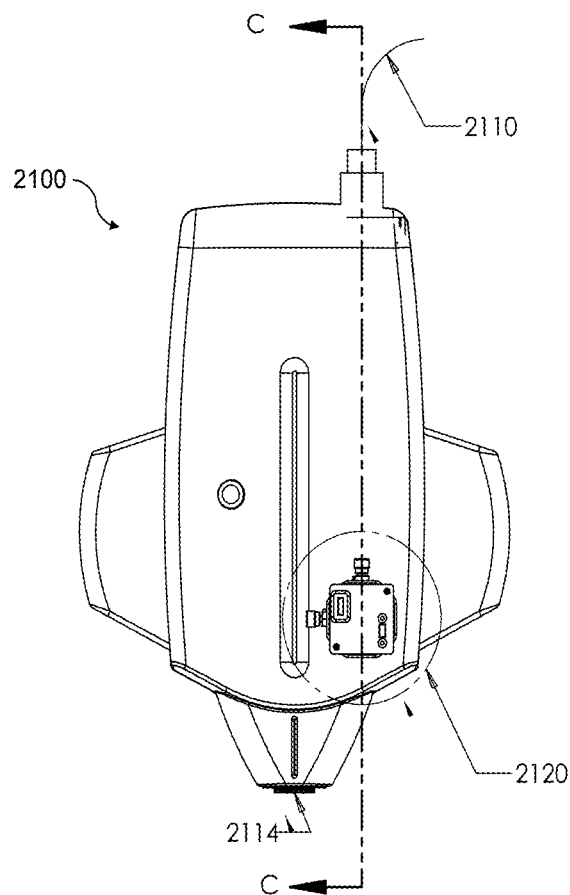
FIG. 21B illustrates a front view of an exemplary version of a treatment system with a removable window referencing system attached, according to some embodiments.
Figure 21C:
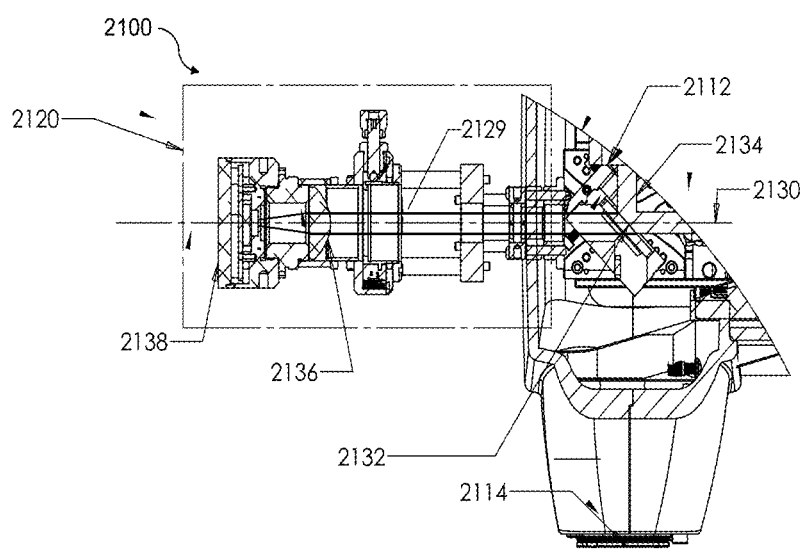
FIG. 21C illustrates a cross-sectional view of an exemplary version of a treatment system with a removable window referencing system attached, according to some embodiments.

A second focal depth referencing example uses a camera sensor instead of an imaging (e.g., confocal) aperture. FIGS. 21A-21C illustrate an example according to some embodiments. FIG. 21A shows a treatment system 2100 configured to direct and focus a radiation (e.g., laser) into a target tissue. The radiation beam is provided by a fiber optic 2110 and collimated by a collimator 2112. The radiation beam is focused and directed through the system 2100 by an optical system. The focused radiation beam is ultimately directed out of a window 2114 at the bottom of the system 2100. The window 2114 is configured to contact a treatment tissue, such that a focal region of the focusing radiation beam is located within the target tissue. The system 2100 also includes a port 2116. The port allows at least some portion of radiation from near the focal region to be directed out it. The port 2116 therefore allows for signal radiation from near the focal region to be "picked off" and detected. One use for the signal radiation is focal depth referencing to determine a reference focal position that corresponds with a partially reflective interface (e.g., a surface of the window 2114).

FIGS. 21B-21C illustrate the system 2100 having a removable referencing system 2120 attached to the port 2116. According to an exemplary use of the system 2100, the removable referencing system 2120 is installed prior to treatment and can be used to reliably locate the focal region relative a known reference (e.g., a tissue surface or a window surface). Referring to FIG. 21C, a signal radiation 2129 propagates generally along an optical axis 2130. A beam splitter 2132 allows at least a portion of the signal radiation 2129 to transmit toward the window referencing system 2120. According to some embodiments, the beam splitter substantially reflects the collimated radiation beam 2134, which is output from the collimator 2112. The signal radiation is imaged by an imaging lens 2136 (e.g., Edmund Optics PN: 33-020) onto a camera sensor 2138 (Mightex PN: SCE-B013-U). Measurements taken with the second focal depth referencing example system are provided below to demonstrate accuracy and usefulness of the system.

The measurements represent a position of an objective lens along an optical axis that results in a corresponding focal region being collocated with a surface of a window. Collocation of the focal region and the surface of the window was determined by a participant taking the measurement. The participant was responsible for determining the objective lens position that causes an image of the signal radiation to have a minimum size. The measurements were made by two participants. A first participant performed all measurements numbered 1 through 3 and a second participant performed all measurements numbered 4 through 6. Measurements were taken at all 4 corners of the window surface, top left (TL), top right (TR), bottom left (BL), bottom right (BR). A table below summarizes the measurement results.

| Exemplary EMR-Based Treatment and Window Referencing System | | | | | | | | |
|---|---|---|---|---|---|---|---|---|
| Focus Position | Measurement No. | | | | | | Average | Standard Deviation |
| (μm) | 1 | 2 | 3 | 4 | 5 | 6 | (μm) | (μm) |
| TL Window | 670 | 680 | 690.5 | 690 | 680 | 685.5 | 683 | 8 |
| TR Window | 670 | 679.5 | 685.5 | 670.5 | 680 | 685.5 | 679 | 7 |
| BL Window | 690 | 650 | 644.5 | 700 | 649.5 | 645 | 663 | 25 |
| TL Window | 700 | 670 | 660 | 700 | 670 | 670 | 678 | 17 |

The results of the measurements indicate repeatability of the exemplary window referencing system, even when minimum size of the image is subjectively determined by different participants. Although these measurements were made in part by using judgement from human participants, in some embodiments a controller is used to determine image size and control focal region location automatically. Also, as can been inferred from the results, a parallelism of the window surface relative one or more scan axes can be calculated from measurements made by the window referencing system. For example, one can approximate an angle between a scan axis and the window surface according to a following equation that assumes a small angle approximation:

$$\alpha = \frac{|Z_{ref,1} - Z_{ref,2}|}{d_{1-2}}$$

where: $\alpha$ is the angle between the scan axis and the window surface in radians; $Z_{ref,1}$ is the measured depth at a first location (e.g., $1^{st}$ corner of the window surface) in micrometers; $Z_{ref,2}$ is the measured depth at a second location (e.g., $2^{nd}$ corner of the window surface) in micrometers; and $d_{1-2}$ is a distance along one or more scan axis generally perpendicular to the optical axis between the first location and the second location in micrometers. The feedback and treatment system 2100 of FIGS. 18A-18C requires a "pick off" from an optical path (e.g., the beam splitter 1832). According to some embodiments, a "pick off" is not present.

Focal Depth Referencing Example 3

Figure 22A:
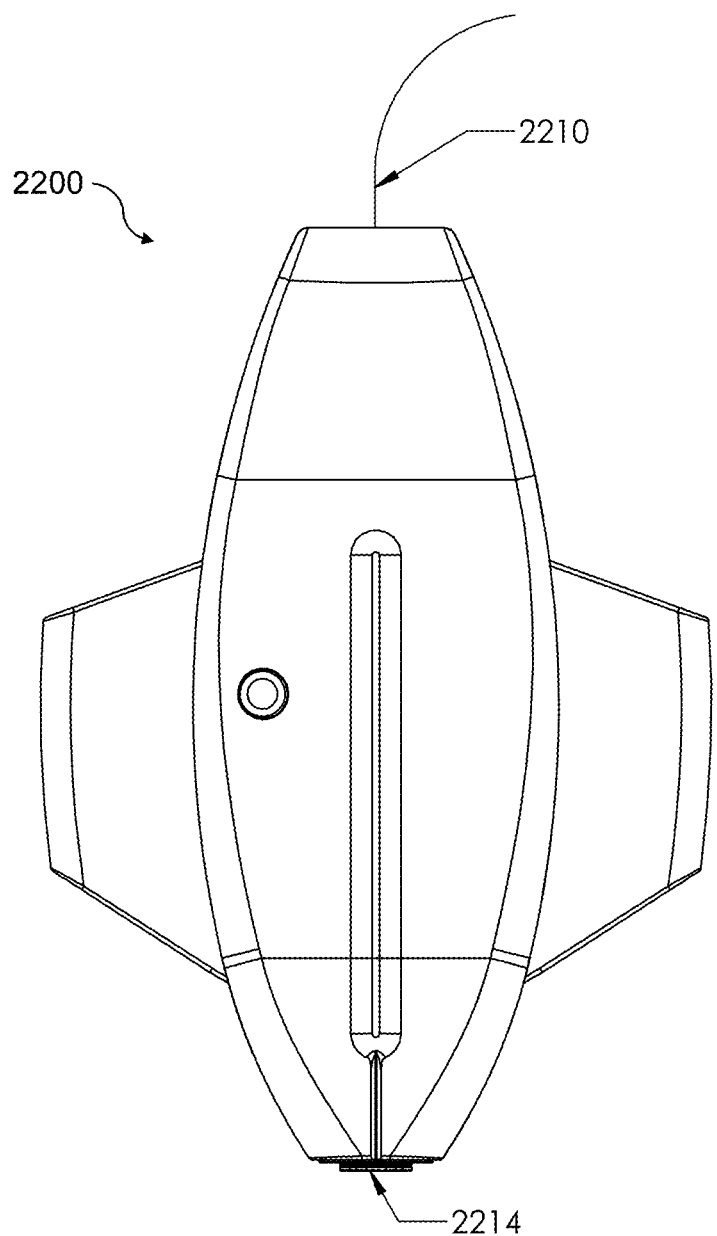
FIG. 22A illustrates a front view of an exemplary version of a treatment system without a window referencing system attached, according to some embodiments.
Figure 22B:
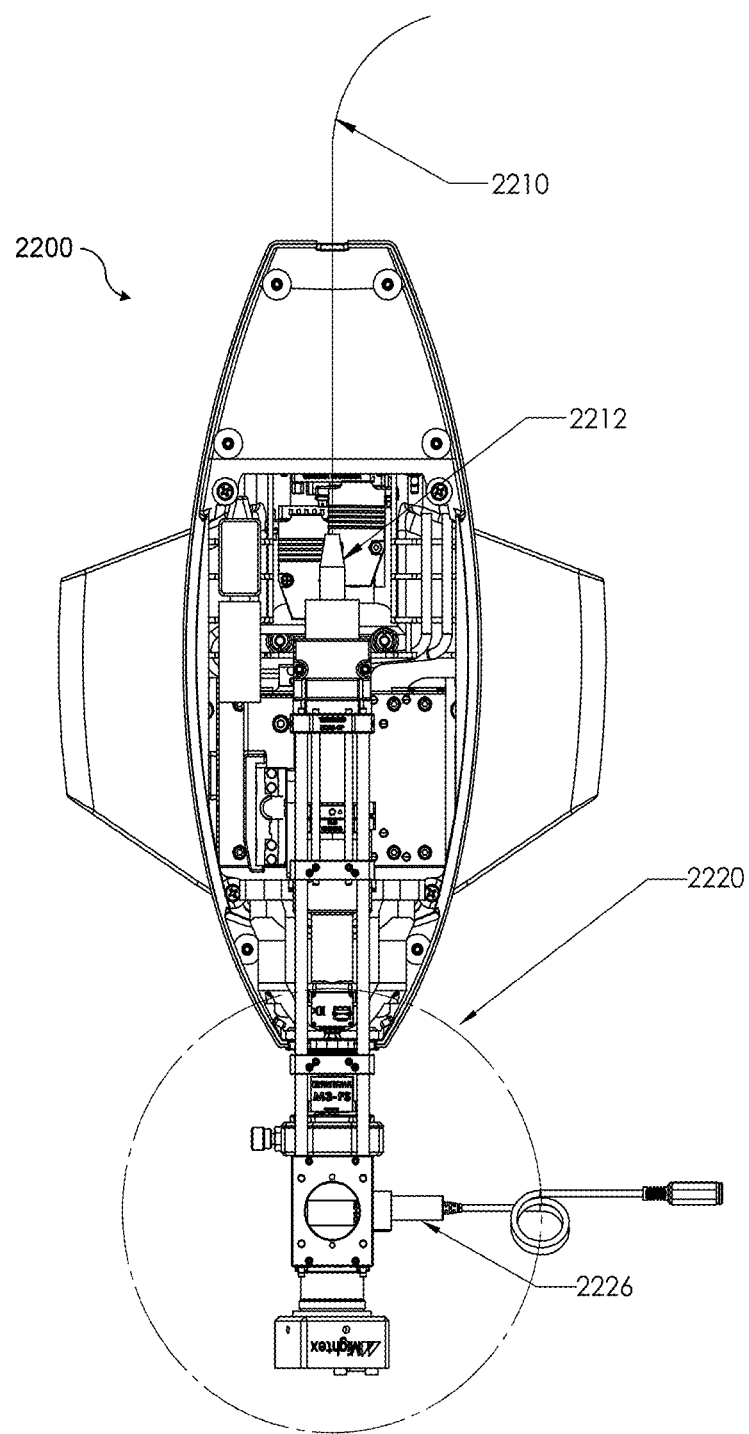
FIG. 22B illustrates a front view of an exemplary version of a treatment system with a window referencing system attached, according to some embodiments.
Figure 22C:
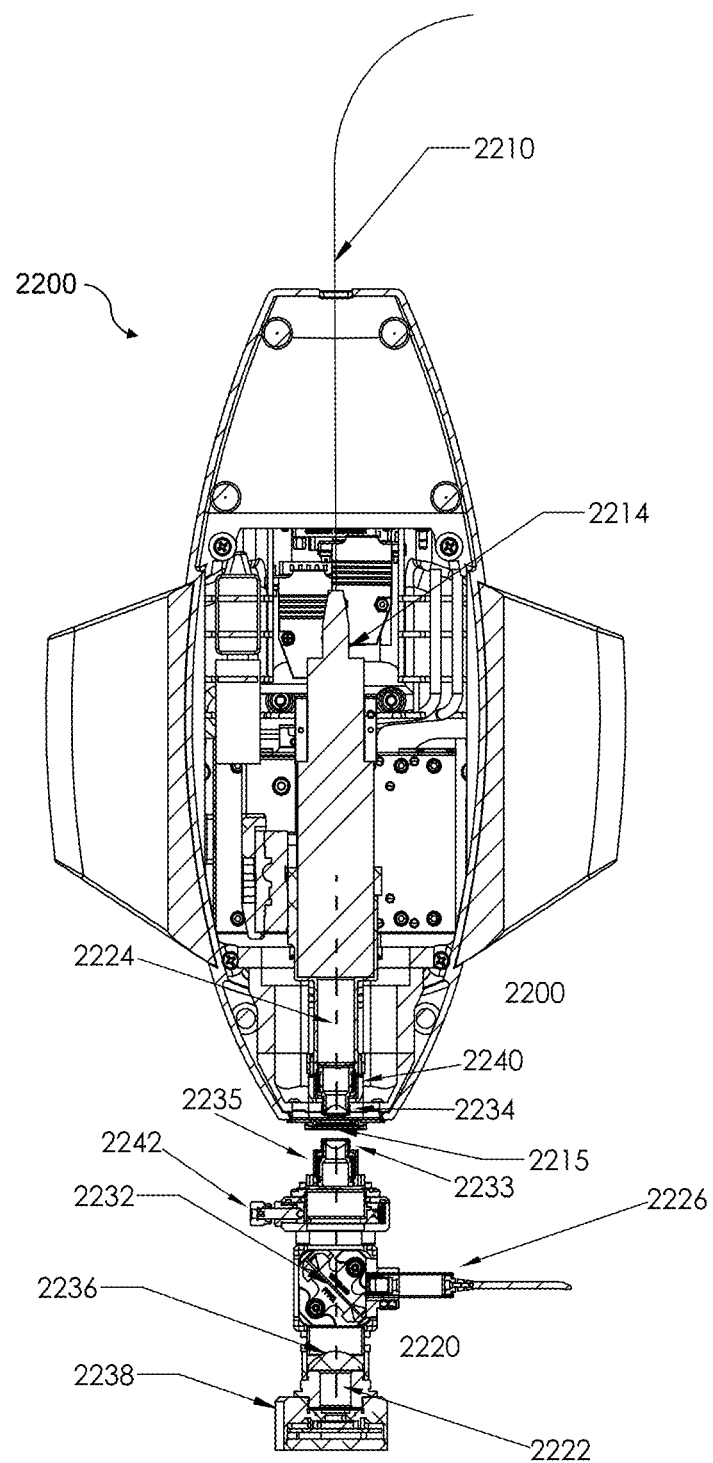
FIG. 22C illustrates a cross-sectional view of an exemplary version of a treatment system with a window referencing system attached, according to some embodiments.

FIGS. 22A-22C show another exemplary focal depth referencing and treatment system 2200 according to some embodiments. FIG. 22A shows a treatment system 2200 configured to direct and focus a radiation (e.g., laser) into a target tissue. The radiation beam is provided by a fiber optic 2210 and collimated by a collimator 2212. The radiation beam is focused and directed through the system 2200 by an optical system. The focusing radiation beam is ultimately directed out of a window 2214 at the bottom of the system 2200. The window 2214 is configured to contact a treatment tissue, such that a focal region of the focusing radiation beam is located within the target tissue. This system 2200 does not contain a port or a "pick off" in the optical system.

FIGS. 22B-22C illustrate the system 2200 having a removable referencing system 2220 attached. According to an exemplary use of the system 2200, the removable referencing system 2220 is installed prior to treatment and used to reliably locate the focal region relative a known reference (e.g., a window surface). The removable referencing system 2220 is attached to an outside diameter of the collimator 2212. This allows an optical axis 2222 of the referencing system 2220 to be nominally in line with an optical axis 2224 of the treatment system. A reference radiation is generated by a reference radiation source 2226 (e.g. diode laser Thorlabs PN: LPS-1064-APC-SP and a collimation lens [e.g., Edmund Optics PN 33-020]). The reference radiation is partially reflected by a beam splitter 2232 (e.g., 50-50 beam splitter Thorlabs PN: BSW4R-1064) and directed along the optical axis 2222 of the referencing system. The reference radiation is focused by a referencing objective 2233 (e.g., Thorlabs PN: C240TME-1064).

In some versions, the referencing objective 2233 has a prescription approximately equal to that of a treatment objective 2234. The referencing objective 2233 is in a reference stage 2235, which translates the referencing objective 2233 along the optical axis 2222. The referencing objective 2233 brings the reference radiation to a reference focal region along the optical axis 2222. The reference stage 2235 therefore translates the reference focal region as well as the reference objective 2233. Where the reference focal region is near a surface of the window 2215 some portion of the reference radiation is reflected by the window 2215. A portion of the reflected reference radiation is collimated by the reference objective 2233, transmitted through the beam splitter 2232, and imaged by an imaging lens 2236 onto a camera sensor 2238. Likewise, a transmission radiation from the collimator 2212 is focused by the treatment objective 2234, transmitted through the window 2215, a portion of the transmitted radiation is collimated by the reference objective 2233, transmitted through the beam splitter 2232, and imaged by the imagining lens 2236 onto the camera sensor 2238.

According to an exemplary embodiment of the system 2200, in use the reference focal region is brought to a reference position that is coincident with an outer surface of the window 2215 by translating the reference stage 2235. A reference image captured by the camera 2238 is used to determine the location at which the reference focal region is coincident with the outer surface of the window 2215. The reference image size will have a minimum value where the reference focal region is coincident with the window 2215. At this point the referencing objective 2233 has a focal plane that is generally coincident with the outer surface of the window 2215. The treatment radiation source is then turned ON generating a transmission radiation. Although in some cases, the treatment radiation source is operated at a lower power than is typical during treatment (for example, 10%).

The transmission radiation is focused by the treatment objective 2234 and transmitted through the window 2215. A portion of the transmission radiation is collimated by the reference objective 2233, transmitted through the beam splitter 2232, and imaged by the imaging lens 2236 onto the camera sensor 2238. A transmission image is detected by the camera sensor 2238 that represents a width of the transmission radiation beam at the focal plane of the referencing objective 2233 (e.g., the outer surface of the window). A treatment stage 2240 translates the treatment objective 2234 along the optical axis 2224. The transmission image has minimum size where a position of a transmission focal region is coincident with the focal plane of the referencing objective 2233. Although, the optical axis 2222 of the referencing system and the optical axis of the treatment system 2224 are nominally aligned, in some versions it is advantageous for the two axes to be slightly displaced from one another. A translation stage 2242 is used in some embodiments to displace the reference system optical axis 2222. Once, the transmission focal region is positioned coincident with the outer surface of the window, the treatment stage can be zeroed and the referencing system can be removed and treatment can be performed.

The example uses of feedback informed EMR-based treatment described above (e.g., detection of deleterious and advantageous plasma events during treatment and accurate placement of the focal region) have generally been concerned with providing a safe and effective treatment. Additional uses of feedback informed EMR-based treatment may be concerned with additional objectives, for example capturing and documenting tissue images to aid in determination of a diagnosis or demonstrating positive treatment results.

Tissue Imaging Examples

EMR-based treatment informed by tissue imaging feedback has wide-ranging uses and benefits for dermatologic and aesthetic treatments. For example, according to some embodiments, tissue imaging allows the user to accurately target a treatment site during EMR-based treatment. Another exemplary use of tissue imaging is to provide documentation of treatment results overtime (e.g., pre-treatment images and post-treatment images). According to still other embodiments, tissue imaging is used to ascertain a diagnosis or a treatment plan for a condition prior to treatment, or an endpoint during a treatment. The goal of many exemplary EMR-based skin treatments is aesthetic (e.g., relating to the appearance of the skin). In these cases, imaging of the skin undergoing treatment provides some of the most important feedback to treatment stakeholders (patients and practitioners).

Figure 23:
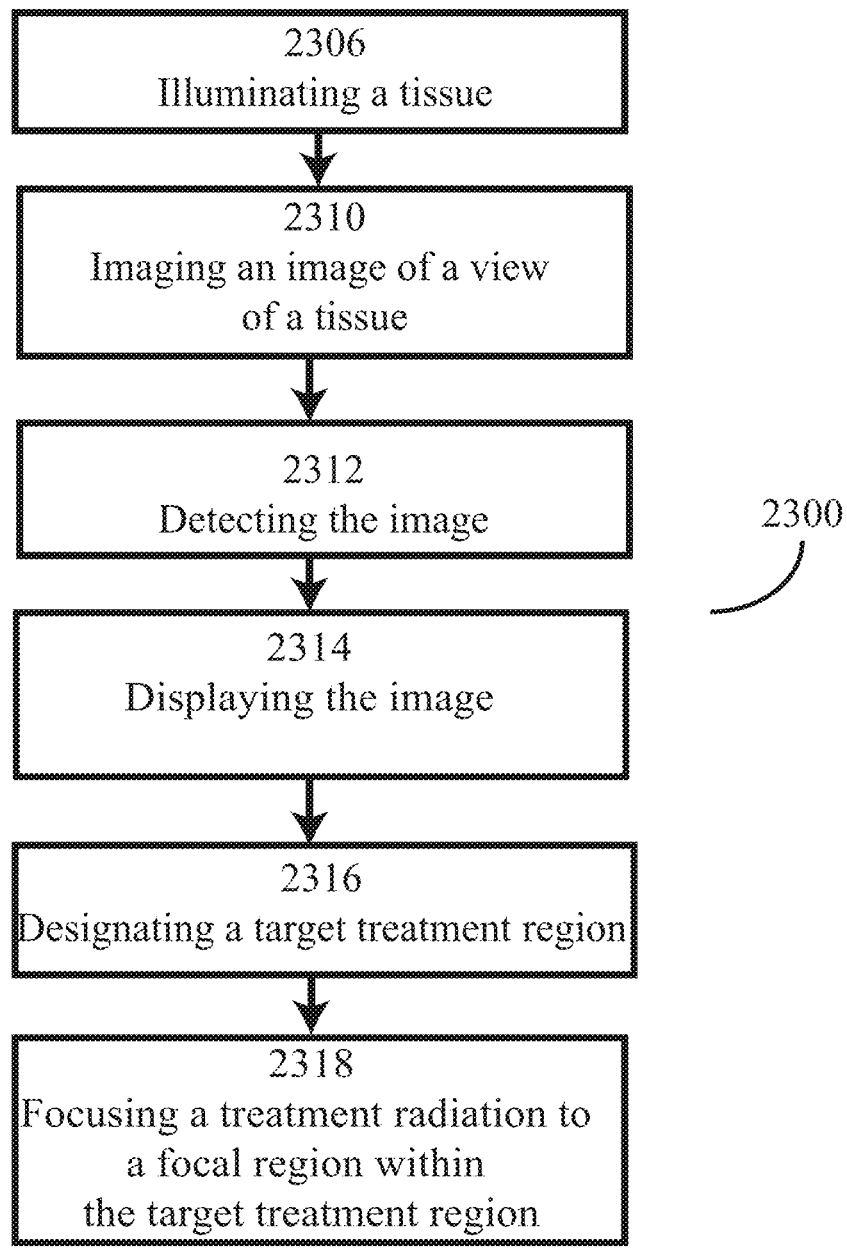
FIG. 23 illustrates a flow chart for a method of imaging and radiation-based treatment, according to some embodiments.

FIG. 23 illustrates a flow chart for a method 2300 of imaging and radiation-based treatment, according to some embodiments. The method 2300 begins by illuminating a tissue with an imaging radiation 2306. Typically, illumination of the tissue is achieved in part by using an illumination source. Illumination may be performed in a number ways including: bright-field illumination, where the imaging radiation is provided substantially on-axis to an imaging system and dark-field illumination, where the imaging radiation is provided substantially off-axis to the imaging system. In some embodiments, the imaging radiation is substantially monochromatic. In other embodiments, the imaging radiation is substantially broadband (e.g., white light).

Next, an image of a view of the tissue is imaged 2310. Imaging is at least partially performed using a focus optic (e.g., objective). The view in some cases is a field of view of a focal region associated with the focus optic. In some embodiments, imaging the image 2310 includes using one more additional optics in conjunction with the focus optic. For example, the focus optic may significantly collimate light from the view and a tube lens may be used to form the image from the collimated light. The image may be formed at an image plane.

Next, the image is detected 2312. Typically, a detector is used to detect the image. Examples of detection include: photodetection, confocal photodetection, interferometric detection, and spectroscopic detection. The detector may detect the image at the image plane. The image may be detected by an image sensor. Examples of image sensors include semiconductor charge-coupled devices (CCD), active pixel sensors in complementary metal-oxide-semiconductor (CMOS), and N-type metal-oxides-semiconductor (NMOS). Image sensors typically output a detected image in a two-dimensional (2D) matrix of data (e.g., bitmap).

The image is then displayed 2314. Typically, the image is displayed by an electronic visual display. Examples of displays include: electroluminescent (EL) displays, liquid crystal (LC) displays, light-emitting diode (LED)-backlit liquid crystal (LC) displays, light-emitting diode (LED) displays (e.g., organic LED (OLED) displays, and active-matrix organic LED (AMOLED) displays), plasma displays, and quantum dot displays. The displayed image is viewed by a designated user (e.g., clinician). In some cases, the image is recorded and stored, for example by the controller 2419. According, to some embodiments the displayed image is used to target a region of tissue needing treatment.

A target treatment region is then designated 2316 within the tissue. In some embodiments, the target treatment region is designated based in part on the image. For example, the target treatment region may be designated 2316 based upon an apparent excess of pigment (e.g., dermal melanin) in a portion of the tissue as displayed in the image. In some cases, a clinician viewing the displayed image designates the target treatment region. Alternatively, in some embodiments, a controller automatically designates the target treatment region based upon the image. The target treatment region is typically at least partially present in the image.

Finally, a treatment radiation is focused to a focal region within the treatment region 2318. Typically, the treatment radiation is focused using the focus optic and configured to perform an effect within the tissue (e.g., selectively generate thermionic plasma at a chromophore; achieve a cosmetic effect). In some embodiments, parameters affecting the treatment radiation are controlled based in part upon the image. Parameters affecting treatment with the treatment radiation are described in detail above. In some embodiments, the focal region is scanned within the target treatment region In some embodiments, the view is scanned from a first region to a second region of the tissue. Examples of scanning include: tipping/tilting the view, rotating the view, and translating the view. Further description of relevant scanning means is described in U.S. patent application Ser. No. 16/219,809 "Electromagnetic Radiation Beam Scanning System and Method," to Dresser et al., incorporated herein by reference. In some embodiments, the view located at the first region overlaps with the view located at the second region. In this case some of the tissue is present in both the first region and the second region. In some other embodiments, the view located at the first region does not overlap with the view located at the second region. In some embodiments, scanning of the view is achieved with feedback related to the view position. For example, in some cases the view is scanned by moving the focus optic with two linear stages. Feedback from encoders present on each linear stage may be used to infer the position of the view when located at the first region and/or the second region.

A second image may be imaged of the view from the second region. Typically, imaging the second image is performed in the same manner as imaging the first image 2310, only the location of the view is different between the two steps. Imaging is at least partially performed using the focus optic. The view in some cases is the field of view of the focal region associated with the focus optic. The second image may be detected. Typically, detecting the second image is performed in the same manner as detecting the first image 2312, the only difference being the second image is detected instead of the first image.

In some cases, the first image and the second image are stitched together into a stitched image (or map). The stitched image may also include additional images taken with the view located at additional regions. The stitched image may be used to document a pre-treatment image of the tissue, or a post-treatment image of the tissue. Any of the first image the second image, and the stitched image may be taken prior to treatment and used to support a determination of a diagnosis, for example by a medical professional. Likewise, any of the first image, the second image, and the stitched image may be taken during or after treatment to demonstrate effectiveness of treatment or to look for end-points during treatment, which can suggest treatment be ended.

Figure 24:
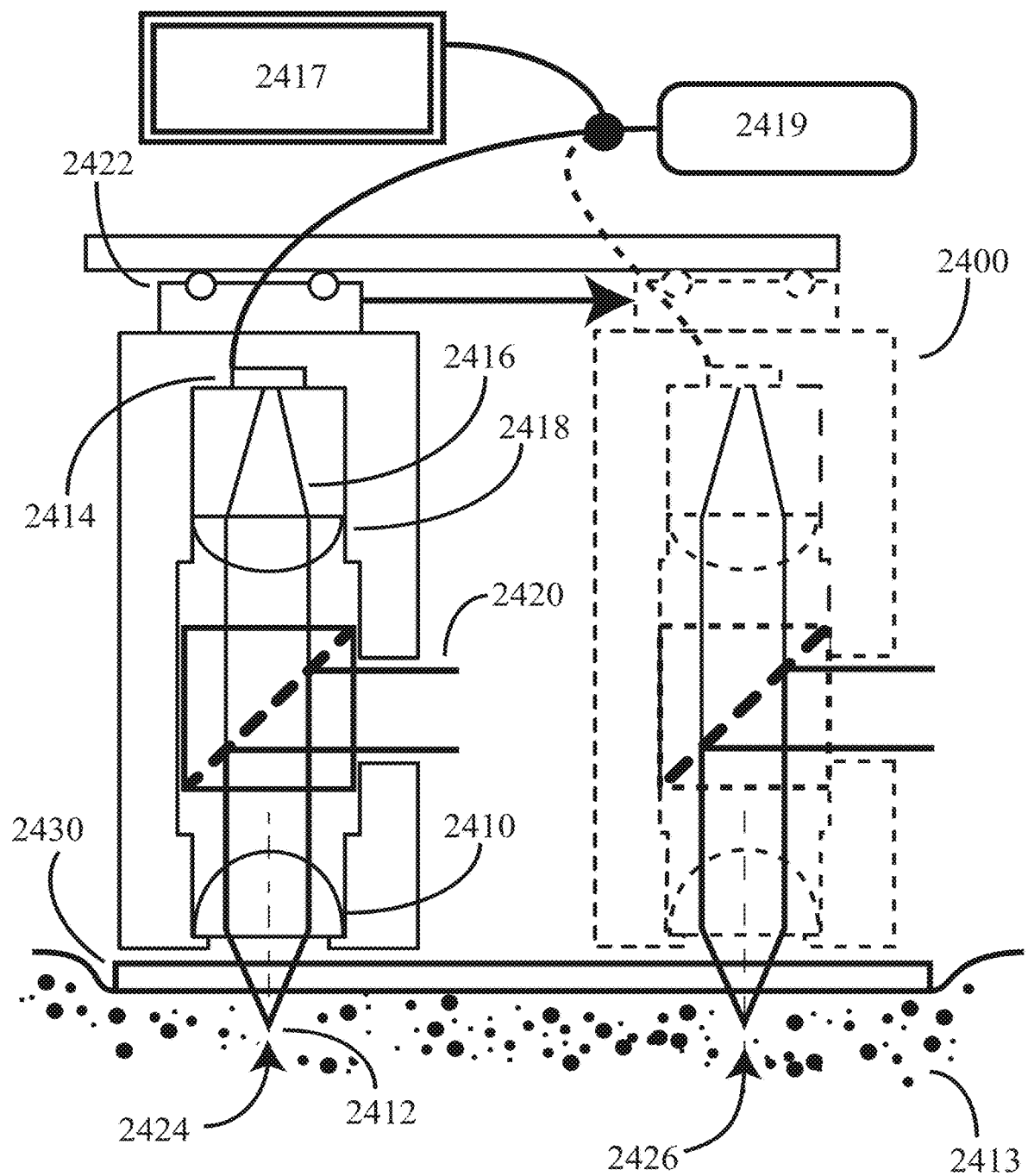
FIG. 24 illustrates a schematic of an imaging and radiation-based treatment system, according to some embodiments.

Referring to FIG. 24 schematics are shown for a tissue imaging and treatment system 2400, according to some embodiments. The imaging and treatment system 2400 includes a focus optic 2410. The focus optic 2410 (e.g., objective) is configured to image a view 2412 of a tissue 2413. A detector 2414 is configured to detect an image 2416 formed at least in part by the focus optic 2410. The detector 2414 is communicative with a display 2417. The display is configured to display the image to a designated user (e.g., clinician). According to some embodiments, a tube lens 2418 is used in conjunction with the focus optic 2410 to form the image 2416. The detector 2414 is communicative with a controller 2419, such that data associated with the detected image from the detector is input to the controller 2419. The focus optic 2410 is used for delivery of a treatment radiation 2420 as well as imaging. A scanner 2422 is configured to scan the view 2412. The scanner typically scans the view in at least one dimension. In some embodiments, the scanner 2422 scans the view in all three dimensions. Referring to FIG. 24, the scanner 2422 is shown scanning the view 2412 from a first region 2424 to a second region 2426 of the tissue 2413.

As the scanner 2422 scans the view 2412, the focus optic 2410 images a first image at the first region 2424 and a second image at the second region 2426. The first image and the second image are both detected by the detector 2414. And, data associated with the first detected image and the second detected image are input to the controller 2419. In some embodiments, the data associated with multiple images are stitched together by the controller 2419, yielding a stitched image (or map). The stitched image and/or one or more images can be recorded and stored by the controller for future viewing. In some embodiments, data from one or more images are used to determine a treatment region. According to some embodiments, determining the treatment region is done automatically by the controller. In other embodiments, determining the treatment region is done manually by the designated user after viewing one or more images.

The treatment radiation 2420 is focused to a focal region by the focus optic 2410. And, the focal region is directed to the treatment region. According to some embodiments, the scanner 2422 is configured to scan the focal region within the treatment region. Some embodiments of the system 2400 include a window 2430 that is placed in contact with a surface of the tissue 2413. The window 2430 can serve several purposes, one being to datum an outer surface of the tissue. The window 2430 therefore allows the focal region to be reliably located within the tissue 2413 a predetermined depth from the surface of the tissue 2413.

Figure 25:
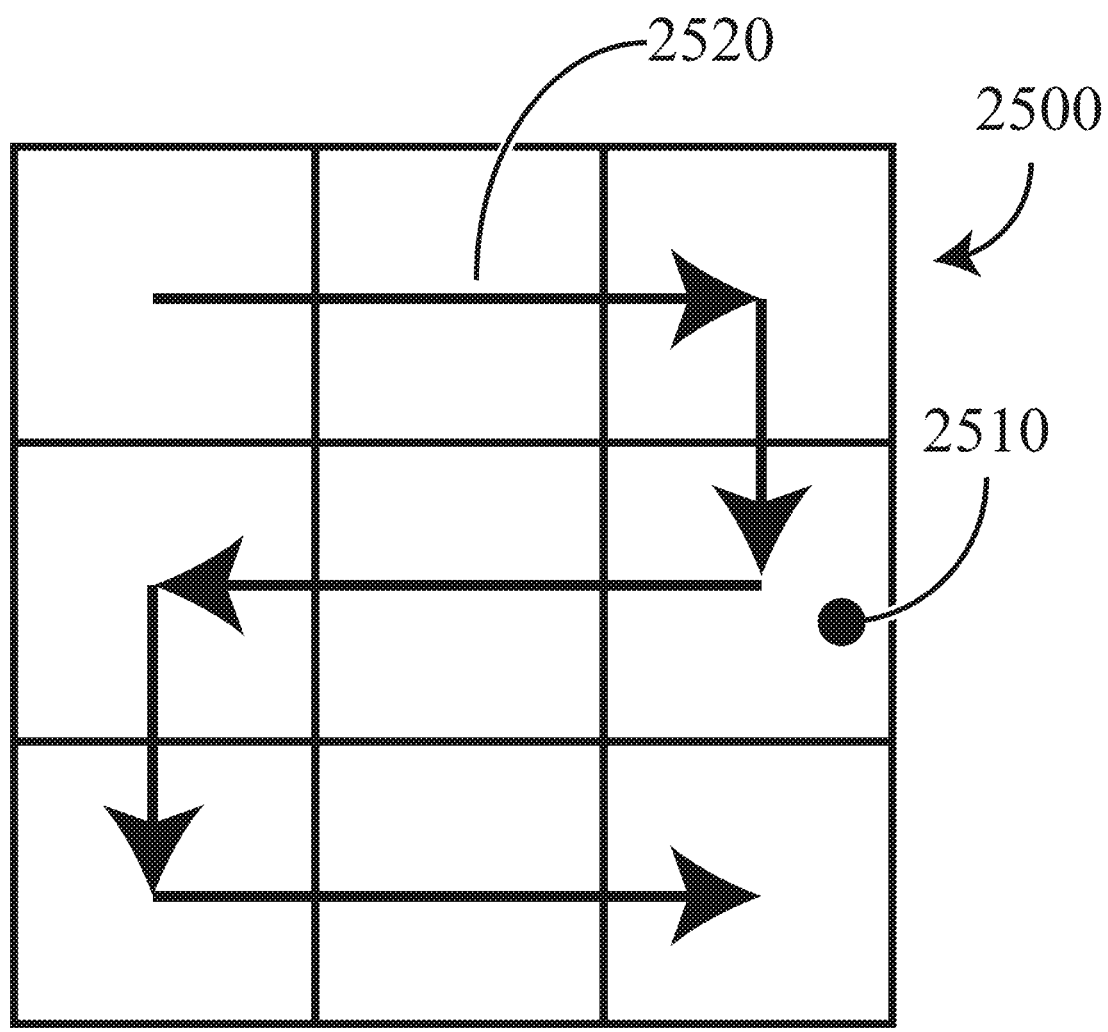
FIG. 25 schematically illustrates a stitched image, according to some embodiments

FIG. 25 schematically illustrates a stitched image (or map) 2500 according to some embodiments. The stitched image 2500 includes a number (e.g., 9) individual images 2510. A scan path 2520 shows a path taken by a view as it traverses a tissue. The scan path shown includes a raster pattern although other patterns are possible (e.g., spiral). Each individual image 2510 is taken at a point located along the scan path. The stitched image 2500 may be formed from the individual images in several ways. For example, if a position of the view is estimate-able for each individual image (e.g., through scanner feedback), the stitched image 2500 may be constructed through dead-reckoning calculations. Alternatively, the stitched image 2500 may be constructed using machine vision algorithms for stitching. A first example imaging stitching software is Hugin-Panorama photo stitcher. Hugin is an open source project hosted at http://hugin.Sourceforge.net. A second example image stitching software is a Photomerge tool within Adobe Photoshop. A particular individual embodiment is provided below to further explain tissue imaging in an EMR treatment device.

Tissue Imaging Example 1

Figure 26A:
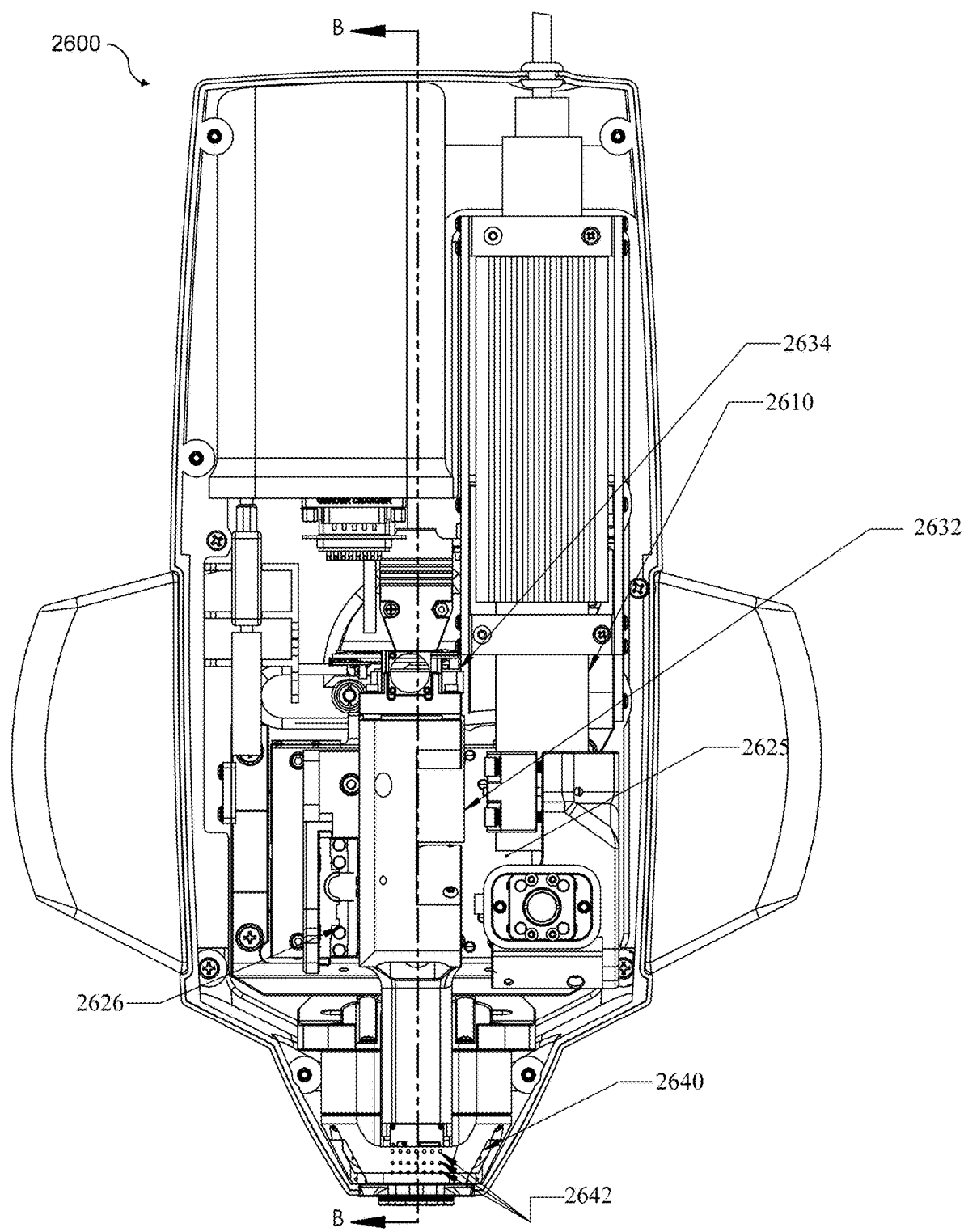
FIG. 26A illustrates a front view of an exemplary version of an imaging and radiation-based treatment system, according to some embodiments.
Figure 26B:
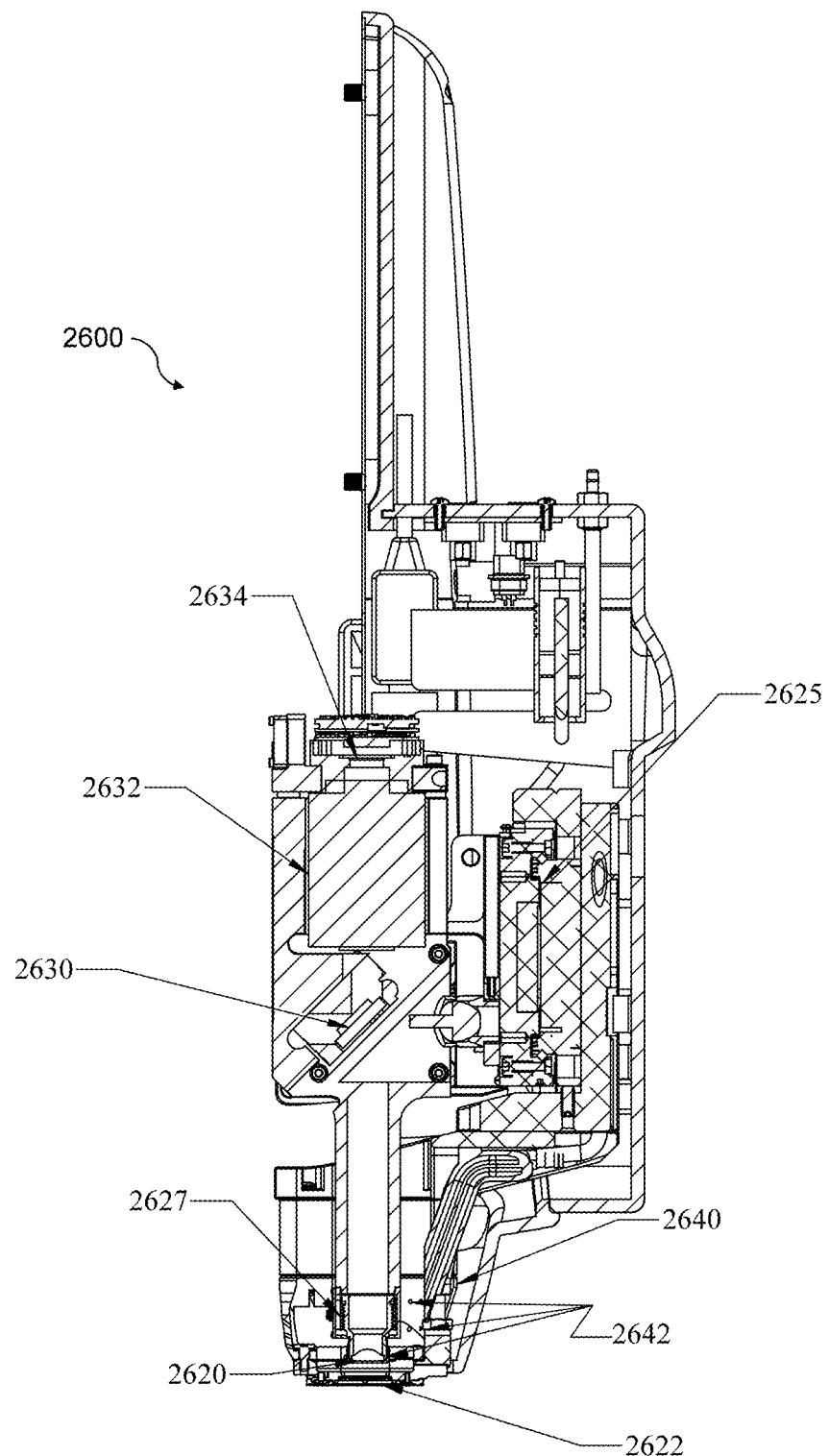
FIG. 26B illustrates an exemplary version of an imaging and radiation-based treatment system, according to some embodiments.

FIGS. 26A-26B illustrate schematics of an example tissue imaging and treatment system 2600. FIG. 26A shows a front view of the system 2600. FIG. 26B shows a cross-sectional view of the system 2600 taken along a B-B section line in FIG. 26A.

The system 2600 includes a fiber laser 2610. The fiber laser 2610 is configured to output a treatment radiation. An example of a fiber laser is a Feibo 1060 nm, 40 W, 20 Khz, fiber laser from Feibo Laser Technologies Co., Ltd. Of Shanghai, China. The treatment radiation is directed by an optical system to a focus optic 2620 that focuses the treatment radiation through a window 2622 to a focal region in a tissue (not shown). The optical system is configured to allow the focus optic 2620 to be scanned in all three dimensions. This allows the focal region of the treatment radiation to be scanned in all three dimensions within the tissue. Scanning is achieved by three separate stages each responsible for a single axis. An X-stage 2625 scans the focus optic in an X-axis. A Y-stage 2626, mounted to the X-stage 2625, scans the focus optic in a Y-axis. And, a Z-stage, mounted to the Y-stage 2626, scans the focus optic in a Z-axis (e.g., generally along an optical axis of the focus optic). An exemplary X-stage is a Dover MMX 50 from Dover Motion of Boxborough, Massachusetts, USA, controlled with an Elmo DC whistle Gold controller from Elmo Motion Controller Ltd. of Petach-Tikva, Israel. An exemplary Y-stage is a Q545.140 stage controlled with E 873 controller both from Physik Instrumente L.P. of Auburn, Massachusetts, USA. An exemplary Z-stage is a New Scale 3M-FS from New Scale Technologies, Inc. of Victor, New York, USA.

The optical system includes a beam splitter 2630 that is configured to reflect the treatment radiation and pass other radiations (e.g., visible light). So, imaging radiation (e.g., visible light) from the tissue is imaged by the focus optic 2620 through the beam splitter 2630. Down beam of the beam splitter 2630, a lens assembly 2632 is located. An example of a lens assembly is a VarioOptic Autofocus lens module part No.: C-C-39NO-250 from Corning Inc. of Corning, New York, USA. The imaging radiation is further imaged by the lens assembly and finally detected by a camera 2634, and more specifically an image sensor within the camera. An example camera is a PL-D755 from PixelLink of Ontario, Canada. The PL-D755 has an image sensor that is a SONY IMX250 CMOS having a global shutter. In order to microscopically image very small areas, the imaging system shown requires illumination of the tissue.

A frame 2640 is shown with a plurality of holes 2642 throughout it. Within the holes 2642, multiple fiber optic bundles (not shown) are placed. In an exemplary illumination scheme 12 fiber optic bundles housed within 0.06" diameter stainless steel tubes are placed in holes 2642 positioned around the frame 2640. The fiber optic bundles converge into a single bundle at a distal end. The single bundle is placed in optical communication with a light source. An exemplary light source is a daylight white 6500K 38 W light engine part number FTIII24015 from Fiberoptics Technology Incorporated of Pomfret, Connecticut, USA. The holes 2642 are angled toward the window 2622 and therefore light from the fiber optic bundles is directed toward the tissue as it exists the bundles. Illuminating at an angle relative the optical axis of the focus optic may be referred to as dark-field illumination. In some embodiments, dark-field illumination is advantageous as specular reflection from the window surfaces is not imaged (as glare) by the focus optic. In other embodiments, illumination is provided generally coaxially with the optical axis. This technique of illumination may be referred to as bright-field illumination. Bright-field illumination is advantageous in some embodiments, as it provides greater illumination density within the view of the focus optic. In order to demonstrate practicality, images taken with the example imaging system are described.

Figure 27A:
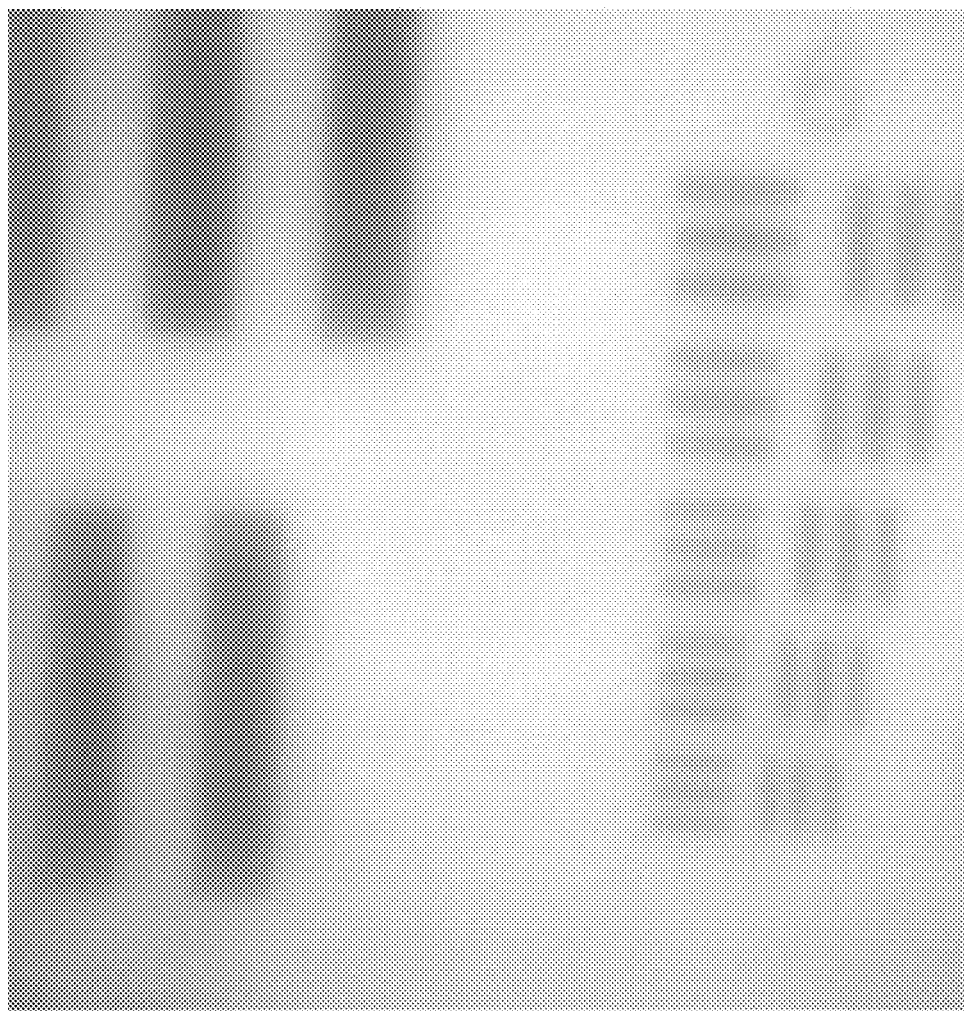
FIG. 27A shows a black-and-white image taken using an exemplary version of an imaging and radiation-based treatment system, according to some embodiments; and, FIG. 27B shows a stitched black-and-white image including multiple images taken using an exemplary version of an imaging and radiation-based treatment system, according to some embodiments.
Figure 27B:
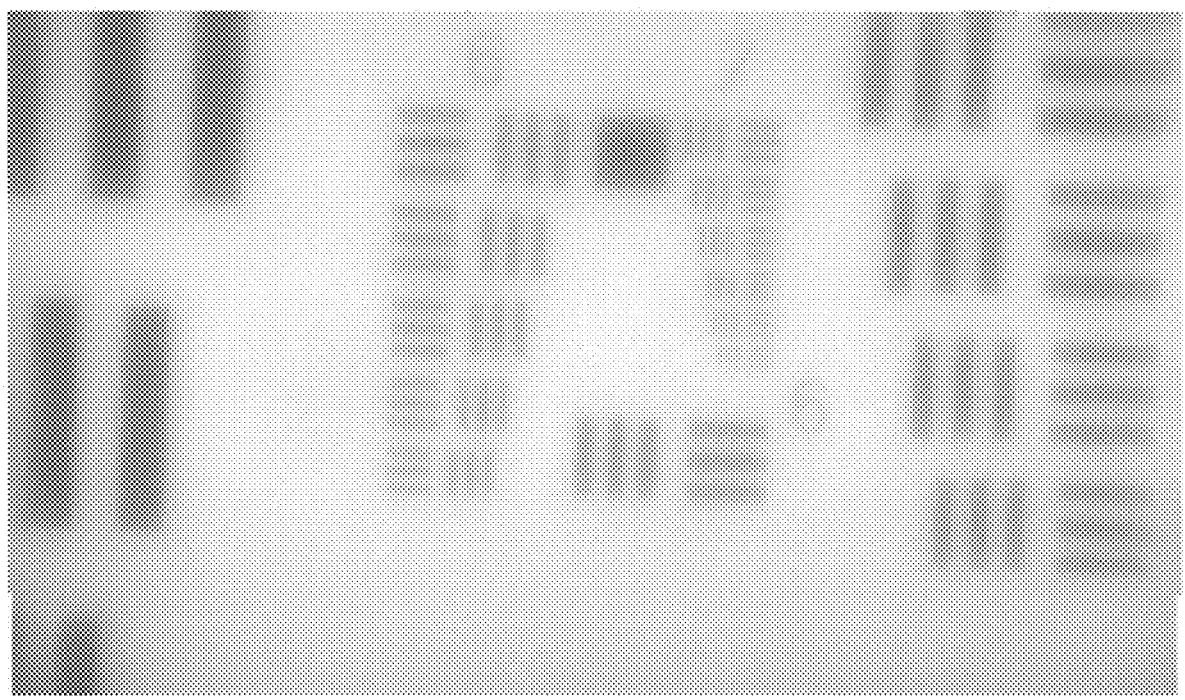

FIG. 27A shows an image 2710 taken by the example system 2600 shown in FIGS. 26A-B. This image 2710 was taken of an Air Force 1951 target. 18 images like this image 2710 were taken (2 rows of 9). The 18 images were stitched together into a stitched image 2720, which is shown in FIG. 27B. Stitching was automatically performed using the Photomerge tool in Adobe Photoshop. Reviewing the stitched image 2720 shows that Group 7 element 6 is resolvable. Lines in Group 7 element 6 are approximately 2.2 μm wide. Microscopic imaging is therefore practical using the example system 2600 shown in FIGS. 26A-B.

Additional Embodiments

In some embodiments, the repetition rate of the input laser beam can be faster than the decay rate of the plasma in the target tissue/target material. This can allow for continuous (e.g., temporally continuous, spatially continuous, etc.) generation of plasma. The area of the treatment region/target region (e.g., region in which plasma is generated) can be controlled by changing the repetition rate of the laser beam.

Additional embodiments include alternative imaging technologies used in conjunction with EMR-based treatment. These alternative imaging technologies include: microscopic imaging, wide field of view imaging, reflectance confocal imaging, optical coherence tomography imaging, optical coherence elastography imaging, coherent anti-stokes Raman spectroscopy imaging, two-photon imaging, second harmonic generation imaging, phase conjugate imaging, photoacoustic imaging, infrared spectral imaging, and hyperspectral imaging.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. "Approximately," "substantially," or "about" can include numbers that fall within a range of 1%, or in some embodiments within a range of 5% of a number, or in some embodiments within a range of 10% of a number in either direction (greater than or less than the number) unless otherwise stated or otherwise evident from the context (except where such number would impermissibly exceed 100% of a possible value). Accordingly, a value modified by a term or terms, such as "about," "approximately," or "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure also includes embodiments in which more than one, or all of the group members are present in, employed in, or otherwise relevant to a given product or process. Furthermore, it is to be understood that the disclosed embodiments provide all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the disclosed embodiments where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the disclosed embodiments, or aspects of the disclosed embodiments, is/are referred to as comprising particular elements, features, etc., certain embodiments of the disclosure or aspects of the disclosure consist, or consist essentially of, such elements, features, etc. For purposes of simplicity those embodiments have not in every case been specifically set forth in so many words herein. It should also be understood that any embodiment or aspect of the disclosure can be explicitly excluded from the claims, regardless of whether the specific exclusion is recited in the specification. For example, any one or more active agents, additives, ingredients, optional agents, types of organism, disorders, subjects, or combinations thereof, can be excluded.

Where ranges are given herein, embodiments of the disclosure include embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise. It is also understood that where a series of numerical values is stated herein, the disclosure includes embodiments that relate analogously to any intervening value or range defined by any two values in the series, and that the lowest value may be taken as a minimum and the greatest value may be taken as a maximum. Numerical values, as used herein, include values expressed as percentages.

It should be understood that, unless clearly indicated to the contrary, in any methods claimed herein that include more than one act, the order of the acts of the method is not necessarily limited to the order in which the acts of the method are recited, but the disclosure includes embodiments in which the order is so limited. It should also be understood that unless otherwise indicated or evident from the context, any product or composition described herein may be considered "isolated".

As used herein the term "comprising" or "comprises" is used in reference to compositions, methods, and respective component(s) thereof, that are essential to the disclosed embodiments, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

Although a few variations have been described in detail above, other modifications or additions are possible.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method of treatment, comprising:
   imaging a target tissue with imaging radiation delivered along an optical pathway to create a signal radiation emanating from the target tissue, the signal radiation generated by plasma formed in the target tissue through interaction with the imaging radiation;
   scanning the imaging radiation along the optical axis to alter characteristics of the signal radiation;
   determining one or more aspects of the target tissue based on the altered signal radiation;
   receiving, from a controller in electrical communication with the optical pathway and based on the determined one or more aspects of the target tissue, one or more suggested changes to a set of baseline parameters of a treatment radiation;
   adjusting, based on the received one or more suggested changes, the set of baseline parameters to result in an adjusted treatment radiation; and
   emitting the adjusted treatment radiation delivered along the optical pathway to treat the target tissue.

2. The method of claim 1, wherein the one or more aspects include at least one of a location of a pigment, a proportion of melanin, and a depth of a dermal-epidermal layer junction.

3. The method of claim 1, wherein the imaging radiation and the treatment radiation have the same wavelength.

4. The method of claim 1, wherein the adjusted set of baseline parameters includes a location of a focal region within the tissue.

5. The method of claim 1, wherein the baseline parameters include at least one of a focal depth, a wavelength, a polarization, and an intensity.

6. The method of claim 1, wherein the imaging comprises at least one of microscopic imaging, wide field of view imaging, reflectance confocal imaging, optical coherence tomography imaging, optical coherence elastography imaging, coherent anti-stokes Raman spectroscopy imaging, two-photon imaging, second harmonic generation imaging, phase conjugate imaging, photoacoustic imaging, infrared spectral imaging, and hyperspectral imaging.

7. The method of claim 1, wherein the target tissue comprises skin afflicted with at least one of post inflammatory hyperpigmentation (PIH), dark skin surrounding eyes, dark eyes, café au lait patches, Becker's nevi, Nevus of Ota, congenital melanocytic nevi, ephelides (freckles) and lentigo.

8. A method of treatment, comprising:
   irradiating a target tissue with an imaging EMR beam delivered along an optical pathway to image the target tissue;
   detecting at least a portion of a signal radiation caused by the imaging EMR beam reflecting off of the target tissue and by plasma generated in the target tissue;
   scanning the imaging EMR beam along the optical pathway to adjust characteristics of the signal radiation;
   determining one or more aspects of the target tissue based on the adjusted characteristics of the signal radiation;
   receiving, from a controller and based on the determined one or more aspects of the target tissue, one or more recommended adjustments to parameters of a treatment EMR beam;
   adjusting the parameters of the treatment EMR beam based on the one or more recommended adjustments; and
   irradiating a target tissue with the adjusted treatment EMR beam delivered along the optical pathway to treat the target tissue.

9. The method of claim 8, wherein the one or more aspects include at least one of a proportion and a distribution of melanin in the target tissue.

10. The method of claim 9, wherein the one or more parameters include energy per pulse, focus angle, and depth of a focal region of the treatment EMR beam.

11. The method of claim 9, further comprising:
    generating a map of the one or more aspects of the target tissue; and
    varying the adjusted treatment radiation based on the generated map.

12. The method of claim 9, further comprising:
    recommending, based at least partially on at least one of the proportion and the distribution of melanin in the target tissue, one or more changes to the one or more parameters of the treatment EMR beam to a designated personnel.

* * * * *